US006988005B2

(12) United States Patent
McGraw et al.

(10) Patent No.: US 6,988,005 B2
(45) Date of Patent: *Jan. 17, 2006

(54) MULTI-FUNCTIONAL PORTABLE ELECTRO-MEDICAL DEVICE

(75) Inventors: Michael B. McGraw, Vancouver, WA (US); William A. Rux, Hillsboro, OR (US); William J. Carroll, Sedro Woolley, WA (US); Richard M. Terrell, Vancouver, WA (US); Randy Alan Murphy, Vancouver, WA (US)

(73) Assignee: International Rehabilitative Sciences, Inc., Vancouver, WA (US)

( * ) Notice: Subject to any disclaimer, the term of this patent is extended or adjusted under 35 U.S.C. 154(b) by 36 days.

This patent is subject to a terminal disclaimer.

(21) Appl. No.: 10/133,380

(22) Filed: Apr. 29, 2002

(65) Prior Publication Data

US 2004/0015203 A1    Jan. 22, 2004

Related U.S. Application Data

(63) Continuation of application No. 09/566,081, filed on May 8, 2000, now Pat. No. 6,393,328.

(51) Int. Cl.
*A61N 1/00* (2006.01)
(52) U.S. Cl. .................................................. 607/67
(58) Field of Classification Search ............ 607/1–156
See application file for complete search history.

(56) References Cited

U.S. PATENT DOCUMENTS

| | | | |
|---|---|---|---|
| 3,648,708 A | 3/1972 | Haeri | |
| 3,783,880 A | 1/1974 | Kraus | |
| 3,817,254 A | 6/1974 | Maurer | |
| 3,893,462 A | 7/1975 | Manning | |
| 3,902,502 A | 9/1975 | Liss et al. | |
| 4,026,304 A | 5/1977 | Levy | |
| 4,033,336 A | 7/1977 | Murawski et al. | |
| 4,140,131 A | 2/1979 | Dutcher et al. | |
| 4,147,171 A | 4/1979 | Greene et al. | |
| 4,175,565 A | 11/1979 | Chiarenza et al. | |
| 4,177,819 A | 12/1979 | Kofsky et al. | |
| 4,211,238 A | 7/1980 | Shu et al. | |
| 4,232,680 A | 11/1980 | Hudleson et al. | |
| 4,239,048 A | 12/1980 | Steuer | |
| 4,287,771 A | 9/1981 | Dugot | |
| 4,295,474 A | 10/1981 | Fischell | |
| 4,300,566 A | 11/1981 | Stindt et al. | |

(Continued)

FOREIGN PATENT DOCUMENTS

DE     2505047     8/1976

(Continued)

OTHER PUBLICATIONS

"Stimulation of Bone Healing in new Fractures of the Tibial Shaft Using Interferential Currents" by Fourie et al., *Physiotherapy Research International*, 2(4) pp. 255-266, 1997.

(Continued)

*Primary Examiner*—Scott M. Getzow
(74) *Attorney, Agent, or Firm*—Blank Rome LLP

(57) ABSTRACT

A multi-functional portable electro-medical device that is capable of providing muscle stimulation and interferential current stimulation. The multi-functional portable electro-medical device includes a multitude of safety features which are designed to prevent injury to the user while at the same time to ensure that the portable power electro-medical device is easy to use. The portable electro-medical device can be programmed to impart any combination of wave therapy to the patient.

8 Claims, 56 Drawing Sheets

U.S. PATENT DOCUMENTS

| | | |
|---|---|---|
| 4,324,253 A | 4/1982 | Greene et al. |
| 4,340,063 A | 7/1982 | Maurer |
| 4,342,317 A | 8/1982 | Axelgard |
| 4,392,496 A | 7/1983 | Stanton |
| 4,408,609 A | 10/1983 | Axelgard |
| 4,430,999 A | 2/1984 | Brighton et al. |
| 4,442,846 A | 4/1984 | Brighton et al. |
| 4,459,988 A | 7/1984 | Dugot |
| 4,467,808 A | 8/1984 | Brighton |
| 4,467,809 A | 8/1984 | Brighton |
| 4,480,830 A | 11/1984 | Petrofsky et al. |
| 4,487,834 A | 12/1984 | Brighton |
| 4,506,674 A | 3/1985 | Brighton et al. |
| 4,509,520 A | 4/1985 | Dugot |
| 4,535,775 A | 8/1985 | Brighton et al. |
| 4,549,547 A | 10/1985 | Brighton et al. |
| 4,556,051 A | 12/1985 | Maurer |
| 4,576,171 A | 3/1986 | Key |
| 4,583,550 A | 4/1986 | Montalbano et al. |
| 4,598,713 A | 7/1986 | Hansjurgens |
| 4,600,010 A | 7/1986 | Dugot |
| 4,607,639 A | 8/1986 | Tanagho et al. |
| 4,622,973 A | 11/1986 | Agarwala |
| 4,641,633 A | 2/1987 | Delgado |
| 4,642,769 A | 2/1987 | Petrofsky |
| 4,667,683 A | 5/1987 | Dugot |
| D290,095 S | 6/1987 | Montalbano et al. |
| D290,751 S | 7/1987 | Montalbano et al. |
| 4,703,755 A | 11/1987 | Tanagho et al. |
| 4,719,922 A | 1/1988 | Padjen et al. |
| 4,731,850 A | 3/1988 | Levitt et al. |
| 4,771,779 A | 9/1988 | Tanagho et al. |
| 4,832,033 A | 5/1989 | Maher et al. |
| 4,848,347 A | 7/1989 | Hall |
| 4,879,749 A | 11/1989 | Levitt et al. |
| 4,895,154 A | 1/1990 | Bartelt et al. |
| 4,895,161 A | 1/1990 | Cudahy et al. |
| 4,919,139 A | 4/1990 | Brodard |
| 4,926,864 A | 5/1990 | Dufresene et al. |
| 4,926,865 A | 5/1990 | Oman |
| 4,928,959 A | 5/1990 | Bassett et al. |
| 4,947,844 A | 8/1990 | McDermott |
| 4,976,264 A | 12/1990 | Petrofsky |
| 4,989,605 A | 2/1991 | Rossen |
| 5,014,699 A | 5/1991 | Pollack et al. |
| 5,014,705 A | 5/1991 | Graupe et al. |
| 5,048,523 A | 9/1991 | Yamasawa et al. |
| 5,063,929 A | 11/1991 | Bartelt et al. |
| 5,065,083 A | 11/1991 | Owens |
| 5,069,211 A | 12/1991 | Bartelt et al. |
| 5,070,873 A | 12/1991 | Graupe et al. |
| 5,086,778 A | 2/1992 | Mueller et al. |
| 5,092,329 A | 3/1992 | Graupe et al. |
| 5,097,833 A | 3/1992 | Campos |
| 5,133,354 A | 7/1992 | Kallok |
| 5,161,530 A | 11/1992 | Gamble |
| 5,217,009 A | 6/1993 | Kronberg |
| 5,285,781 A | 2/1994 | Brodard |
| 5,288,459 A | 2/1994 | Lawrence |
| 5,324,317 A | 6/1994 | Reiss |
| 5,370,665 A | 12/1994 | Hudrlik |
| 5,376,105 A | 12/1994 | Hedberg |
| 5,393,296 A | 2/1995 | Rattner |
| 5,413,596 A | 5/1995 | Kronberg |
| 5,456,686 A | 10/1995 | Klapper et al. |
| 5,512,057 A | 4/1996 | Reiss et al. |
| 5,520,612 A | 5/1996 | Winder et al. |
| 5,540,735 A | 7/1996 | Wingrove |
| 5,547,459 A | 8/1996 | Kaufman et al. |
| 5,549,656 A | 8/1996 | Reiss |
| 5,562,718 A | 10/1996 | Palermo |
| 5,573,552 A | 11/1996 | Hansjurgens |
| 5,604,204 A | 2/1997 | Ammann et al. |
| 5,707,346 A | 1/1998 | Graston |
| 5,730,705 A | 3/1998 | Talish et al. |
| 5,738,521 A | 4/1998 | Dugot |
| 5,752,924 A | 5/1998 | Kaufman et al. |
| 5,755,745 A * | 5/1998 | McGraw et al. ............... 607/48 |
| 5,776,173 A * | 7/1998 | Madsen et al. ................ 607/67 |
| 5,792,209 A | 8/1998 | Varner |
| 5,817,138 A | 10/1998 | Suzuki |
| 5,836,995 A | 11/1998 | McGraw et al. |
| 5,916,870 A | 6/1999 | Lee et al. |
| 5,942,499 A | 8/1999 | Radomsky |
| 5,948,428 A | 9/1999 | Lee et al. |
| 5,961,542 A | 10/1999 | Agarwala |
| 5,974,342 A * | 10/1999 | Petrofsky ..................... 607/50 |
| 5,995,873 A | 11/1999 | Rhodes |
| 5,997,490 A | 12/1999 | McLeod |
| 6,011,994 A | 1/2000 | Kronberg |
| 6,022,349 A | 2/2000 | McLeod et al. |
| 6,029,090 A | 2/2000 | Herbst |
| 6,032,677 A | 3/2000 | Blechman et al. |
| 6,034,062 A | 3/2000 | Thies et al. |
| RE36,690 E | 5/2000 | McGraw et al. |
| 6,231,528 B1 | 5/2001 | Kaufman et al. |
| 6,334,069 B1 | 12/2001 | George et al. |
| 6,684,106 B2 * | 1/2004 | Herbst ........................ 607/66 |
| 2002/0077281 A1 | 6/2002 | Vickery |

FOREIGN PATENT DOCUMENTS

| | | |
|---|---|---|
| FR | 24545817 | 11/1980 |
| GB | 2026322 | 2/1980 |
| GB | 2060174 A | 2/1982 |

OTHER PUBLICATIONS

"Bone Healing and Dynamic Interferential Current (DIC)—First Comparative Experimental Animal Sudy in Sheep" by Laabs et al., *Langenbecks Archiv* 1982.

Inferential Therapy To Promote Union of Mandibular Fractures, J.M. Ganne et al., *Australian and New Zealand Journal of Surgery*, vol. 49, No. 1, Feb. 1979, pp. 81-83.

Posterolateral Lumbar Intertransverse Process Spine Arthrodesis with Recombinant Human Bone Morphogenetic Protein 2/hyroxyapatite-tricalcium Phosphate after Laminectomy In the Nonhuman Primate, S.D. Boden et al., *Spine*, Jun. 15, 1999, vol. 24, No. 12; pp. 1179-1185 (abstract only).

CBER Mission/Vision 2004, Strategic Plan for 2004, Center For Biologics Evauation and Research, www.fda.gov/cber/inside/mission.htm, last updated Nov. 5, 1999 (11 pages).

The Bone Morphogenetic Protein Family and Osteogensis, J.M. Wozney, Genetics Institute, Inc., Cambridge, Mol. Reprod. Dev., Jun. 1992, vol. 32 No. 2, pp. 160-167 (Abstract Only).

1995 Volvo Award in Basic Sciences, The Use of an Osteoinductive Growth Factor for Lumbar Spinal Fusion, Part I: Biology of Spinal Fusion, S.D. Boden et al., *Spine*, vol. 20, No. 24, Dec. 15, 1995, pp. 2626-2632.

Bone Morphogenetic Proteins In Human Bone Regeneration, E.H.J. Groeneveld and E.H. Burger, *European Journal of Endocrinology* (2000), vol. 142, pp. 9-21.

Cervical Interbody Fusion Cages. An Animal Model with and without Bone Morphogenetic Protein, T.A. Zdeblick et al., *Spine*, vol. 23, No. 7, Apr. 1998, pp. 758-765.

CBER Tissue Action Plan, Center for Biologics Evaluation and Research, www.fda.gov/cber/tissue/purpose.htm last updated Feb. 4, 2000 (2 pages- p. 1 printed Aug. 2000).

CBER Xenotransplanation Action Plan, Center for Biologics Evaluation and Research, www.fda.gov/cber/xap/xap.htm last updated Oct. 19, 2000 (4 pages).

Inside CBER, Center For Biologics Evaluation and Research, www.fda.gov/cber/inside.htm last updated Oct. 16, 2000 (1 page).

Acceleration of Ossification by Means of Interferential Current by Ulrich et al., *Normal and Abnormal Bone Growth: Basic and Clinical Research*, pp. 469-476, 1985.

European Search Report dated Aug. 10, 2005.

* cited by examiner

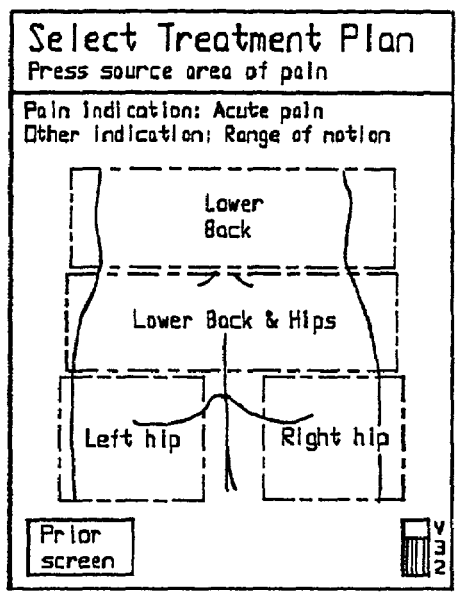
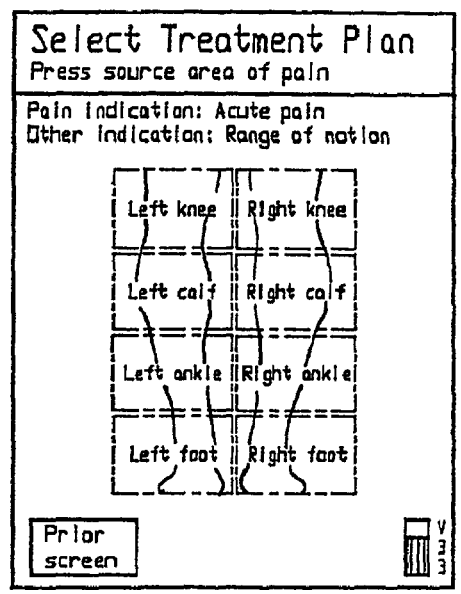
FIG. 80          FIG. 81
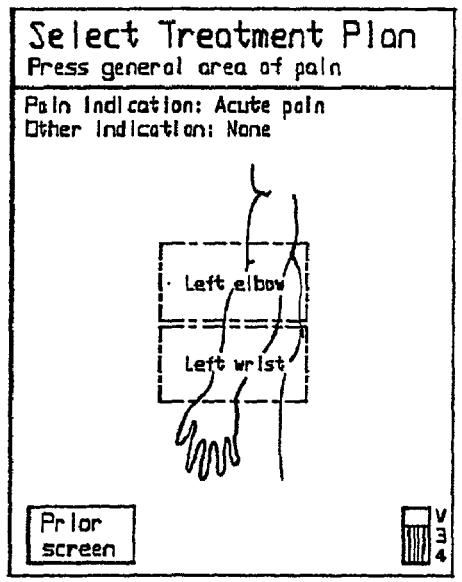
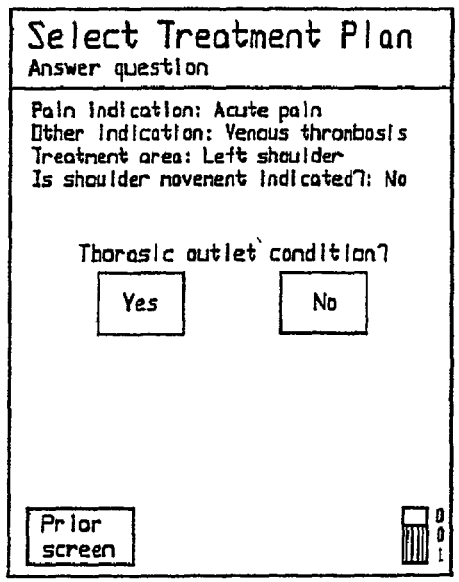
FIG. 82          FIG. 83

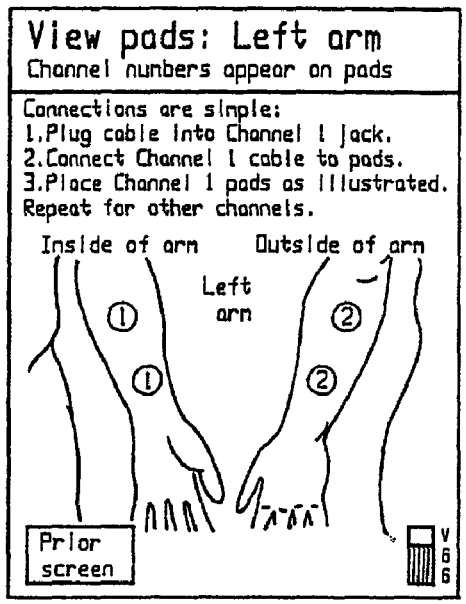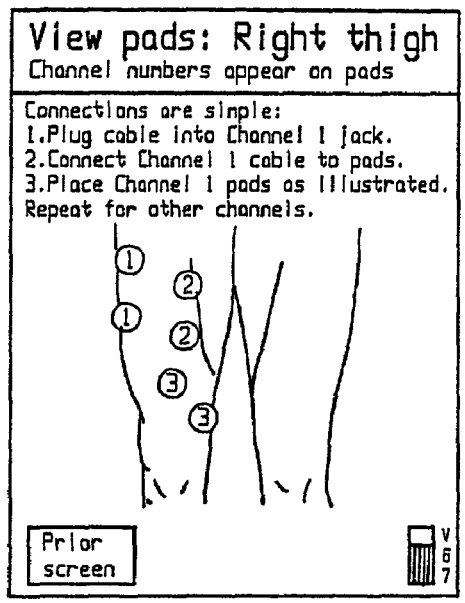
FIG.100  FIG.101
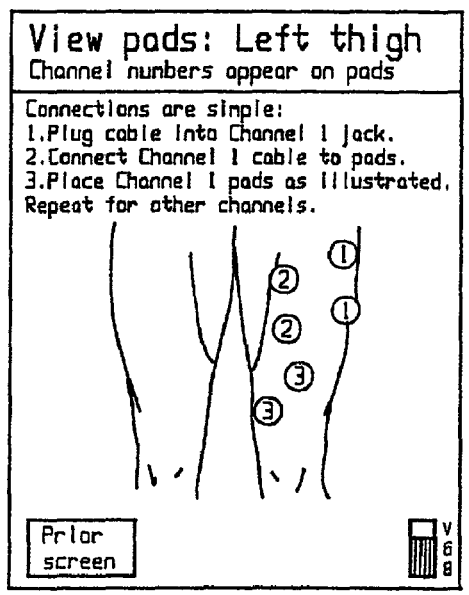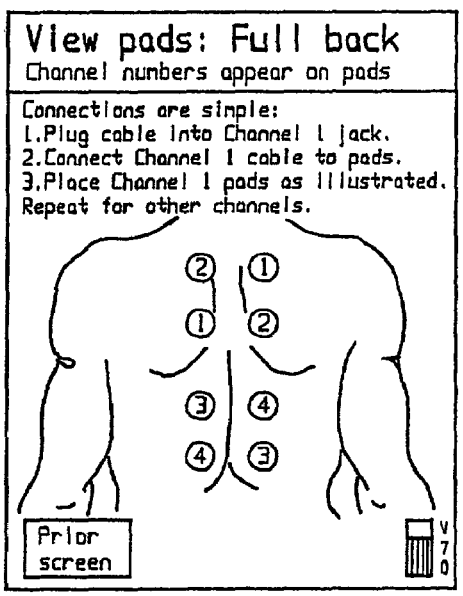
FIG.102  FIG.103

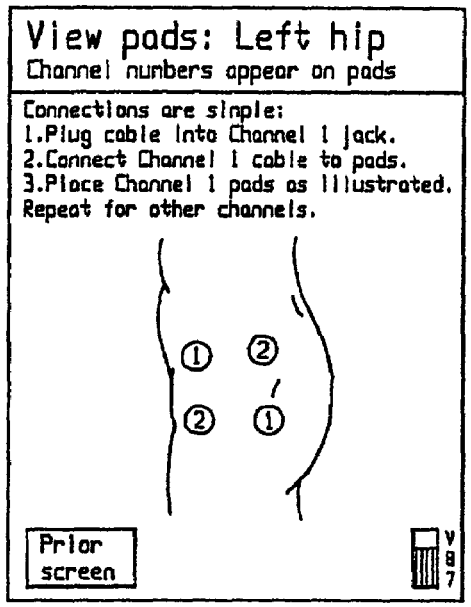
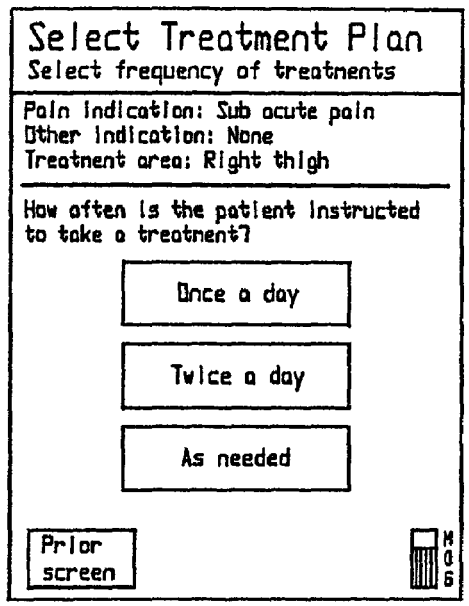
FIG. 120    FIG. 121
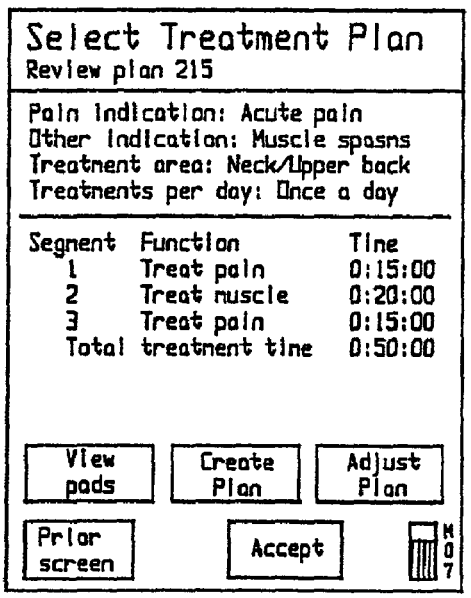
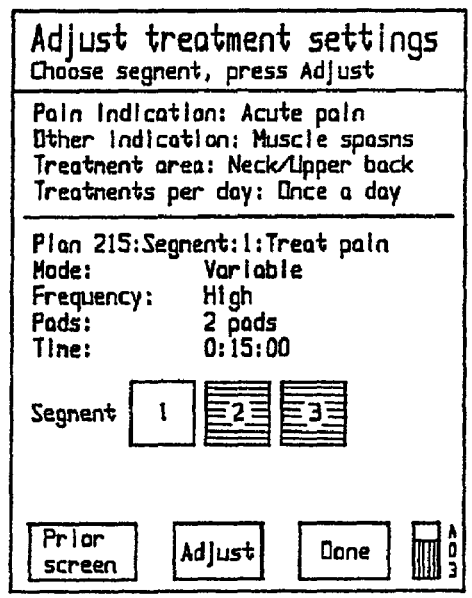
FIG. 122    FIG. 123

Create Treatment Plan
Choose segment press adjust

Pain Indication: Acute pain
Other Indication: Muscle spasms
Treatment area: Upper back
Treatments per day: Twice a day Plan 999:Segment:1:Treat muscle
Mode:      Normal
Contract:  5 seconds
Relax:     2 seconds
Time:      0:15:00

Segment [1] [2] [3]

[Prior screen] [Adjust] [Done]

Adjust treatment settings
Adjust settings for segment 3

Treatment Plan 123
Segment 1 of 2: Treat muscle

Treatment mode: Normal       [Adjust]

Contract time: 5 seconds     [Adjust]

Relax time: 2 seconds        [Adjust]

Treatment time: 0:15:00      [Adjust]

[Prior screen]   [Accept]

Adjust treatment settings
Adjust settings for segment 1

Treatment Plan: 123
Segment 1 of 4: Treat pain

Treatment mode: Continuous   [Adjust]

Frequency: 0 beats/sec.      [Adjust]

Pad selection: 2 pads        [Adjust]

Treatment time: 0:05:00      [Adjust]

[Prior screen]   [Accept]

Adjust treatment settings
Select treatment node

Treatment Plan: 215
Segment 2 of 3: Treat muscle

Current Treatment Mode: Normal

[Normal]    All channels work together

[Alternate] Channels alternate: channels 1-2 are on while 3-4 are off, then they alternate

[Prior screen]

FIG.127

MULTI-FUNCTIONAL PORTABLE ELECTRO-MEDICAL DEVICE

This application is a Continuation of application Ser. No. 09/566,081 Filed on May 8, 2000, now U.S. Pat. No. 6,393,328.

BACKGROUND OF THE INVENTION

The present invention relates generally to portable electro-medical devices. More particularly, the present invention relates to a multi-functional portable electro-medical device that can be programmed to provide any type of electro-medical treatment.

With the increasing application of high technology to medical applications, there has been a trend in recent years to providing as much care as possible as well as sophisticated medical treatment outside of hospitals. That trend has resulted in an increase in the amount of surgery as well as other types of medical treatment, such as rehabilitation services, being performed outside of hospitals in, for example, ambulatory surgery centers or rehabilitation centers, respectively.

SUMMARY OF THE INVENTION

In order to provide an even more cost effective outcome, the present invention obtains the desired medical outcome with medical equipment that can be utilized in the patient's home. In addition to the cost advantages obtained over providing those treatments in an outpatient setting, the use of the present invention by patients in their homes is also more convenient for the patients, since they do not need to travel to an outpatient center for treatment, and they can initiate their own unsupervised treatment at their convenience.

The present invention greatly expands the conditions of the patient that can be treated with an electro-medical device in clinics and at home. The present invention provides the capability to apply any type of electro-medical treatment. For example, one exemplary embodiment of the multi-functional electro-medical device in accordance with the present invention is programmed to apply interferential current stimulation, high voltage muscle stimulation as well as pulsed muscle stimulation treatments. With the ability to provide interferential current stimulation, the multi-functional portable electro-medical device of the present invention provides the ability to treat painful muscle conditions. The multi-functional portable electro-medical device in accordance with the present invention may be programmed to apply many other types of electro-medical treatment such as NEMS, TENS, microcurrent, micro current, high voltage, constant voltage or pulse width, and the like.

The multi-functional portable electro-medical device of the present invention is easy to use and safe. Additionally, an embodiment of a multi-functional portable electro-medical device in accordance with the present invention may include a monitoring system that captures and stores information regarding the use of the device by the patient. By obtaining such usage data, the physician/health care providers who have developed and/or prescribed the treatment for the patient can be satisfied that the patient is indeed receiving the desired treatment and the patient's progress can be measured. In addition, the underwriter of the cost of the treatment can be assured that the patient is actually receiving the treatment. Such monitoring is important in connection with all of the Class II devices, as they are defined in the Food and Drug Administration's Manual, "Classification Names for Medical Devices and In Vitro Diagnostic Products," such as a portable electro-medical device as defined in 21 C.F.R. 890.5850. Such Class II devices are regulated and require a prescription by a doctor but do not require a high degree of supervision. Thus, such devices are used personally by the patient for whom they are prescribed without any supervision at the time of use.

Another embodiment of the multi-functional portable electro-medical device in accordance with the present invention provides an optional removable data storage card which is secured within the multi-functional portable electro-medical device on guide rails that prevent the removable data storage card from being inserted into the portable electro-medical device incorrectly. The guide rails also function to removably secure the data storage card in the correct location within the portable electro-medical device. In addition, as a safety feature, the pins on the pad cables used with the electro-medical device are designed with a large diameter so that they cannot be plugged into a typical household 110 volt electrical outlet. Also, the battery charger cable pin is designed such that it can only plug into the battery charger jack and not into a channel jack, which could damage the portable electro-medical device.

Yet another embodiment of the multi-functional portable electro-medical device in accordance with the present invention determines whether any of the connections between the pads, cables and the stimulator is faulty and then takes appropriate action. The multifunctional portable electro-medical device in accordance the present invention may also be designed such that a channel output level can be changed only in small increments, which assures that a rapid increase or decrease in muscle contraction will not be experienced by the user during treatment if a button is continually depressed.

Other safety features of an embodiment of the multi-functional portable electro-medical device in accordance with the present invention include monitoring the battery charger so that none of the channels of the portable electro-medical device can provide an output to a cable and pad while the battery is being recharged, constantly monitoring the frequency and width of the waveform output by the portable electro-medical device and taking appropriate action if the waveform changes from the desired pattern, monitoring the liquid crystal display of the portable electro-medical device and taking appropriate action if the display is not operating properly and constantly monitoring the battery voltage of the portable electro-medical device and taking appropriate action if the amount of voltage supplied to the microprocessor is incorrect.

An exemplary embodiment of the multi-functional portable electro-medical device in accordance with the present invention includes an interactive liquid crystal display (hereinafter "LCD"). The LCD includes a touch screen through which a user may interact and control the device. The LCD can display buttons that indicate to a user where on the touch screen a user may touch to enter a command. The LCD is also large enough to convey a large amount of information to provide guidance to a user of the device. For example, the LCD is large enough to display diagrams that make it clear to the user how the pads are to be connected to the user's body for a treatment.

An exemplary embodiment of the multi-functional portable electro-medical device in accordance with the present invention uses a software based system to provide multiple treatment capabilities. The device is a finite state machine that provides specific treatments based upon the state of the device. Each state has an associated module that controls the device to administer an appropriate treatment.

With these and other features of this invention that may become hereinafter apparent, the nature of the invention may be more clearly understood by reference to the following detailed description of the exemplary embodiments, the claims and the several attached drawings.

DETAILED DESCRIPTION OF THE PREFERRED EMBODIMENT

Figure 1:
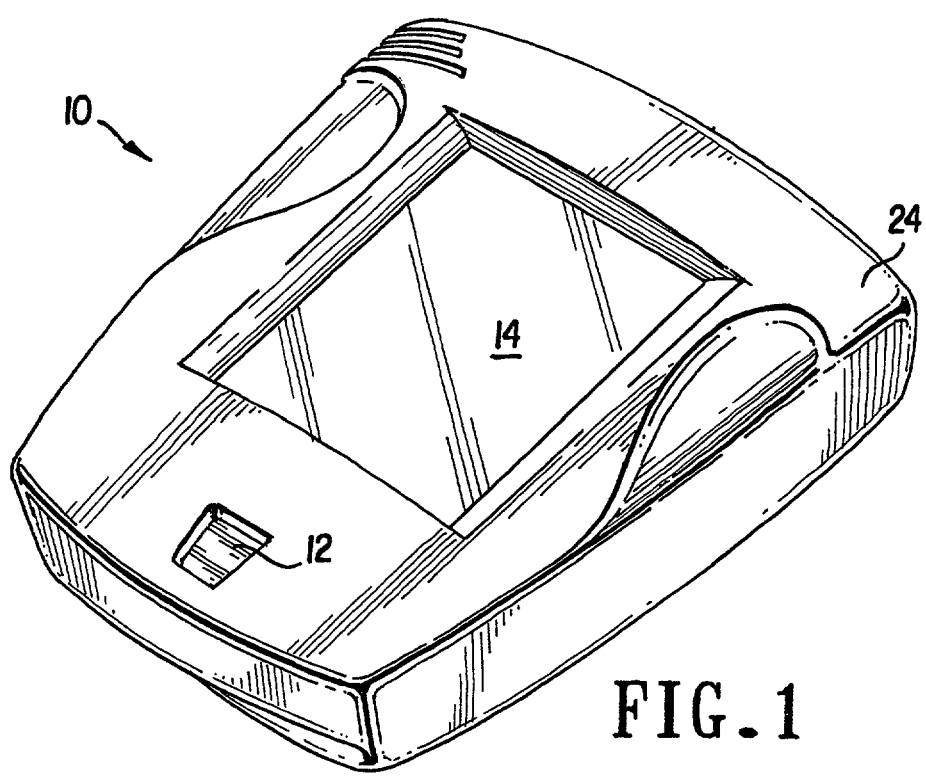
FIG. 1 is a perspective view of an exemplary embodiment of a multi-functional portable electro-medical device in accordance with the present invention.
Figure 2:
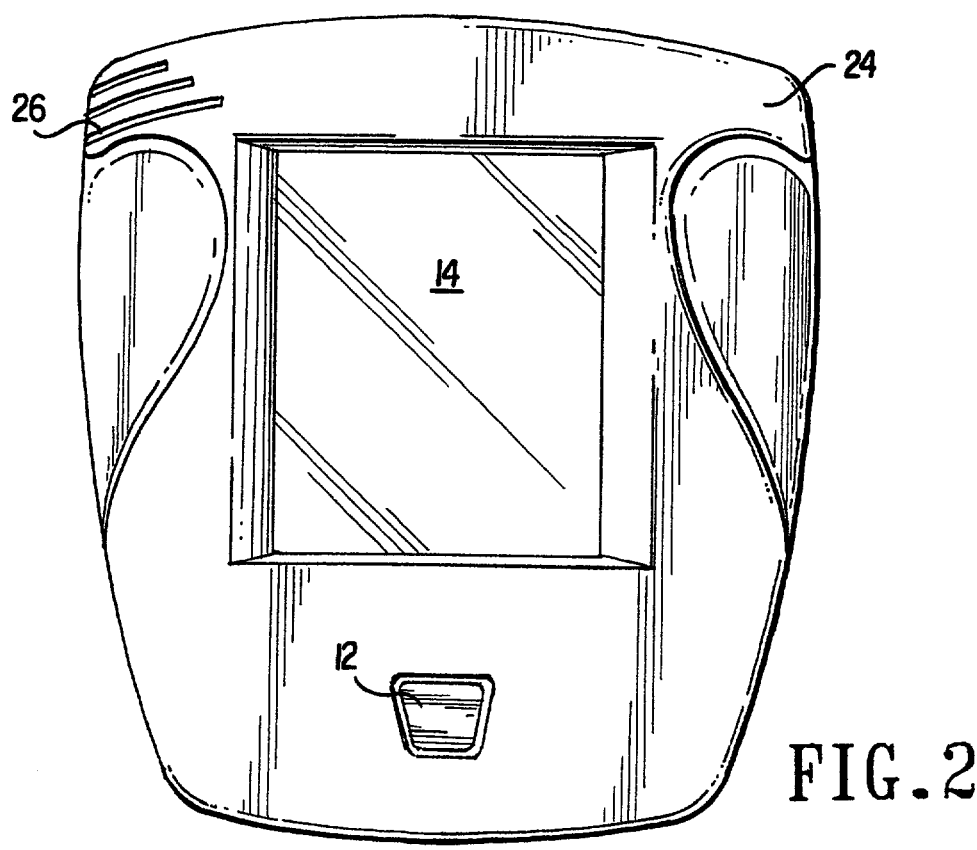
FIG. 2 is a top view of the portable electro-medical device of FIG. 1.

Referring now in detail to the drawings wherein like parts are designated by like reference numerals throughout, FIGS. 1–4 illustrate an exemplary embodiment of the multifunctional portable electro-medical device 10 in accordance with the present invention. The multi-functional portable electro-medical device 10 includes a power switch 12, a liquid crystal display (LCD) touch screen 14 and a speaker 26. Each of the above-described components, as well as other components to be described later herein, may be housed within a plastic case or shell 24.

Figure 3:
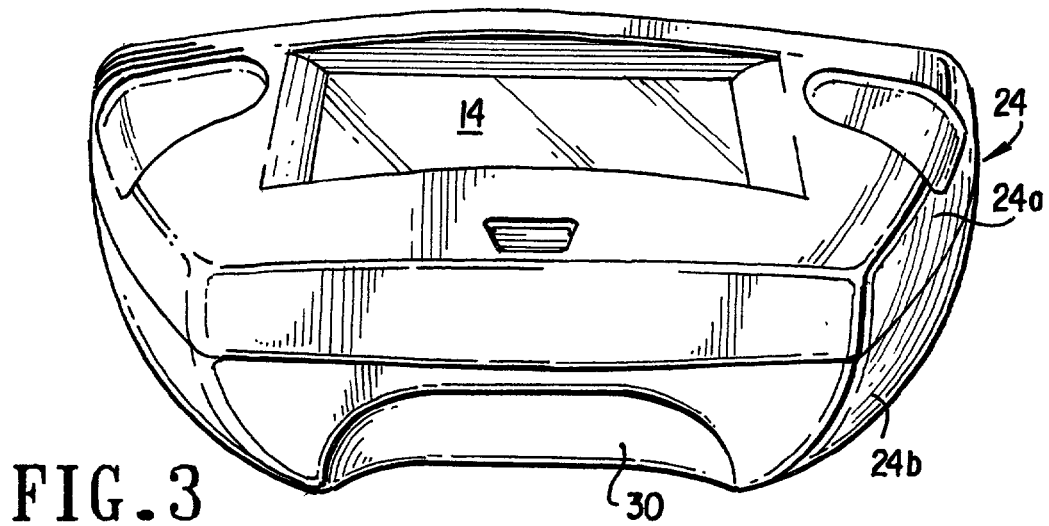
FIG. 3 is a front elevation view of the portable electro-medical device of FIG. 1.
Figure 4:
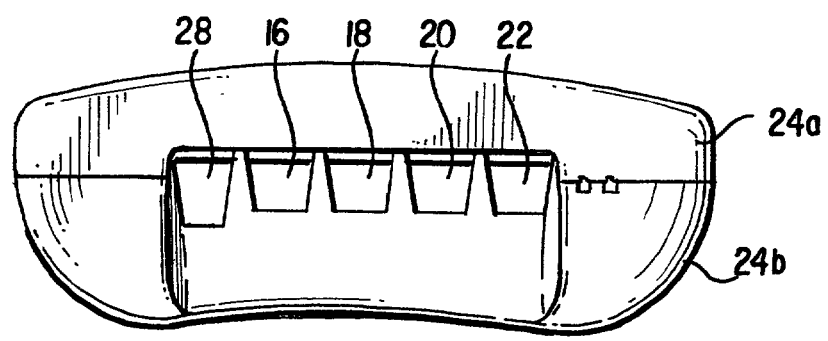
FIG. 4 is a rear elevation view of the multi-functional portable electro-medical device of FIG. 1.

As shown in FIGS. 3 and 4, the case or shell 24 of the exemplary electro-medical device 10 may be formed from an upper piece 24a and a lower piece 24b, in order to more easily manufacture the electro-medical device 10. Four output jacks 16–22 may be provided at the rear of the case of the multi-functional portable electro-medical device 10. The four output jacks 16–22 provide a separate jack for each of the output channels. A jack 28 for connecting the electro-medical device 10 to a battery charger (not shown) may be located on, for example, the rear of the electro-medical device 10.

The electro-medical device 10 may be used in a self-administered manner by patients for providing treatments prescribed by physicians and/or other health care providers. A multi-functional portable electro-medical device in accordance with the present invention may be used for any number of muscle treatments including, without limitation: the relaxation of muscle spasms, the prevention or retardation of muscle disuse atrophy, increasing local blood circulation in the legs or other limbs of the patient, reeducating the leg muscles or other muscles of the patient, providing immediate post-surgical stimulation of calf muscles of the patient in order to prevent venous thrombosis, maintaining or increasing the range of motions of the patient's legs or other limbs, relieving acute pain, the relief and management of chronic pain and for reducing edema and/or inflamation as well as many other treatments.

In order to connect the output jacks 16–22 of the electro-medical device 10 to the patient, a like plurality of cables (not shown) is used to make a connection between one of the output jacks and a standard electrode pad (not shown) which contacts the skin of the patient. For safety purposes, a pin of the cable is inserted into the respective jacks 16–22 in order to connect an electrode pad to the respective output jack 16–22.

The exemplary embodiment of the multi-functional portable electro-medical device 10 of the present invention is a digital device which provides additional safety features for the user, other than those previously described in this section. The electro-medical device 10 provides four isolated channels capable of independently treating four separate muscle groups. Each of the four channels has independent output power stages and transformers in order to provide channel separation. The electro-medical device 10 is battery powered in order to provide portability. The battery power of the exemplary embodiment is provided by an internal 7.2 volt nickel cadmium or nickel metal Hydride battery system, which eliminates the need for patients to monitor and replace batteries. The LCD touch screen 14 provides visual feedback and an interface for the user. In addition, the circuitry of the electro-medical device 10 includes a speaker 26 that provides audible reinforcement of keystroke actions. Also, each of the electrically isolated channels has a separate intensity control for independently increasing and decreasing the intensity of that channel.

The power switch 12, in addition to powering on the electro-medical device 10, also serves as an off switch for shutting down the device. The muscle stimulation mode contract time and relax time, treatment time and normal/alternating mode selections have built-in default settings. The inferential mode, continuous/variable mode selection, frequency setting, pad selection, and treatment times also have default settings. However, those default settings are easily modified at the time of use, in accordance with the prescription or the user's physician's instructions.

An exemplary embodiment of the electro-medical device 10 of the present invention may be provided with a data storage card 30, the details of which are more fully shown and described in U.S. Pat. No. 5,755,745, which is incorporated herein in its entirety. The structure of the storage card 30 is such that it is designed to be used with and removed by the patient from the electro-medical device 10, or any other similar type of Class II device which a patient uses in an unsupervised manner, mailed to a service bureau for downloading the stored usage information, and replaced with a new data storage card. Typically, a data storage card such as the data storage card 30 disclosed herein, is designed to hold 30–60 days of patient usage information. During treatment use by the patient, data is accumulated for the treatment period on the data storage card 30.

Figure 5:
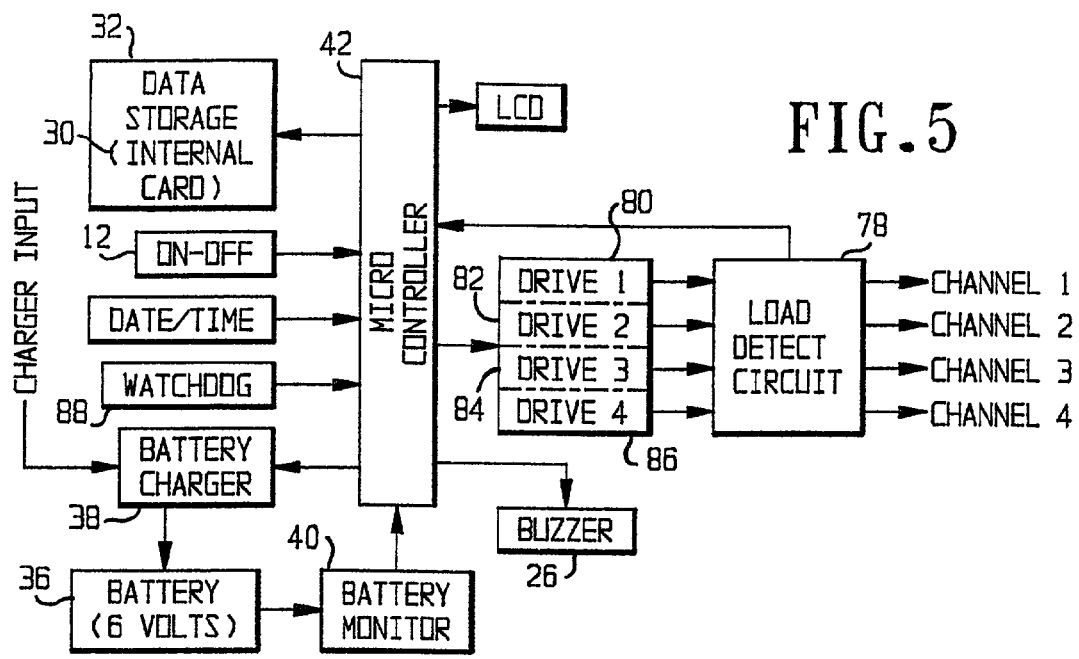
FIG. 5 is a schematic block diagram of an exemplary multi-functional portable electro-medical device in accordance with the present invention.

FIG. 5 is a schematic block diagram of an exemplary embodiment of a multifunctional portable electro-medical device 10 of the present invention. The exemplary electro-medical device 10, as previously discussed, is powered by a rechargeable 7.2 volt nickel cadmium or nickel Hydride battery system 36, which is recharged, by a battery charger 38, which may preferably be powered by standard 110 volt household electric current. As a safety feature, the electro-medical device 10 is designed to be inoperative while the battery system 36 is being charged. A battery monitor circuit 40 is connected between the battery system 36 and the processor 42 so that the processor can provide an indication to the user by means of the LCD 14 under certain adverse battery conditions as will be described later herein. The processor 42, serves to control and monitor all of the functions of the electro-medical device 10.

Figure 6:
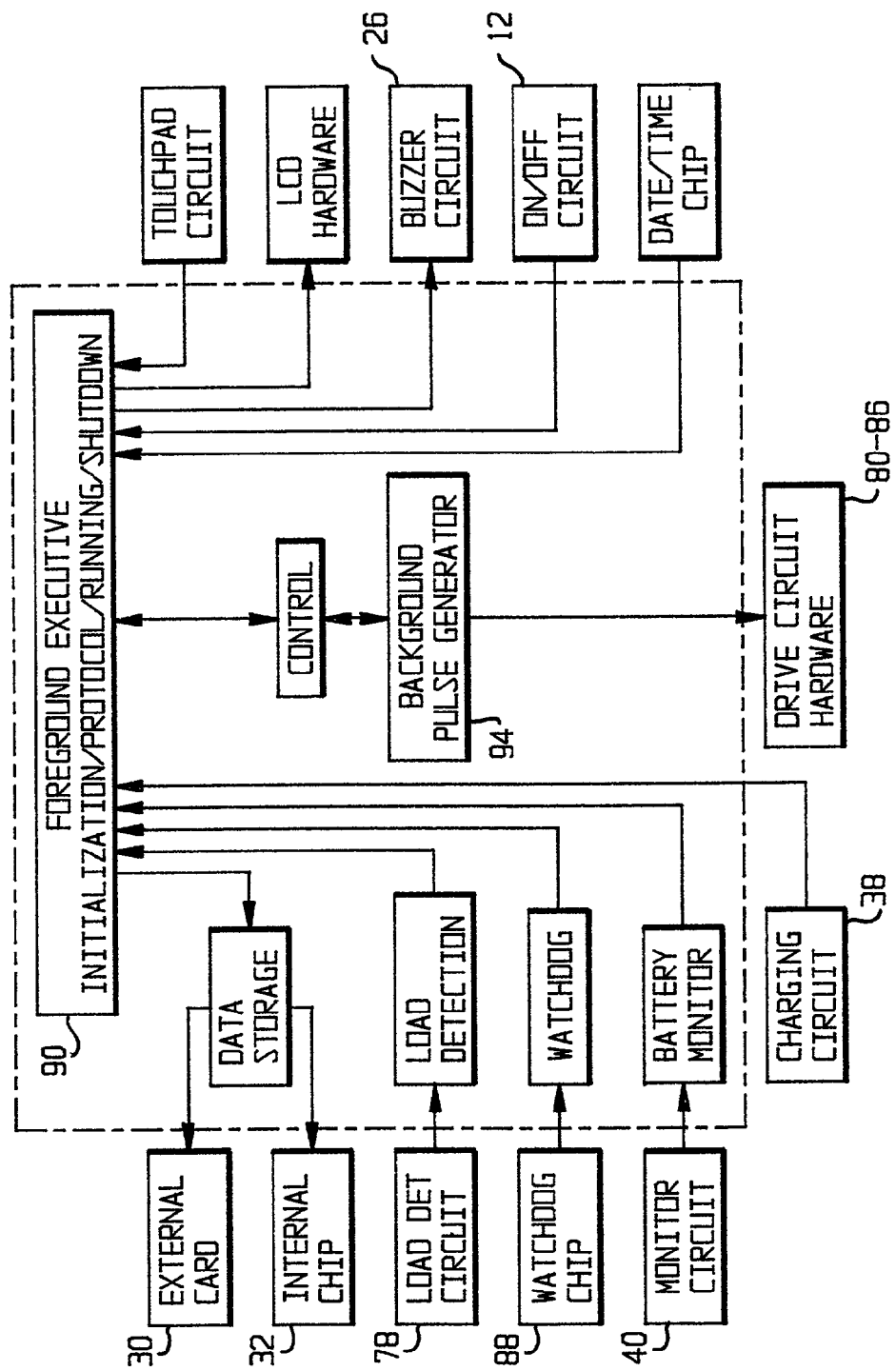
FIG. 6 is a schematic block diagram of an exemplary embodiment of an architecture for a multi-functional portable electro-medical device in accordance with the present invention.

As shown in FIG. 6, the device is preferably implemented with a processor 42. However, the device can also be implemented using a programmed microprocessor and any necessary peripheral integrated circuit elements, an ASIC or other integrated circuit, a hardwired electronic or logic circuit such as a discrete element circuit, a programmable logic device such as a PLD, PLA, FPGA or PAL, or the like. In general, any device that includes a finite state machine which is capable of implementing the flowcharts shown in FIGS. 9–39 can be used to implement the present invention.

An exemplary embodiment of the portable electro-medical device 10 in accordance with the present invention provides four electrically isolated channels 1–4 that are capable of independently treating four separate muscle groups. Each of the four channels has an independent drive system 80–86. Each drive system includes independent output power stages and transformers that ensures channel separation. The processor 42 may be programmed to control the drive circuits 80–86 to provide any type of electro-medical treatment. A speaker 26 provides audible reinforcement to the user of keystroke actions using the LCD touch screen 14. Although this detailed description refers to a device that includes only four channels, it is understood by those of ordinary skill in the art that a device may include any number of channels and still form a part of the invention.

In operation of an exemplary embodiment, the patient first powers up the electro-medical device 10 using the on/off switch 12. If the patient does not desire to change the settings entered into the internal memory 32 of the electro-medical device 10, then the electro-medical device 10 will be powered up in the previously set mode of operation. The default setting is the normal mode. In that normal mode, all four channels of the electro-medical device act synchronously, providing the stimulation pulse trains at the same time, although the intensities of each channel are independently controlled. This mode of operation allows the patient to independently treat up to four separate muscle groups simultaneously.

If the patient desires, an additional level of control for special situations has been provided, which is termed the alternate mode of operation. In the alternate mode of operation, channels 1 and 2 are operated asynchronously with channels 3 and 4. Thus, when channels 1 and 2 are stimulating the muscles, channels 3 and 4 are off, and when channels 1 and 2 are off, channels 3 and 4 are stimulating the muscles. The set on and off times are the same for all four channels in the normal mode.

In the inferential mode of the exemplary embodiment of the invention, the continuous mode of operation has two four pad interferential channels. In the continuous mode, the interference frequency is adjustable from 0 to 200 beats per second. In addition, an amplitude modulation feature is selectable which will reduce the amplitude to 50 percent of the user selected value over a five second period and then return to the user selected value, then repeat the process. In the variable mode of operation, the interference frequency is varied during operation. Three variable modes are provided: a low range of 1–10 beats per second, a high range of 80–150 beats per second and a wide range of 1–150 beats per second. The frequency in all three ranges varies over a ten second period. In both the continuous and variable modes of operation, a pre-mixed two pad mode can be selected. In the two pad mode of operation the interference signals are pre-mixed and then outputted across one cable per channel.

In the pulsed muscle stimulation mode, an exemplary embodiment of the electro-medical device 10 in accordance with the present invention generates an alternating biphasic asymmetric balanced pulse pattern with a cycle frequency of 71 Hz, a 100 volt peak and a 60 milliamp peak. The primary pulse has a maximum width of 415 microseconds, followed by a transformer-coupled exponential decay back to the zero base line. The biphasic pulses alternate direction, resulting in a pulse repetition rate of 142 pulses per second. As previously described, the stimulus intensity is regulated by the patient by pressing the buttons 50. The voltage level is kept constant. The resulting increase or decrease in stimulus intensity is a result of the increasing or decreasing charge per pulse, which is approximately equal to the pulse width times the pulse height. The muscle stimulation pulses are ramped on and off to increase the pulse width to the desired setting and to provide a smooth transition for each muscle contraction.

In the pulsed muscle stimulation mode, a train of repeating pulses is created during the contract cycle. The series of pulses continues until the end of the contract cycle. The relax cycle does not have any pulses. The contract and relax cycles are repeated until the end of the treatment.

In the interferential mode, the exemplary embodiment of the electro-medical device 10 in accordance with the present invention generates a symmetric biphasic sine wave pattern having a carrier frequency of less than 20 KHz, and preferably between about 5–20 KHz. For a carrier frequency of 5000 Hz, an interference frequency is provided of an adjustable 5000–5200 Hz. The output current is 100 milliamps peak to peak on a 500 ohm load. The carrier and interferential signals are true sine wave symmetric biphasic outputs with zero net charge. The two sine waves are mixed in the patient's body when in four-pad mode. In two-pad mode the sine waves are pre-mixed in the electro-medical device and only one pre-mixed output is generated. The sine wave generation continues until the end of the treatment.

The exemplary embodiment of the electro-medical device 10 can be preset to modulate the sine wave outputs. Two types of modulation are provided. The first type of modulation is frequency modulation. Three ranges of modulation can be selected: 1–10 beats per second, 80–150 beats per second, and 1–150 beats per second.

The second type of modulation, amplitude modulation, can be selected when the interference frequency is held constant. This type of modulation varies the amplitude of one output from its preset value downward to 50 percent of its preset value over a five second period. The amplitude then returns to its preset value over another five second period. This same amplitude modulation is then repeated for the other output and the process is continuously repeated. Further to the preferred embodiment, each channel is connected to two pads and the channels are configured so that the modulation on a first channel is opposite to the modulation on the second channel. That is, as the amplitude on the first channel is decreased downward, the amplitude on the second channel returns to the preset value. Amplitude modulation can be performed in both the normal mode and the alternate mode of operation.

The load detect circuit 78 shown in FIG. 5 of the exemplary embodiment may consist of an output voltage signal which is measured across a known load resistance. That signal is amplified and fed back into the analog-to-digital conversion system contained within the processor 42, which allows a precise measurement of the actual load experienced across the output of the transformer contained in each of the four drive circuits 80–86. That measurement allows the processor 42 to detect both open circuits (that is, no load conditions) and short circuit conditions, which allows the processor 42 to shut down the control signals going to the pulse generation circuits which form part of the drive circuits 80–86. Thus, under open or short circuit conditions, the load detection circuit 78 operates to shut down the generation of pulses by the electro-medical device 10.

A watchdog system 88 is also provided to the exemplary embodiment to monitor the processor 42 to ensure that the processor 42 is operating and issuing instructions. The watchdog system 88 operates using a "counter". If the "counter" reaches a certain predetermined value, then it operates to shut down the processor 42 and thus the electro-medical device 10. During normal operation, the processor 42 prevents such a shut down from occurring by always resetting the "counter" of the watchdog system 88 back to zero well before the maximum counter value is reached. In that manner, if the processor 42 becomes non-operational for any reason, the counter of the watchdog system 88 would reach the maximum predetermined value and, thus, shut down the electro-medical device 10.

FIG. 6 shows a schematic block diagram of an exemplary embodiment of an architecture for an electro-medical device in accordance with the present invention. FIG. 6 illustrates the interfaces between the hardware modules and the control routine modules. The primary module is the foreground executive module 90. The foreground executive module 90 provides executive control of the device from startup to shutdown. That exemplary module is programmed as a state machine with the control routine controlling the operational state of the device based upon inputs received from the device hardware.

Figure 7:
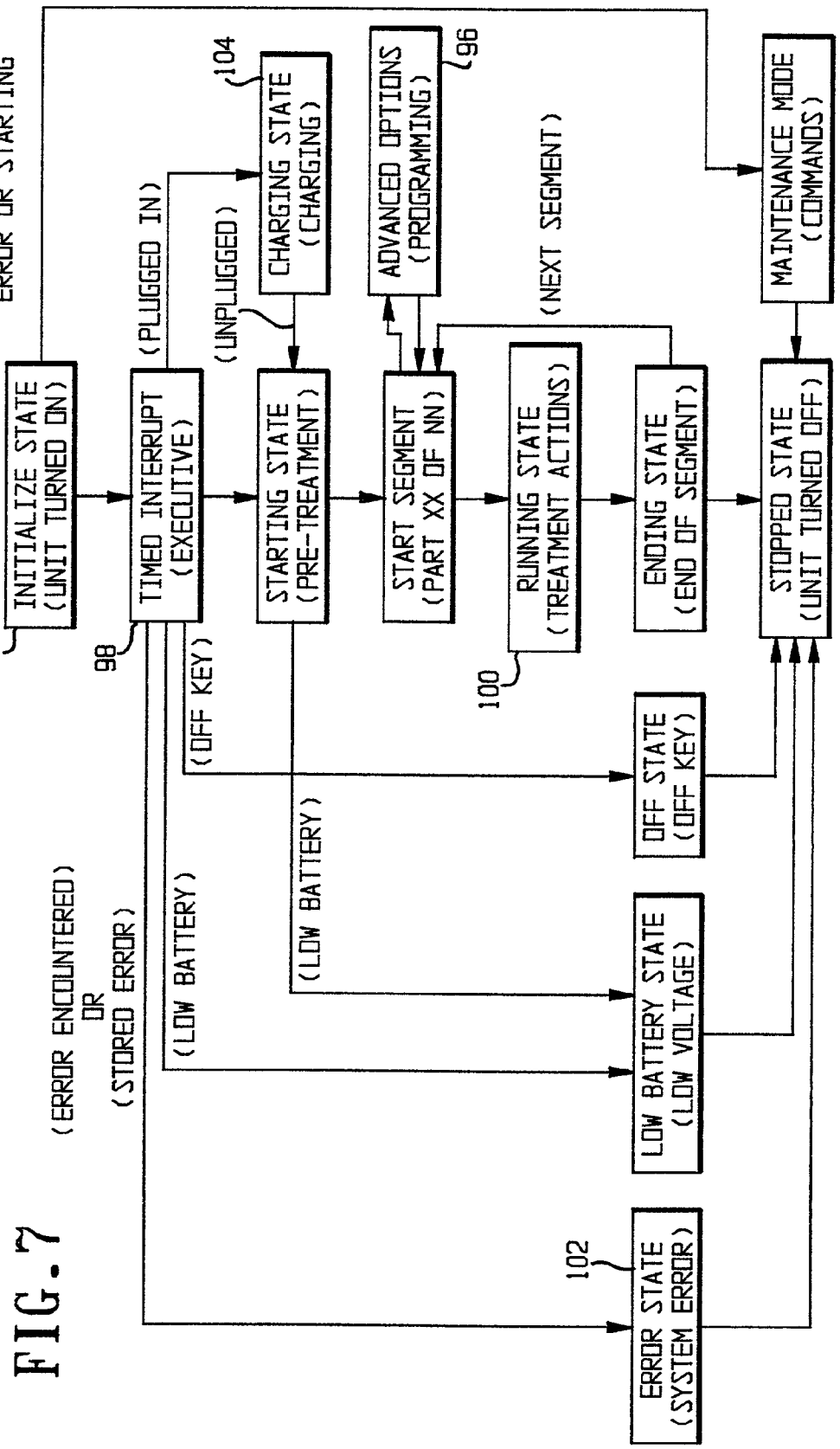
FIG. 7 is a state diagram showing the operation of an exemplary control routine of an multi-functional portable electro-medical device in accordance with the present invention.

FIG. 7 shows a state diagram of the exemplary control routines shown in FIGS. 9–39 of an electro-medical device 10 in accordance with the present invention. Those control routines that correspond to each state will be described in detail later herein. The primary module that operates the output channel circuits in the pulsed muscle stimulation mode is the background pulse generator module 94. That module is started by the foreground executive module 90 at startup and is an independent interrupt driven module 98 that functions using data supplied by the foreground executive module 90. The foreground executive module 90 and the real time clock operational frequencies are constantly monitored against each other to ensure that they do not become out of tolerance. If they become out of tolerance, the electro-medical device 10 shuts down all operation.

The exemplary control routine also monitors the loads on each channel and will shut down the output to a channel with a "no load" detection. The control routine also monitors the battery and shuts down the operation before there is insufficient power to operate the processor 42.

The exemplary control routine also accumulates the treatment data for each channel during a treatment session. When the treatment session is complete, the control routine writes this data to the internal data storage 36 prior to shutdown of the processor. This data is also stored on the data card 30 by transferring the data from the internal data storage to the data card during the shutdown sequence.

As previously described, the primary module which operates the output channel circuits is the pulse generator module, which forms part of the drive circuits 80–86. That module is started by the foreground executive module 90 at the initialize state 92, when the power switch 12 is depressed. The background pulse generator module 94 is operated in an independent interrupt driven fashion and functions using data supplied by the foreground executive module 90, which data has been inputted during the advanced options or programming state 96.

The battery system 36 of the exemplary embodiment is charged during a quick recharge cycle by the battery charger 38. During the charging cycle, the electro-medical device is in the charging state 104, and cannot operate. The battery monitor 40 as well as the processor 42 determine the amount of charge needed by the battery system 36. If the battery system 36 is sufficiently low, then the battery system will be charged until the battery voltage begins to show a decline, then the charging circuit reverts to a "trickle" charge mode in order to allow maintenance of a fully charged battery at all times.

An exemplary embodiment control routine of the electro-medical device 10 in accordance with the present invention also includes, as a safety feature, a start treatment channel setting. That feature is designed to prevent, at the start of a treatment, a channel output to be set above zero. That assures that the user will not receive an abrupt muscle contraction when starting a treatment. Thus, when starting a treatment, the electro-medical device 10 begins operation with all channel intensity settings at zero. If a pad is removed from the skin during treatment, the electro-medical device 10 automatically resets the channel to zero. If a pad cable is unplugged from the electro-medical device 10 during treatment, the intensity of that channel is reset to zero.

In addition to the start treatment channel setting safety feature, the exemplary embodiment of the electro-medical device 10 in accordance with the present invention also includes a channel increase/decrease limit feature, which is designed so that the channel output level can only be changed one digit at a time. Thus, pressing the respective channel button 50 will change the output controlled by that button by only a small increment. That assures that the user will not receive a rapid increase or decrease in muscle contraction during treatment if the button were continually depressed.

Another exemplary embodiment of the electro-medical device 10 in accordance with the present invention also includes a monitor which is designed to constantly monitor the frequency and width of the waveform being applied to each of the pad cables. If the waveform changes from the pattern that it is designed to generate, the electro-medical device is automatically shut-off. That assures that the user will receive the effective and comfortable treatment which is designed to be provided by the electro-medical device 10.

The patient receives a constant and accurate display of information concerning the operation of the electro-medical device 10. When the electro-medical device 10 is first turned on using the switch 12, the LCD 14 displays the default settings for each of the contract time, relax time, mode and treatment time. If those are the prescription settings for the particular patient using that electro-medical device 10, then there is no need to change the settings. Otherwise, the settings are changed as is described herein below.

Figure 8A:
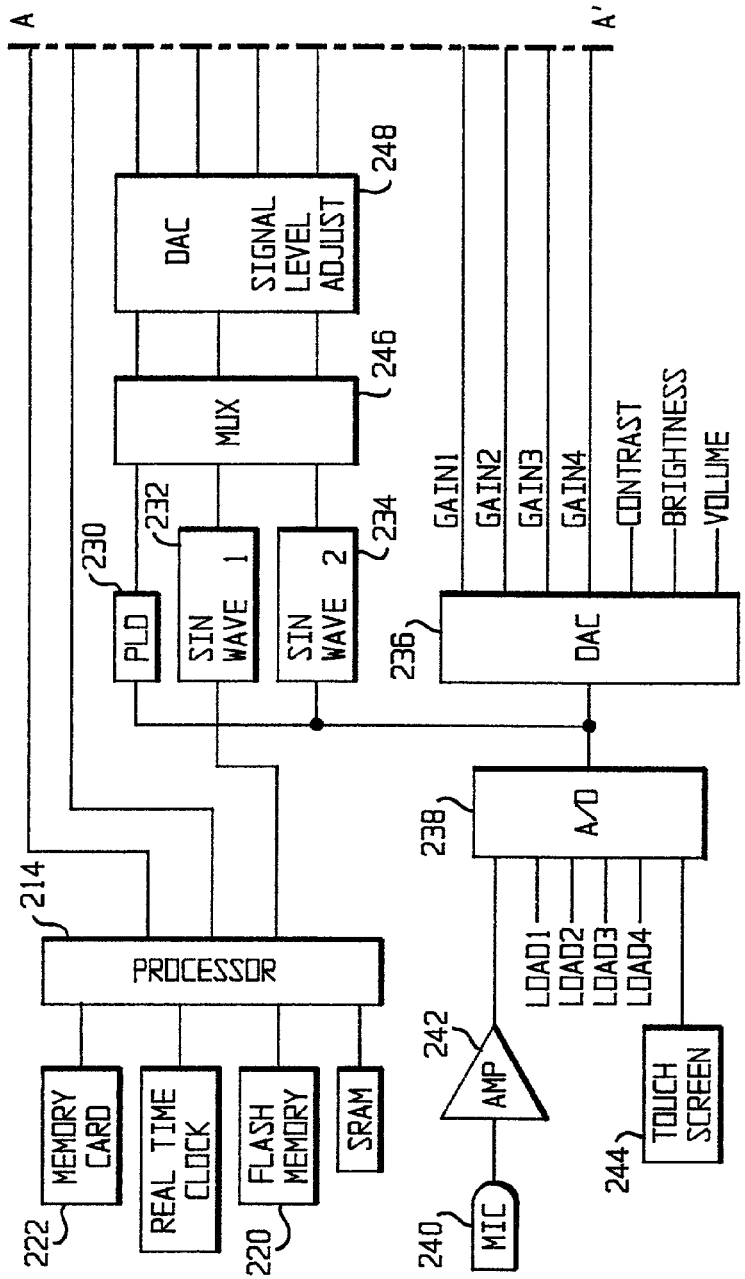
FIGS. 8A and 8B show a schematic diagram of a circuit for an exemplary embodiment of a multi-functional portable electro-medical device in accordance with the present invention.
Figure 8B:
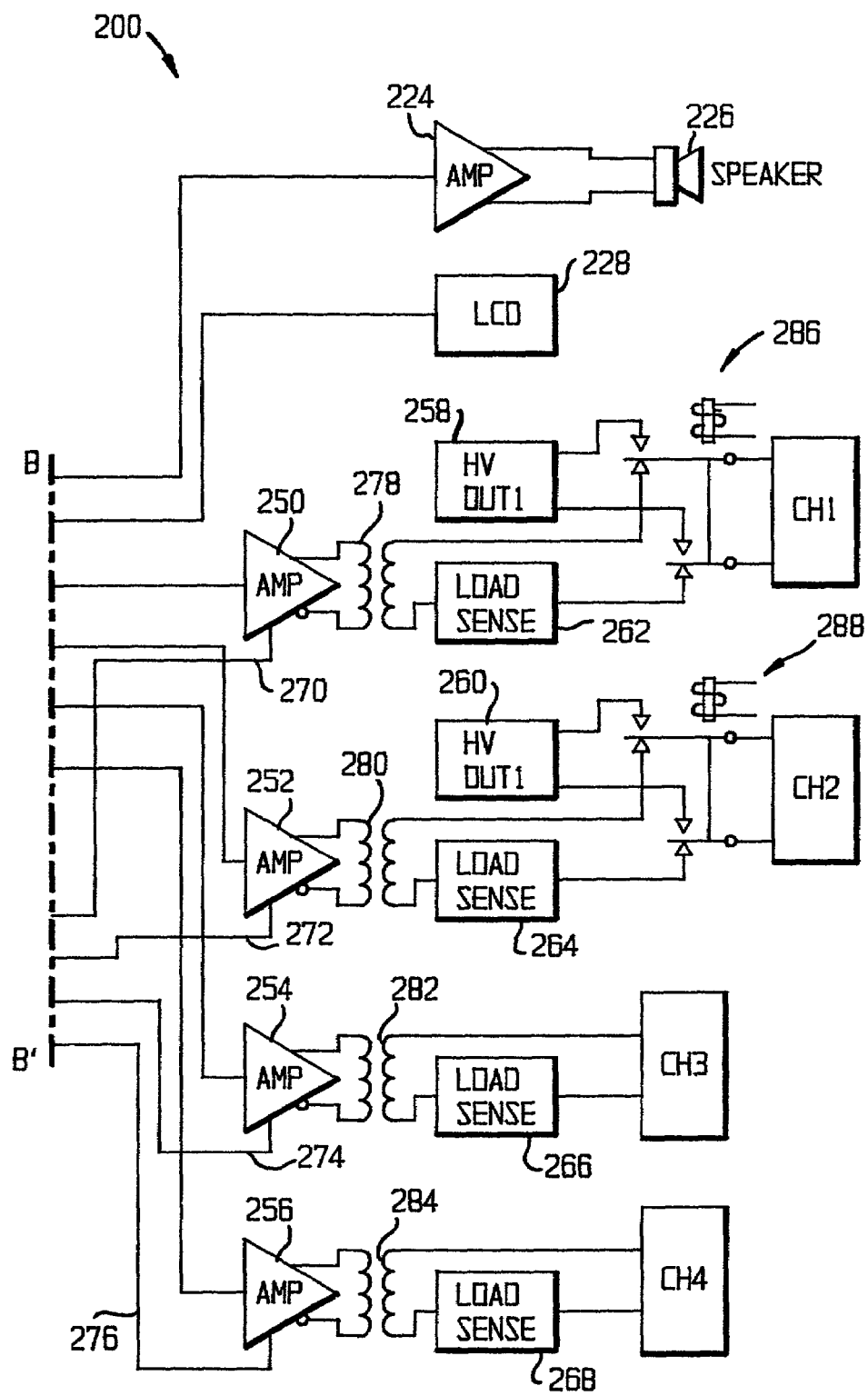

FIGS. 8A and 8B show a schematic diagram of the circuit for an exemplary embodiment of a multi-functional electro-medical device in accordance with the present invention. The circuit 200 includes a power circuit 204 that has a charger connector 206 in communication with a battery charger 208 in communication with a power supply 210. The power circuit 204 provides a number of outputs 212 that provide power to other portions of the electro-medical device.

The circuit 200 also includes a processor 214 in communication with static RAM 216, flash memory 218, a realtime clock 220, and a memory card 222. The processor 214 may be any type of processor that is capable of executing the control routine as set forth in the flow charts of FIGS. 9–39. The processor 214 is in communication with an amplifier 242 that controls a speaker 226, a liquid crystal display 228, a programmable logic device 230, sine wave generators 232 and 234, a digital to analog converter 236 and an analog to digital converter 238. The A to D converter 238 is in communication with a microphone 240 through the amplifier 242 and a touch screen 244. The digital to analog converter provides an output gain 270, 272, 274, 276 to four channels. The processor 214 controls the digital to analog converter 236 to output a predetermined maximum voltage on those outputs. The outputs 270, 272, 274 and 276 provide the input for the amplifiers 250, 252, 254 and 256, respectively.

The processor 214 also communicates with a programmable logic device 230 and sine wave generators 232 and 234 which are multiplexed by a multiplexer 246 to a digital to analog converter 248. The digital to analog converter 248 adjusts the signal level of the amplifiers 250, 252, 254 and 256. The amplifiers 250, 252, 254 and 256 communicate through transformers 278, 280, 282 and 284, respectively. The output of the transformers 282 and 284 are provided directly to the output of channels three and four, respectively. However, the outputs of transformers 278 and 280 are switched through switches 286 and 288 to output channels one and two, respectively. The switches 286 and 288 are solenoids which activate dual bar switches to select the outputs from the transformers 278 and 280 from the high voltage outputs 258 and 260. The circuit 200 also includes load sensing devices 262, 264, 266 and 268 which sense the load of corresponding channels one through four, respectively.

Figure 9:
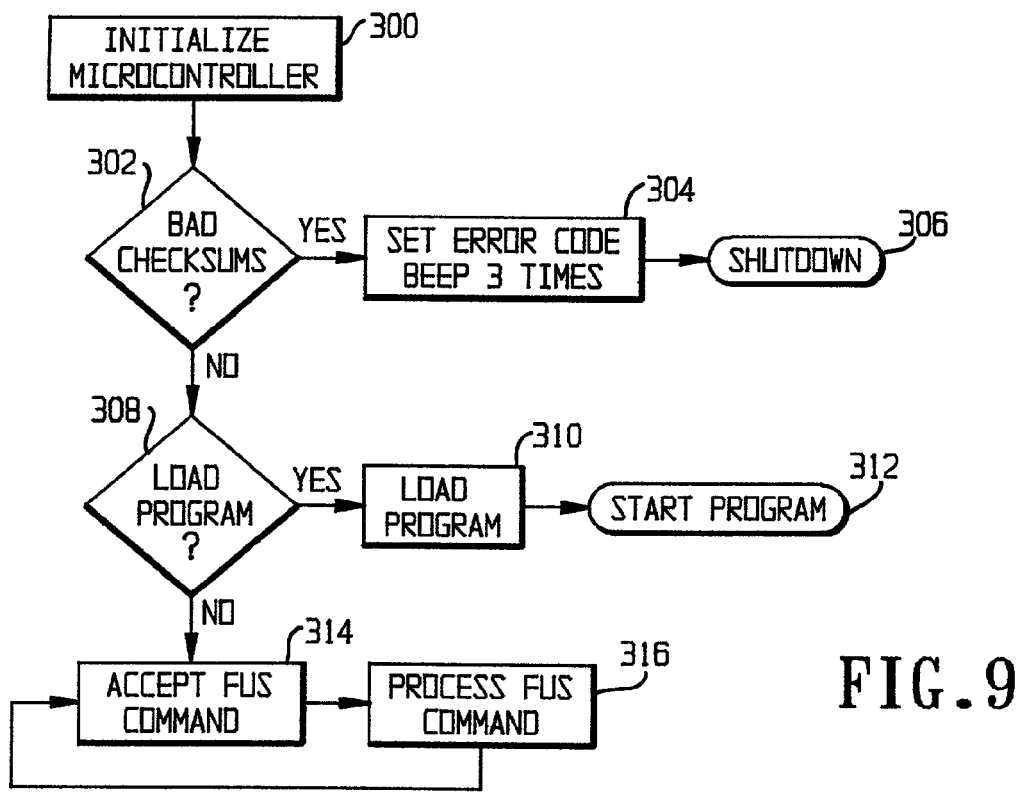

FIG. 9 outlines a control routine for a field upgrade of a system of an exemplary embodiment of the device of the present invention. The control routine of FIG. 9 executes each time the device powers-up. Upon power-up, the control routine starts at step 300 where the control routine initializes the processor. The control routine then continues to step 302 where the control routine determines whether there are bad check sums. If, in step 302, the control routine determines that there are bad check sums, then the control routine continues to step 304. In step 304, the control routine sets an error code, beeps three times and continues to step 306. In step 306, the control routine shuts down the device. If, in step 302, the control routine determines that there are no bad check sums, then the control routine continues to step 308. In step 308, the control routine determines whether the program in the static RAM 216 is to be loaded based upon a special byte in the serial port that indicates that a field upgrade whether a field upgrade is to take place. If, in step 308, the control routine determines that the serial port indicates is not to take place, then the control routine continues to step 310. In step 310, the control routine loads a program that is stored in the static RAM 216 and continues to step 312. In step 312, the control routine executes the control routine outlined in the flowchart of FIG. 10.

If, however, in step 308, the control routine determines that a field upgrade is to take place, then the control routine continues to step 314. In step 314, the control routine accepts a field upgrade system command and continues to step 316. In step 316, the control routine processes the field upgrade system command and returns to step 314. The field upgrade system command may include a command to shutdown the device. In that manner, steps 308, 314 and 316 operate as a type of "boot loader" that enables the program in the static RAM to be modified.

Figure 10:
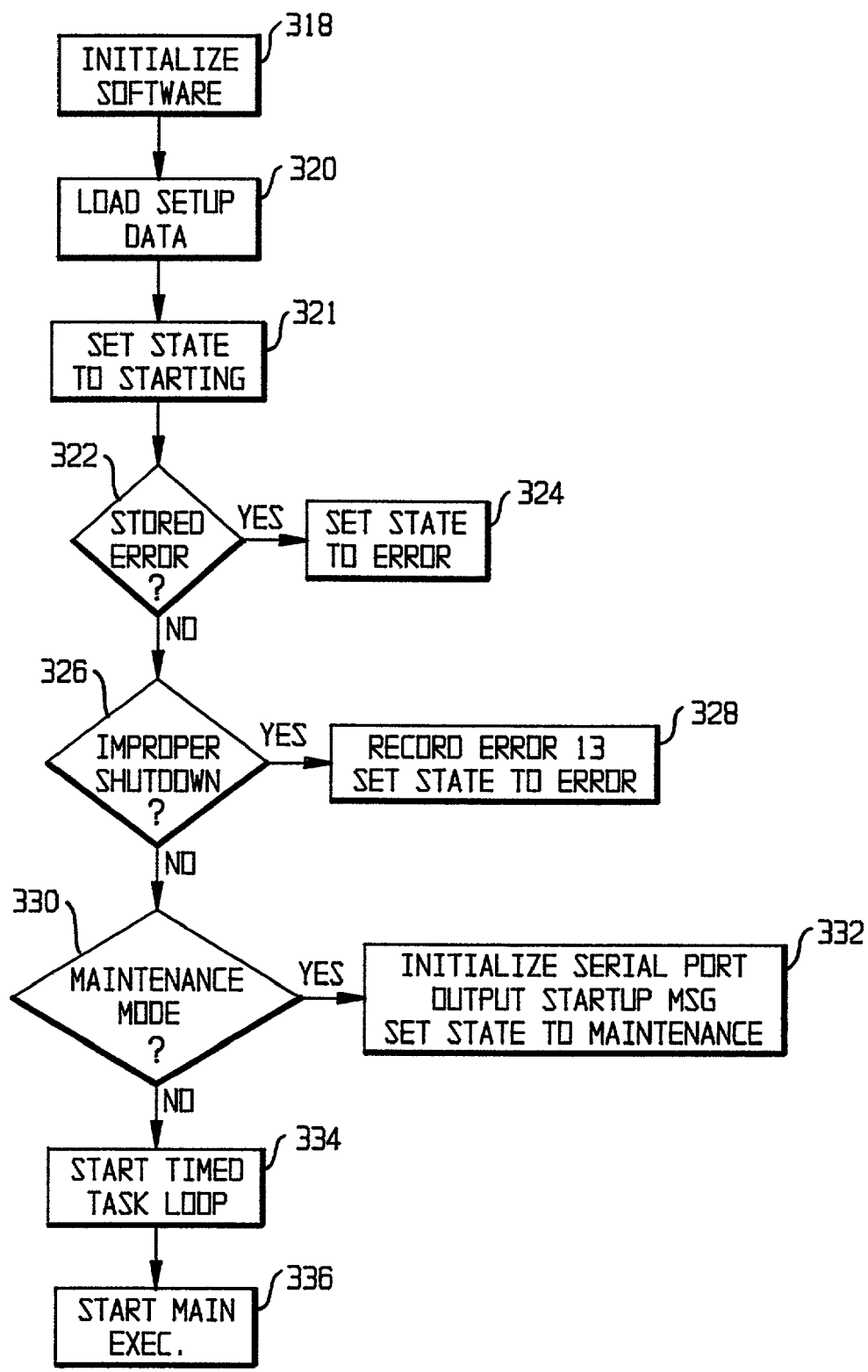

FIG. 10 shows a flowchart for an initialization control routine of an exemplary device in accordance with the present invention as called from step 312 in FIG. 9. The control routine starts at step 318 where the control routine initializes the hardware and continues to S320. In step 320, the control routine loads the setup data from an internal flash memory and continues to step 321. In step 321, the control routine sets the state of the device to "starting" and continues to step 322. In step 322, the control routine determines whether an error has been stored. If, in step 322, the control routine determines that an error has been stored, then the control routine continues to step 324. In step 324, the control routine sets the state to "error" and continues to step 326. If, however, in step 322, the controller determines that an error has not been stored, then the control routine continues to step 326. In step 326, the control routine determines whether the device has had an improper shut down. If, in step 326, the control routine determines that the device has experienced an improper shut down, then the control routine continues to S328. In step 328, the control routine records error 13, sets the state of the device to "error" and returns to step 330. If, however, in step 326, the control routine determines that the device has not experienced an improper shut down, then the control routine continues to step 330.

In step 330, the control routine determines whether the device is in maintenance mode. If, in step 330, the control routine determines that the device is in maintenance mode, then the control routine continues to step 332. In step 332, the control routine initializes a serial port output start up message, sets the state of the device to "maintenance" and continues to step 334. If, however, in step 330, the control routine determines that the device is not in the maintenance mode, then the control routine continues to step 334. In step 334, the control routine starts a timed task loop. A timed task loop is a control loop for tasks that must be executed at specified time intervals. An example of such a timed task loop includes updating a time indication bar upon the touch screen The control routine then continues to step 336. In step 336, the control routine executes the main executive flow chart as shown in FIG. 11.

Figure 11:
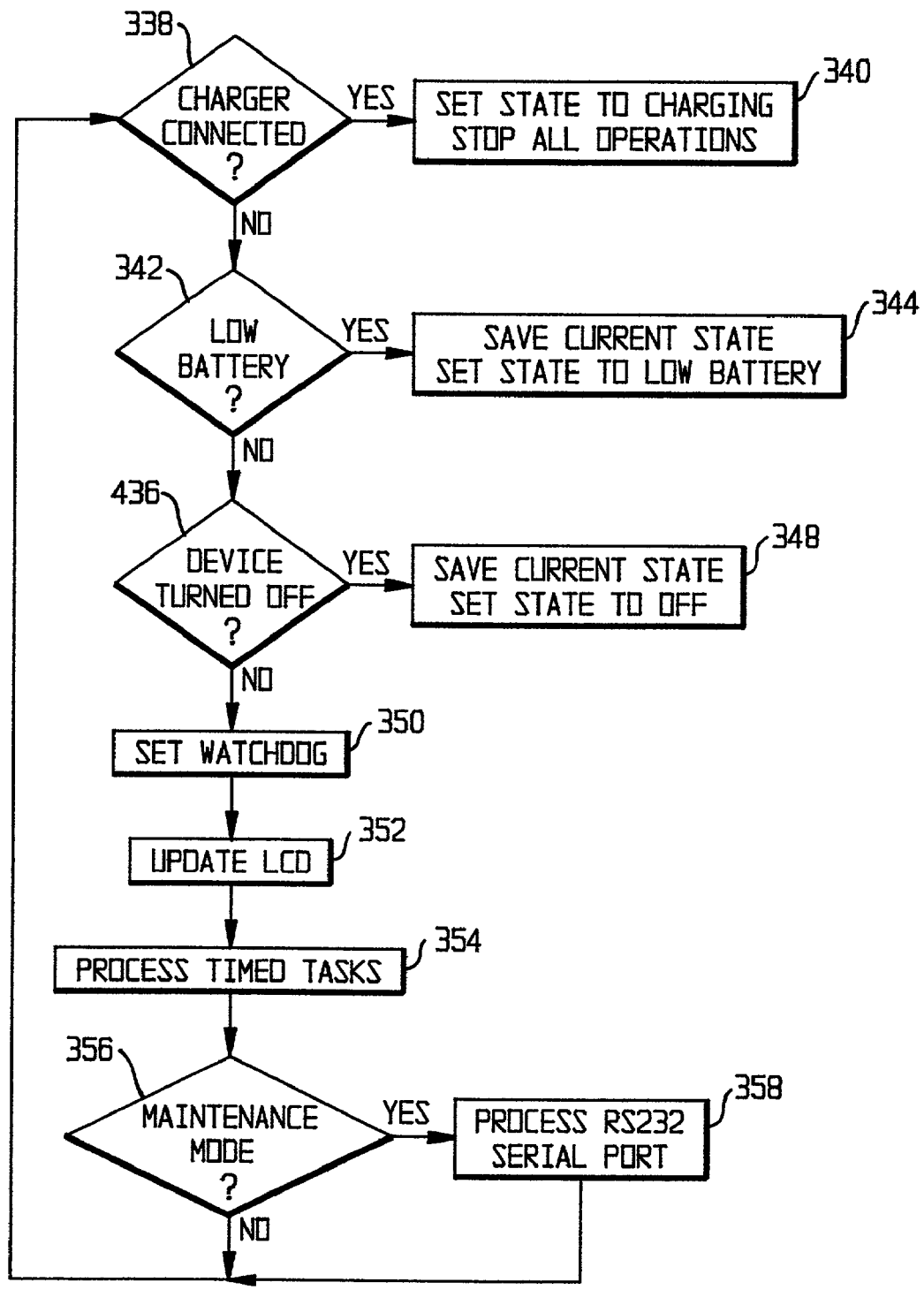

FIG. 11 shows a main executive control routine of an exemplary device in accordance with the present invention. The control routine starts at step 338 where the control routine determines whether the charger is connected. If, in step 338, the control routine determines that the charger is connected, then the control routine continues to step 340. In step 340, the control routine sets the state of the device to "charging," stops all operations and continues to step 342. If, however, in step 338, the control routine determines that the charger is not connected, then the control routine continues to step 342. In step 342, the control routine determines whether the battery has a low charge. If, in step 342, the control routine determines that the battery has a low charge, then the control routine continues to step 344. In step 344, the control routine saves the current state, sets the state of the device to "low battery" and continues to step 346. If, however, in step 342, the control routine determines that the battery does not have a low charge, then the control routine continues to step 346.

In step 346, the control routine determines whether the device has been turned off. If, in step 346, control routine determines that the device has been turned off, then the control routine continues to step 348. In step 348, the control routine saves the current state, sets the state of the device to "off" and continues to step 350. If, however, in step 346, the control routine determines that the device has not been turned off, then the control routine continues to step 350. In step 350, the control routine resets the counter of the watchdog and continues to step 352. In step 352, the control routine updates the liquid crystal display 14 and continues to step 354. In step 354, the control routine processes the timed tasks that were started in step 334 of FIG. 10 and continues to step 356. In step 356, the control routine determines whether a byte in the data card is set to "maintenance mode." If, in step 356, the control routine determines that the byte is set to "maintenance mode," then the control routine continues to step 358. In step 358, the control routine processes the data received in the RS232 serial port as set forth in the control routine of FIG. 31 and returns to step 338. If, however, in step 356, the control routine determines that the "maintenance mode" button has not been touched, then the control routine returns to step 338.

Figures 12, 13, 14, 15:
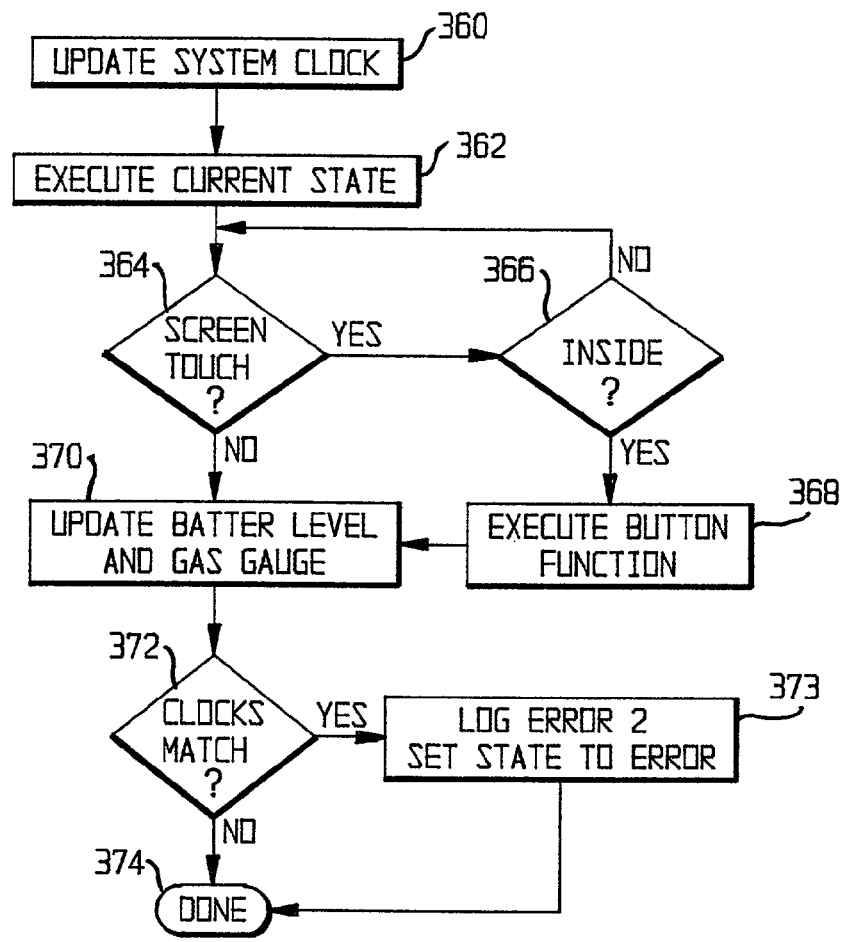

FIG. 12 outlines the executive interrupt control routine of an exemplary embodiment of the device according to the present invention. The exemplary embodiment of the device operates by continuously processing the control routine outlined in the flowchart of FIG. 11. However, the control routine of FIG. 11 may be interrupted upon a predetermined schedule e.g. every ¹⁄₁₀ of a second, to execute the control routine outlined in the flowchart of FIG. 12. Similarly, FIGS. 13–15 show other interrupts to the control routine of FIG. 11.

The control routine of FIG. 12 starts at step 360 where the control routine updates the system clock and continues to step 362. In step 362, the control routine executes the control routine that corresponds with the current state. Examples of such control routines are shown in FIGS. 16–39 and are described in detail below. After the appropriate state control routine is executed, control of the device returns to the control routine of FIG. 12 where the control routine continues to step 364. In step 364, the control routine determines whether the screen has been touched. If, in step 364, the control routine determines that the screen has been touched, then the control routine continues to step 366. In step 366, the control routine determines whether the screen has been touched at a position that corresponds to the inside of a button on the screen to determine whether a button has been touched on the touch screen. If, in step 366, the control routine determines that a button has not been touched, then the control routine returns to step 364. If, in step 366, the control routine determines that a button has been touched on the screen, then the control routine continues to step 368. In step 368, the control routine executes the function of the button that has been touched and continues to step 370.

If, however, in step 364, the control routine determines that the screen has not been touched, then the control routine continues to step 370. In step 370, the control routine updates the battery level and the gas gauge on the display and continues to step 372. In step 372, the control routine determines whether the foreground executive and real time clocks match. If, in step 372, the control routine determines that the clocks do not match, the control routine continues to step 373. In step 373, the control routine, logs error "2," sets the state of the device to "error" and continues to step 374. If, however, in step 372, the control routine determines that the clocks do match, then the control routine continues to step 374. In step 374, the control routine returns to continue processing of the control routine that is outlined in FIG. 11.

FIGS. 13–15 outline control routines that generate pulses, receive/send characters and process a transmission, respectively. As explained above, each of the control routines of FIGS. 13–15 interrupts execution of the control routine outlined in the flow chart of FIG. 11 and executes at a predetermined schedule. After the control routine is completed, control of the device is returned to the control routine that is outlined in the flowchart of FIG. 11.

Figure 16A:
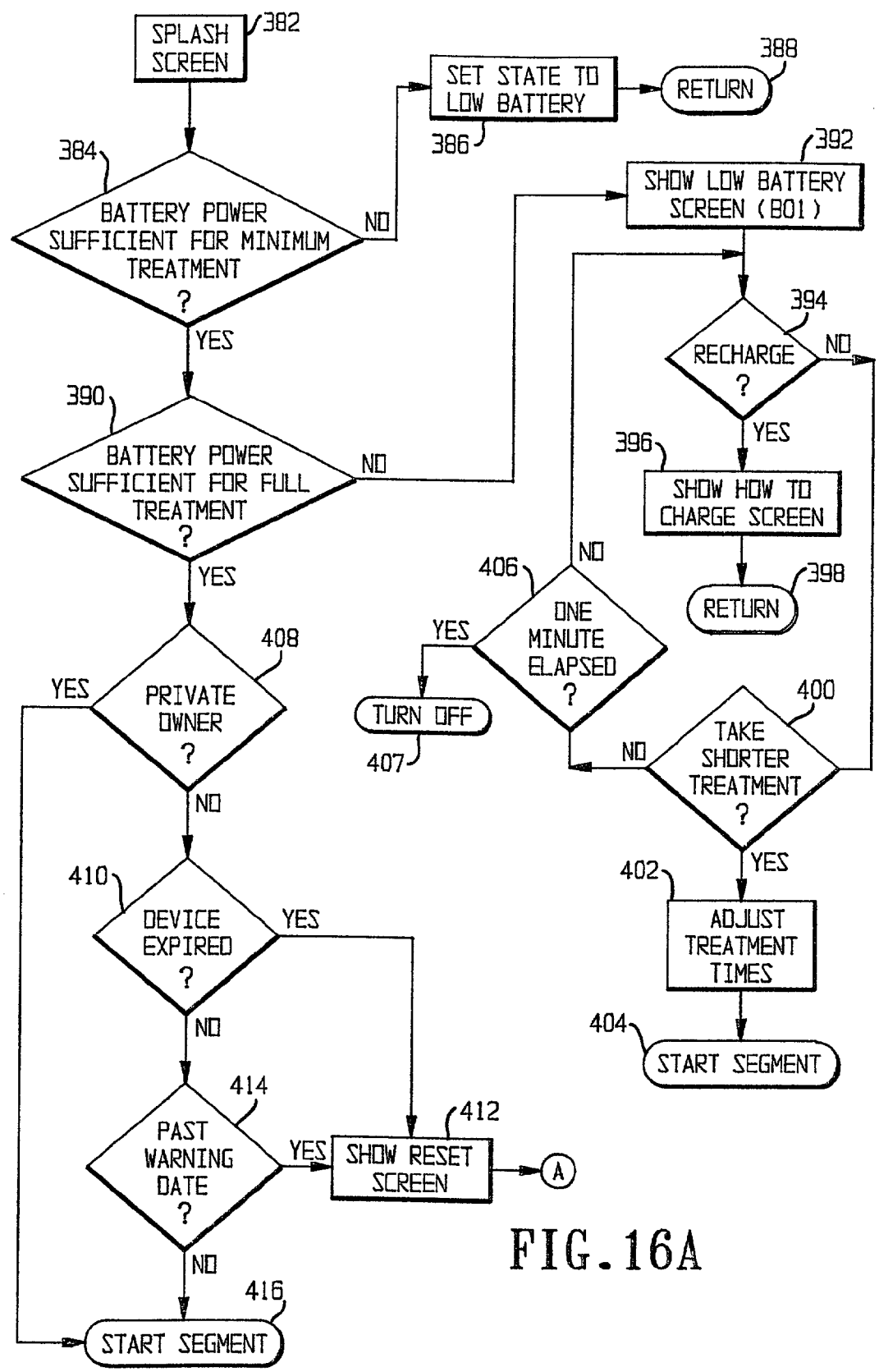
Figure 16B:
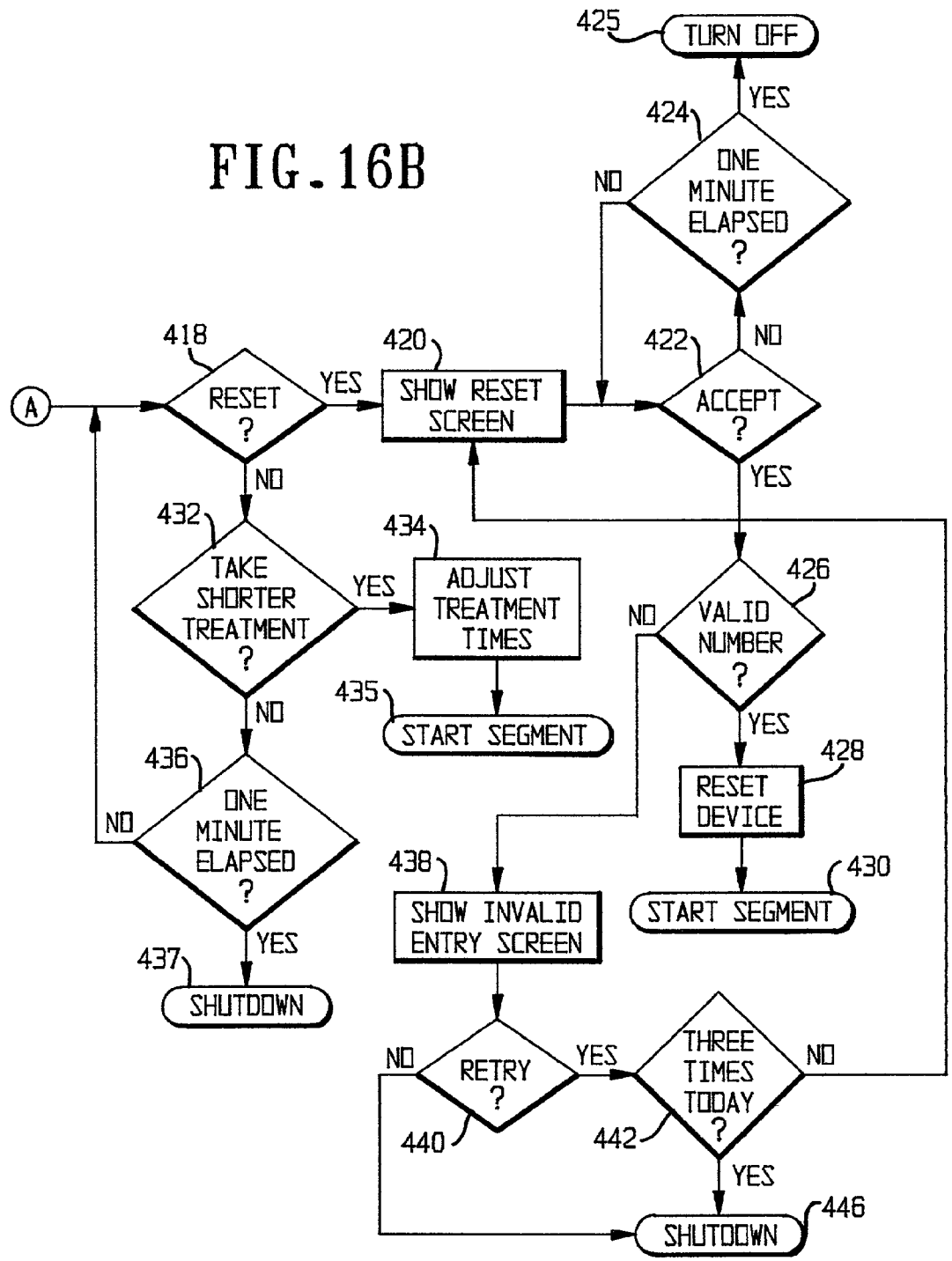

FIG. 16 outlines the "starting" state control routine in accordance with an exemplary embodiment of the present invention. The control routine starts at step 382 where the control routine displays the "splash" screen shown in FIG. 39.5 and continues to step 384. In step 384, the control routine determines whether the battery power is sufficient to provide a minimum treatment. If, in step 384, the control routine determines that the battery power is not sufficient to provide a minimum treatment, then the control routine continues to step 386. In step 386, the control routine sets the state of the device to "low battery" and continues to step 388. In step 388, the control routine returns control of the device to the control routine of FIG. 12.

Figure 40:
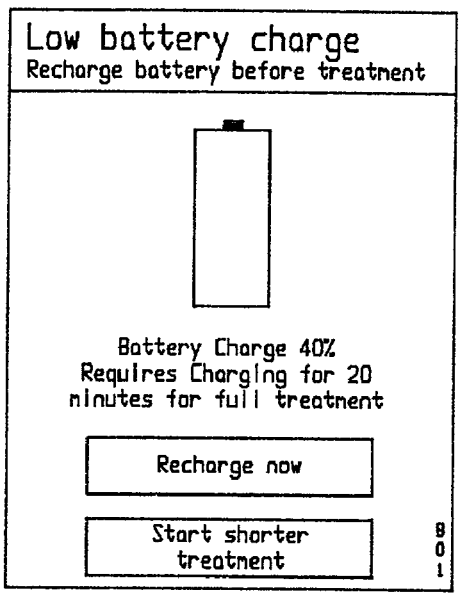
FIGS. 40–150 show exemplary display screens of a multi-functional portable electro-medical device in accordance with the present invention.
Figure 41:
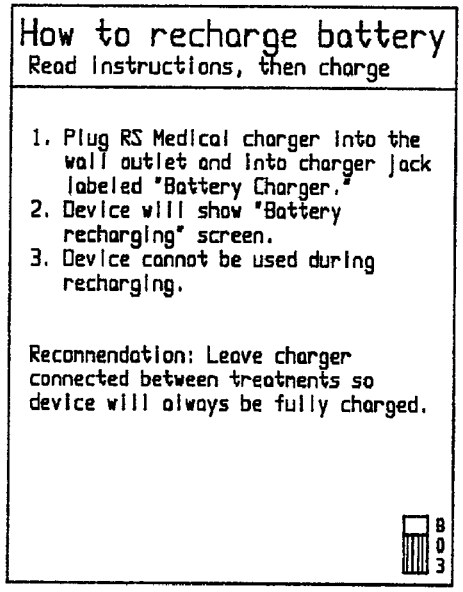

If, however, in step 384, the control routine determines that the battery power is sufficient to provide a minimum treatment, then the control routine continues to step 390. In step 390, the control routine determines whether the battery power is sufficient to provide a full treatment. If, in step 390, the control routine determines that the battery power is not sufficient to provide a full treatment, then the control routine continues to step 392. In step 392, the control routine displays the "low battery charge" screen, an example of which is shown in FIG. 40, and continues to step 394. In step 394, the control routine determines whether the "recharge now" button has been touched. If, in step 394, the control routine determines that the "recharge now" button has been touched, then the control routine continues to step 396. In step 396, the control routine displays a "how to recharge battery" screen, an example of which is shown in FIG. 41 and continues to step 398. In step 398, the control routine returns control of the device to the control routine outlined in FIG. 12.

If, however, in step 394, the control routine determines that the "recharge now" button has not been touched, then the control routine continues to step 400. In step 400, the control routine determines whether the "start shorter treatment" button has been touched. If, in step 400, the control routine determines that the "start shorter treatment" button has been touched, then the control routine continues to step 402. In step 402, the control routine executes the control routine outlined in FIG. 21 and continues to step 404. In step 404, the control routine starts the segment by executing the control routine outlined in FIG. 17. If, however, in step 400, the control routine determines that the "start shorter treatment" button has not been touched, then the control routine continues to step 406. In step 406, the control routine determines whether one minute has elapsed. If, in step 406, the control routine determines that one minute has not elapsed, then the control routine returns to step 394. If, however, in step 406, the control routine determines that one minute has elapsed then the control routine continues to step 407. In step 407, the control routine turns the device off.

Figure 42:
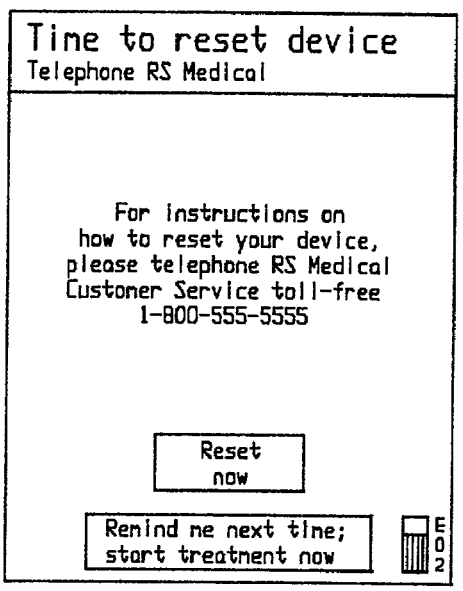

If, in step 390, the control routine determines that the battery power is sufficient to provide a full treatment, then the control routine continues to step 408. In step 408, the control routine determines whether a flag indicates that the device is being operated by a private owner. If, in step 408, the control routine determines that a private owner is not operating the device, then the control routine continues to step 410. In step 410, the control routine determines whether the device has expired. If, in step 410, the control routine determines that the device has expired, then the control routine continues to step 412. In step 412, the control routine displays a "reset" screen, an example of which is shown in FIG. 42, and continues to step 418. In step 418, the control routine determines whether the "reset now" button has been touched.

Figure 43:
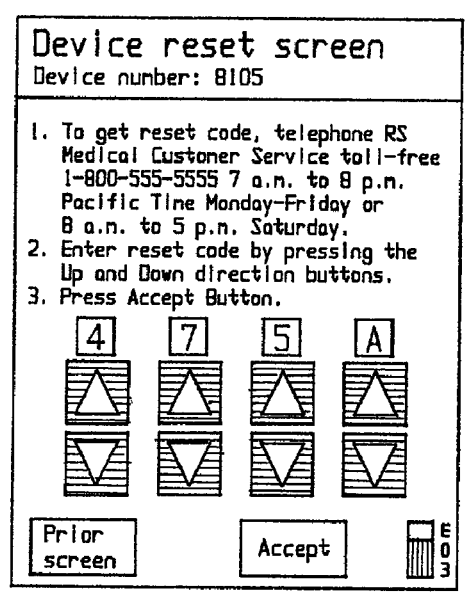

If, in step 418, the control routine determines that the "reset now" button has been touched, then the control routine continues to step 420. In step 420, the control routine displays a "device reset" screen, an example of which is shown in FIG. 43, and continues to step 422. In step 422, the control routine determines whether the "accept" button has been touched. If, in step 422, the control routine determines that the "accept" button has not been touched, then the control routine continues to step 424. In step 424, the control routine determines whether one minute has elapsed. If, in step 424, the control routine determines that one minute has not elapsed, then the control routine returns to step 422. If, however, in step 424, the control routine determines that one minute has elapsed, then the control routine continues to step 425. In step 425, the control routine turns the device off.

If, however, in step 422, the control routine determines that the "accept" button has been touched, then the control routine continues to step 426. In step 426, the control routine determines whether a valid number has been entered in the "device reset" screen. If, in step 426, the control routine determines that a valid number has been entered, then the control routine continues to step 428. In step 428, the control routine resets the device and continues to step 430. In step 430, the control routine starts the segment by executing the control routine outlined in FIG. 17.

Figure 44:
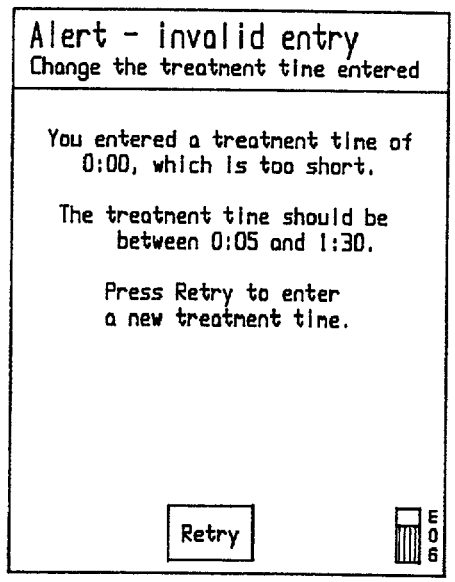
Figure 45:
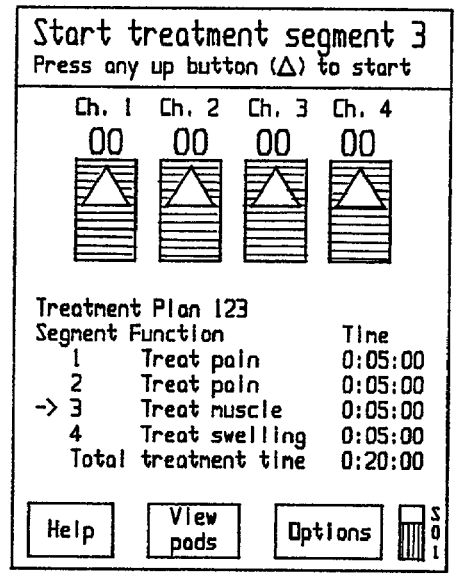
Figure 46:
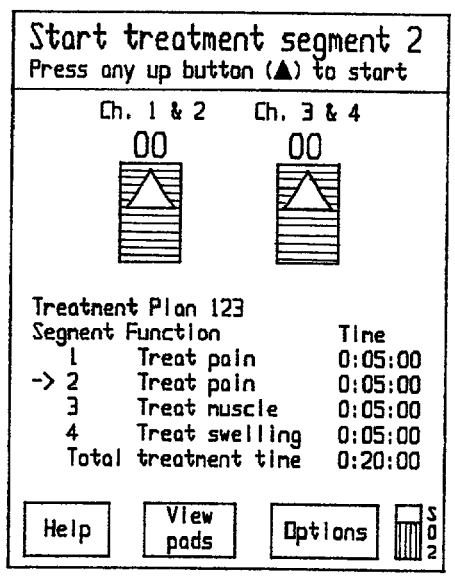
Figure 47:
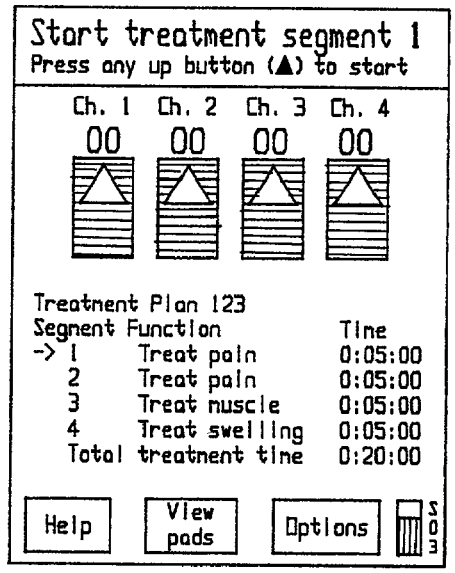
Figure 48:
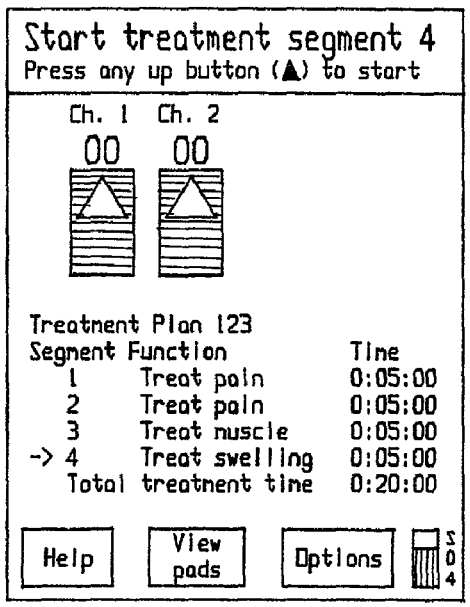
Figure 49:
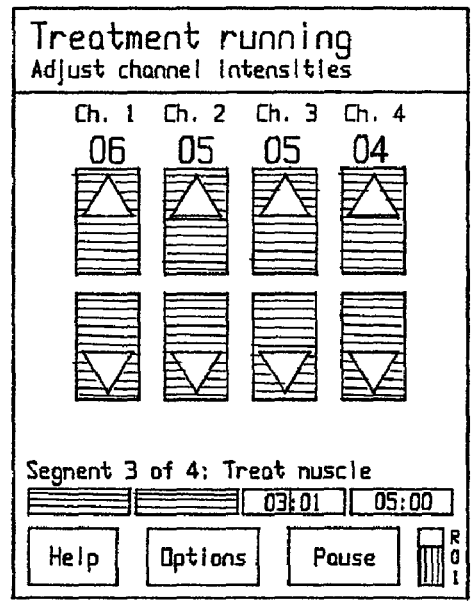
Figure 50:
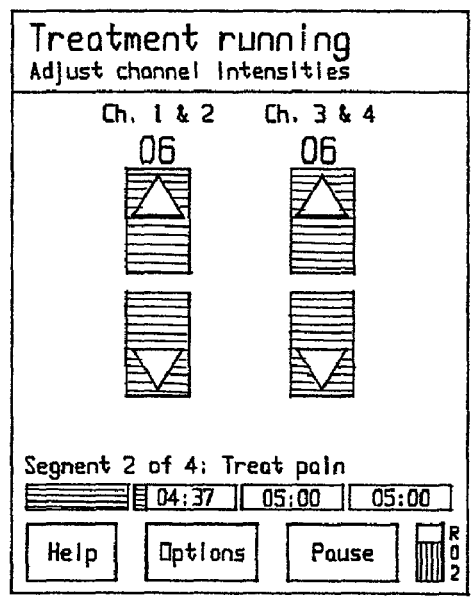
Figure 51:
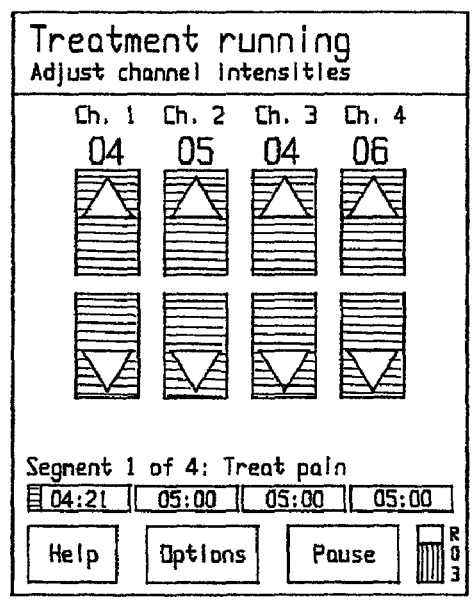
Figure 52:
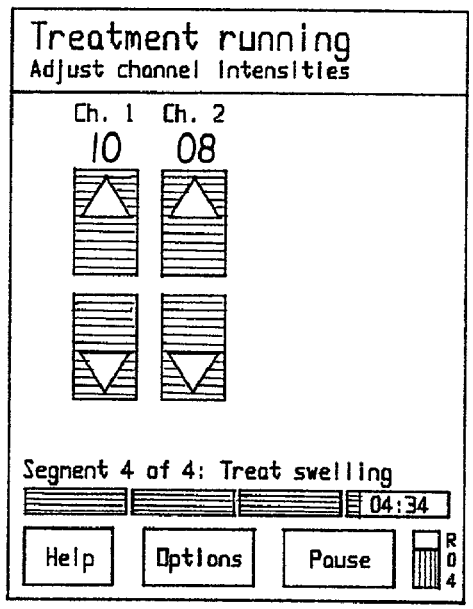

If, however, in step 426, the control routine determines that a valid number has not been entered, then the control routine continues to step 438. In step 438, the control routine displays an "invalid entry" screen, an example of which is shown in FIG. 44, and continues to step 440. In step 440, the control routine determines whether the "retry" button has been touched. If, in step 440, the control routine determines that the "retry" button has not been touched, then the control routine jumps to step 446. If, however, in step 440, the control routine determines that the "retry" button has been touched, then the control routine continues to step 442. In step 442, the control routine determines whether the device has been reset three times today. If, in step 442, the control routine determines the device has been reset three times today, then the control routine continues to step 446. In step 446, the control routine the control routine shuts down the device. If, however, in step 442, the control routine determines that the device has not been reset three times today, then the control routine returns to step 420.

If, however, in step 418, the control routine determines that the "reset now" button has not been touched, then the control routine continues to step 432. In step 432, the control routine determines whether the "remind me next time; start treatment now" button has been touched. If, in step 432, the control routine determines that the "remind me next time; start treatment now" button has been touched, then the control routine continues to step 434. In step 434, the control routine executes the control routine outlined in FIG. 21 and continues to step 435. In step 435, the control routine executes the control routine set forth in the flow chart of FIG. 17.

If, however, in step 432 the control routine determines that the "remind me next time; start treatment now" button has not been touched, then the control routine continues to step 436. In step 436, the control routine determines whether one minute has elapsed. If, in step 436, the control routine determines that one minute has not elapsed, then the control routine returns to step 418. If, however, in step 436, the control routine determines that one minute has elapsed, then the control routine continues to step 437. In step 437, the control routine shuts down the device.

If, however, in step 408, the control routine determines that the private owner is operating the device, then the control routine jumps to step 416. If, in step 414, the control routine determines that the device is not past the warning date, then the control routine continues to step 416. In step 416, the control routine executes the control routine outlined in the flow chart shown in FIG. 17.

Figure 17:
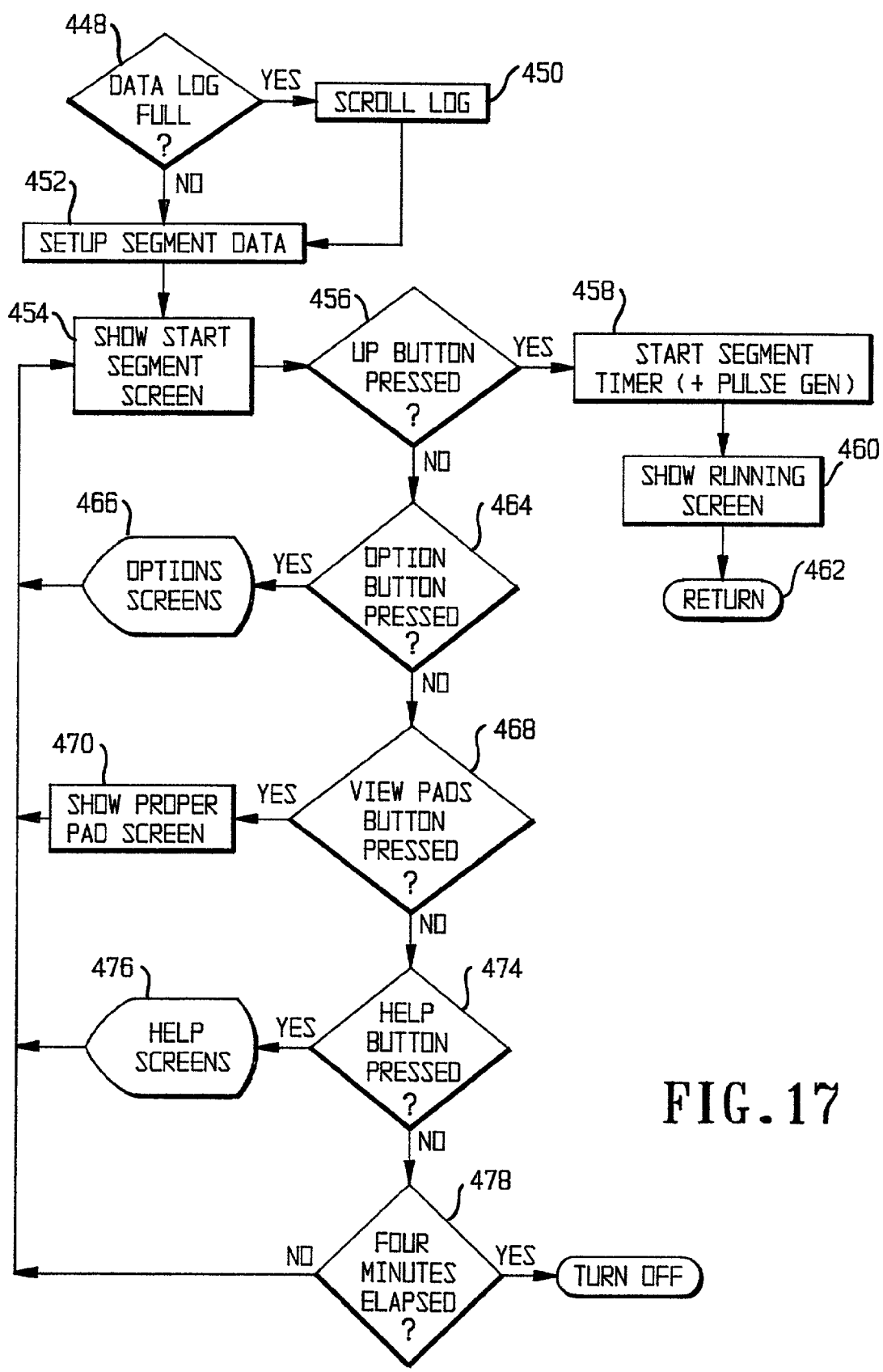

FIG. 17 is a flow chart that outlines the control routine for the start segment. The flow chart starts at step 448 where the control routine determines whether the data log is full. If, in step 448, the control routine determines that the data log is full, then the control routine continues to step 450. In step 450, the control routine displays an "internal update" screen, an example of which is shown in FIG. 15, scrolls the data log and continues to step 452. If, however, in step 448, the control routine determines that the data log is not full, then the control routine continues to step 452. In step 452, the control routine sets up the segment data that determines the device type and the operating parameters and continues to step 454. In step 454, the control routine shows one of the start segment screens, examples of which are shown in FIGS. 45–48, and continues to step 456. In step 456, the control routine determines whether one of the "up" buttons on the touch screen has been touched. If, in step 456, the control routine determines that one of the "up" buttons has been touched, then the control routine continues to step 458. In step 458, the control routine starts the segment timer and pulse generator and continues to step 460. The pulse generator is a background interrupt driven task that generates pulses for step 628 as explained below. In step 460, the control routine displays a "treatment running" screen, examples of which are shown in FIGS. 49–52, and continues to step 462. In step 462, the control routine sets the state of the device to "running" and continues to step 463. In step 463, the control routine returns control of the device to the control routine outlined in the flow chart of FIG. 12.

If, however, in step 456, the control routine determines that an "up" button has not been touched, then the control routine continues to step 464. In step 464, the control routine determines whether the "options" button has been touched on the touch screen. If, in step 464, the control routine determines that the "options" button has been touched, then the control routine continues to step 466. In step 466, the control routine executes the control routine outlined in the flow chart of FIG. 19 and returns to step 454. If, however, in step 464, the control routine determines that the "options" button has not been touched, then the control routine continues to step 468. In step 468, the control routine determines whether the "view pads" button has been touched. If, in step 468, the control routine determines that the "view pads" button has been touched, then the control routine continues to step 470.

In step 470, the control routine displays a "view pads" screen and returns to step 454. Exemplary "view pads" screens are shown in FIGS. 84–120. If, however, in step 468, the control routine determines that the "view pads" button has not been touched, then the control routine continues to step 474. In step 474, the control routine determines whether the "help" button has been touched on the touch screen. If, in step 474, the control routine determines that the "help" button has been touched on the touch screen, then the control routine continues to step 476. In step 476, the control routine executes the control routine that is outlined in the flow chart of FIG. 18 and returns to step 454. If, however, in step 474, the control routine determines that the "help" button has not been touched, then the control routine continues to step 478. In step 478, the control routine determines whether four minutes have elapsed. If, in step 478, the control routine determines that four minutes have not elapsed, then the control routine returns to step 454. If, however, in step 478, the control routine determines that four minutes have elapsed, then the control routine turns the device off.

Figure 18:
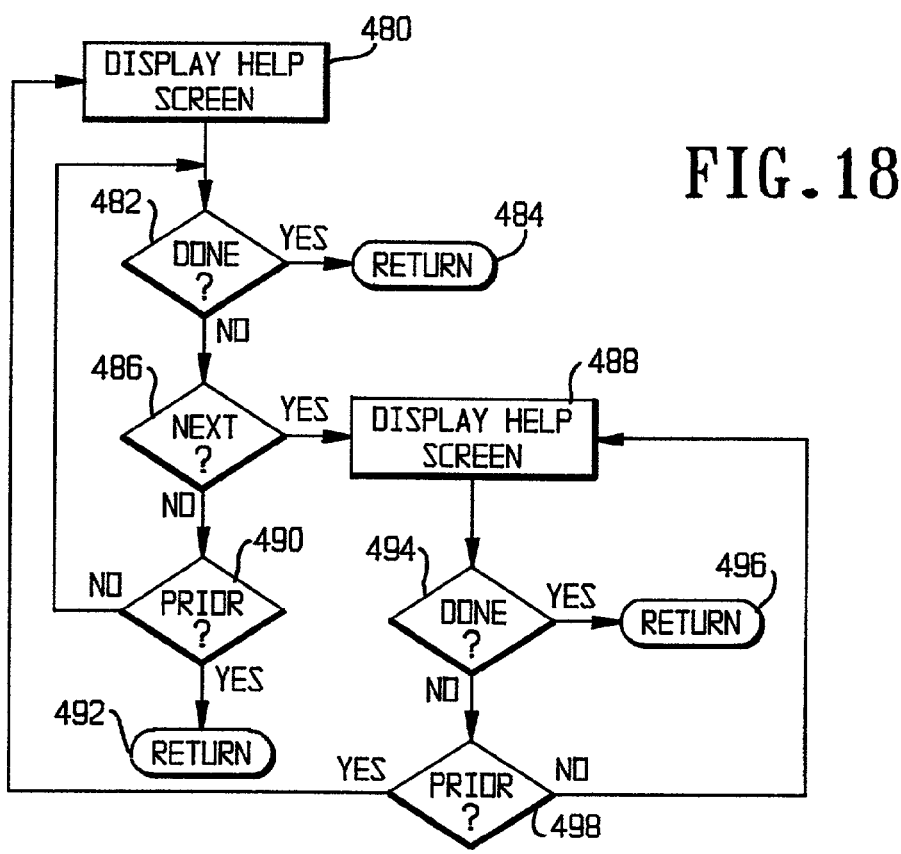
Figure 53:
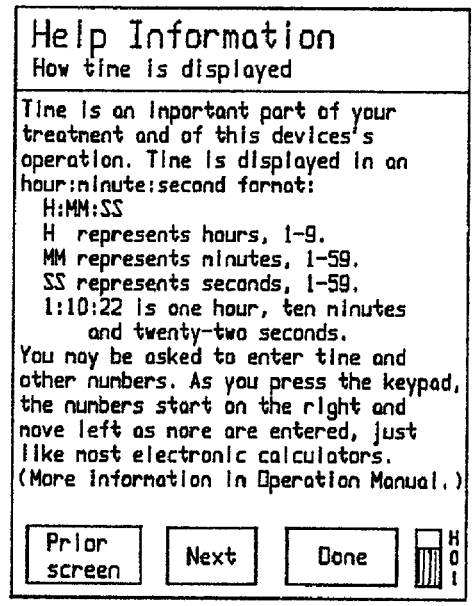

FIG. 18 is a flow chart that outlines the control routine for the "help" screens. The flow chart begins at step 480. In step 480, the control routine displays a "help" screen, an example of which is shown in FIG. 53, and continues to step 482. In step 482, the control routine determines whether the "done" button has been touched on the touch screen. If, in step 482, the control routine determines that the "done" button has been touched, then the control routine continues to step 484 where the control routine transfers control back to the control routine that called the help screens control routine of FIG. 18. If, however, in step 482, the control routine determines that the "done" button has not been touched, then the control routine continues to step 486.

Figure 54:
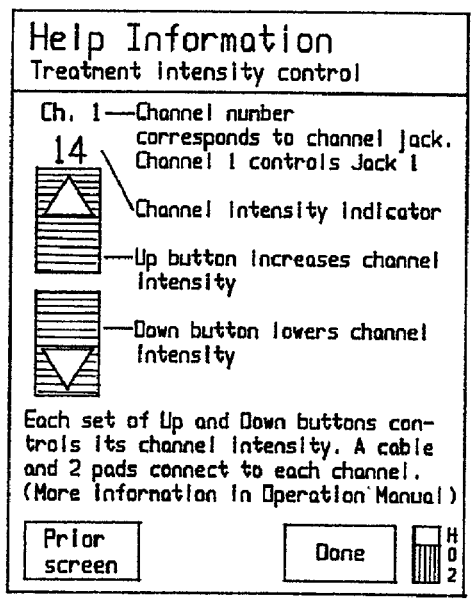

In step 486, the control routine determines whether the "next" button has been touched on the touch screen. If, in step 486, the control routine determines that the "next" button has been touched, then the control routine continues to step 488. In step 488, the control routine displays a "help" screen, an example of which is shown in FIG. 54, and continues to step 494. In step 494, the control routine determines whether the "done" button has been touched on the touch screen. If, in step 494, the control routine determines that the "done" button has been touched, then the control routine continues to step 496. In step 496, the control routine returns control to the control routine that called the help screens control routine in FIG. 18. If, however, in step 494, the control routine determines that the "done" button has not been touched, then the control routine continues to step 498. In step 498, the control routine determines whether the "prior screen" button has been touched on the touch screen. If, in step 498, the control routine determines that the "prior screen" button has been touched on the touch screen, then the control routine returns to step 480. If, however, in step 498, the control routine determines that the "prior" button has not been touched, then the control routine returns to step 488.

If, however, in step 486, the control routine determines that the "next" button has not been touched, then the control routine continues to step 490. In step 490, the control routine determines whether the "prior screen" button has been touched. If, in step 490, the control routine determines that the "prior screen" button has been touched, then the control routine continues to step 492. In step 492, the control routine transfers control to the control routine that called the help screens control routine in FIG. 18. If, however, in step 490, the control routine determines that the "prior screen" button has not been touched, then the control routine returns to step 482.

Figure 19:
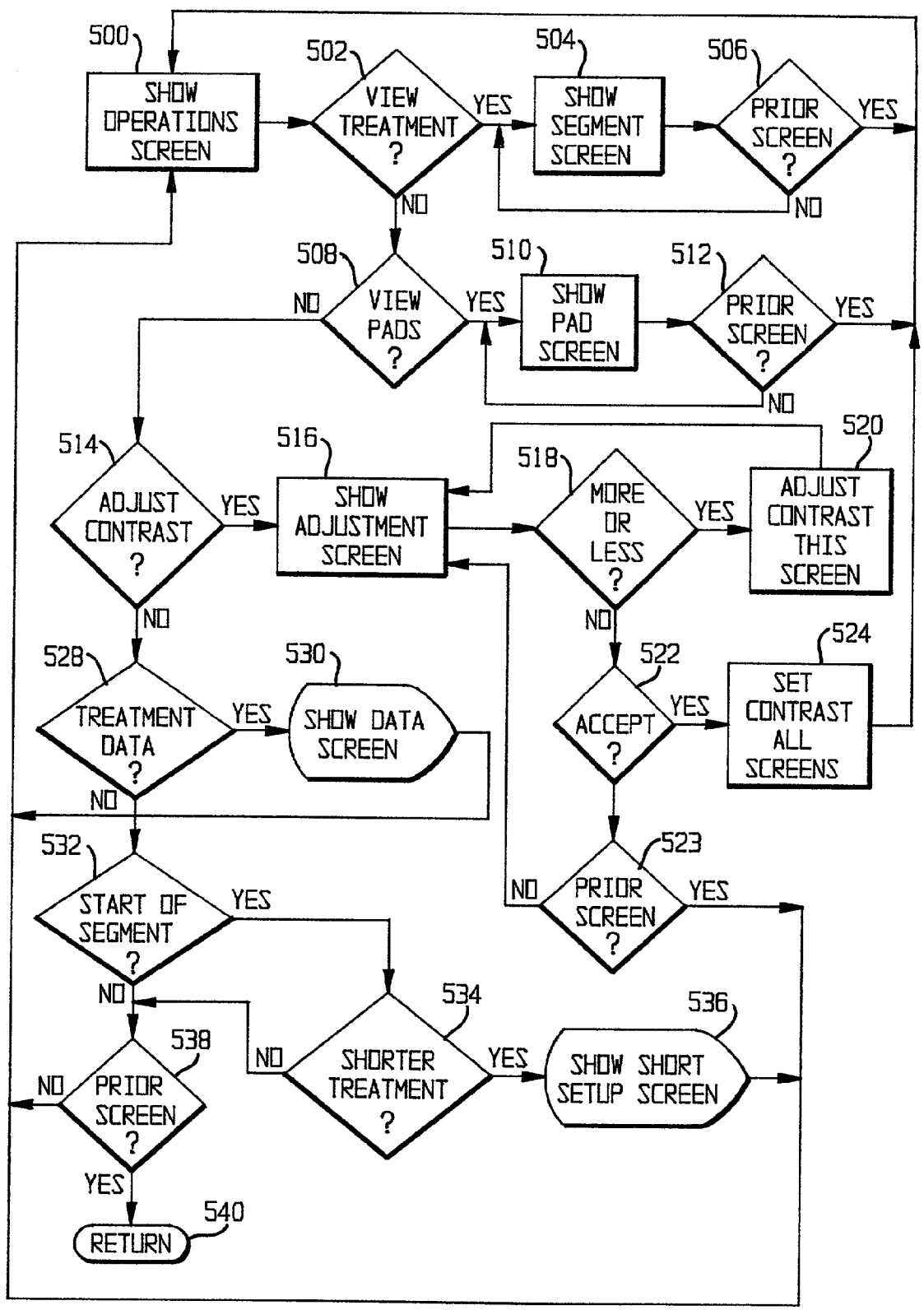
Figure 55:
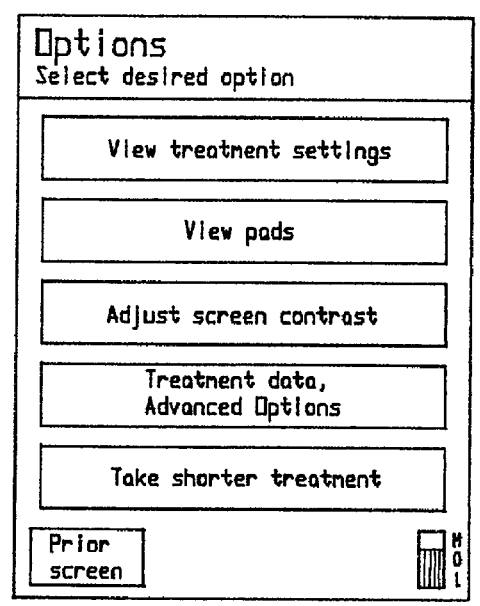
Figures 56, 57, 58, 59:
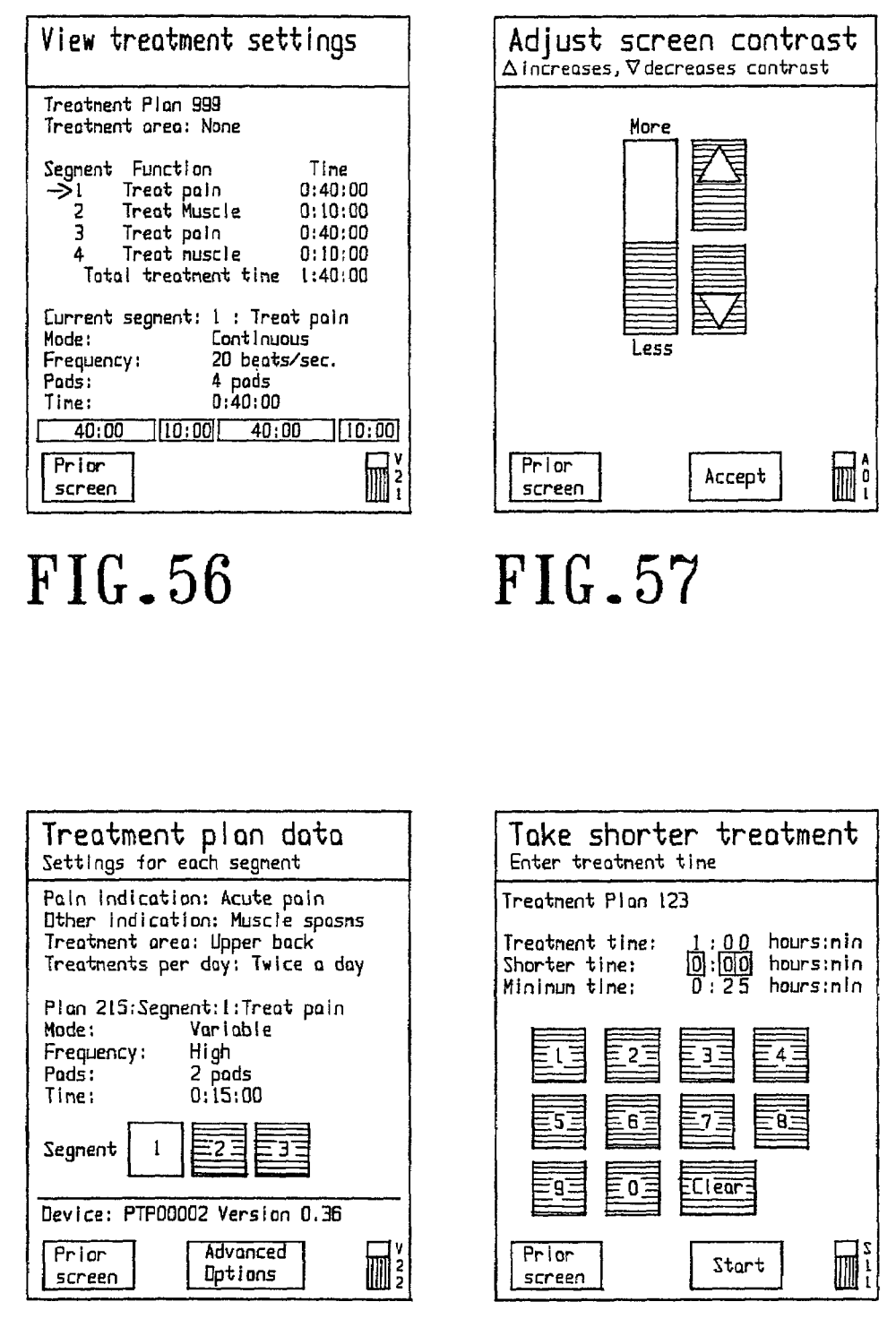
Figure 60:
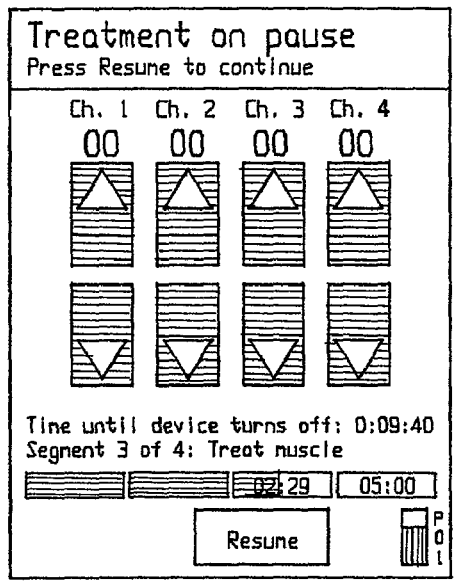
Figure 61:
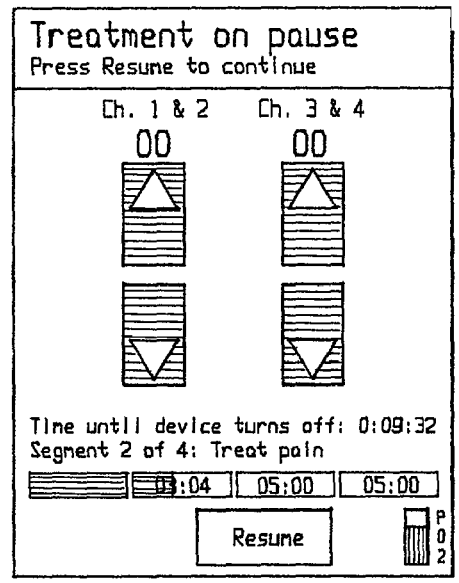
Figure 62:
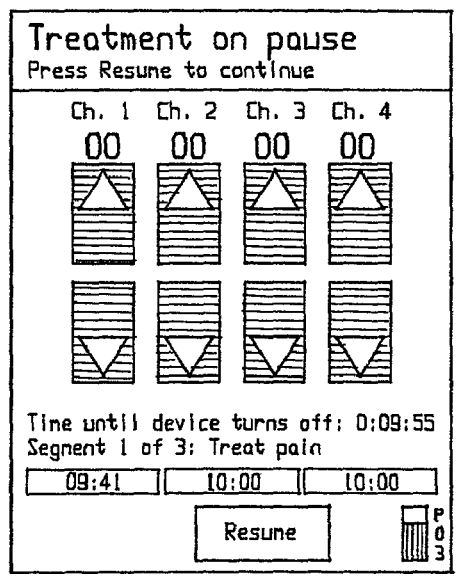
Figure 63:
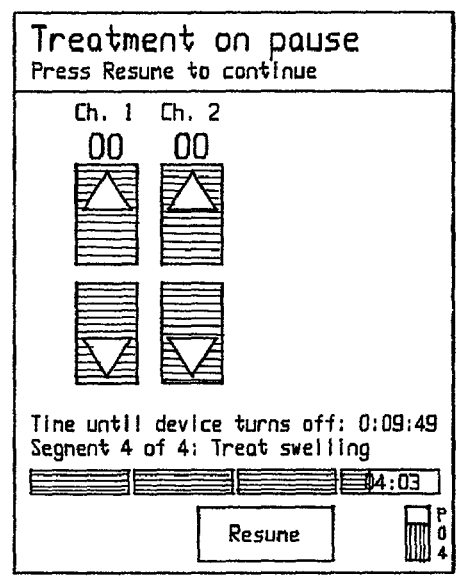
Figure 64:
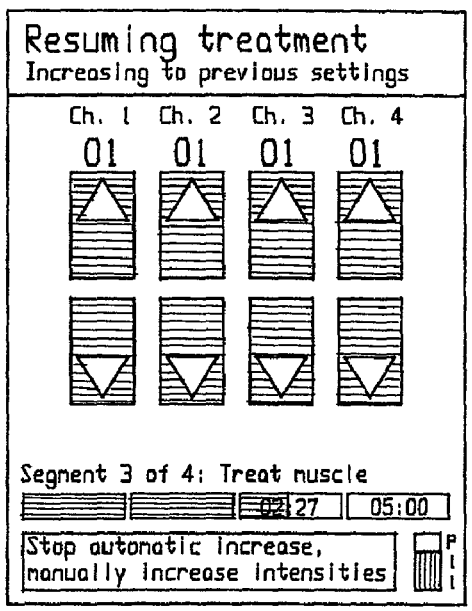
Figure 65:
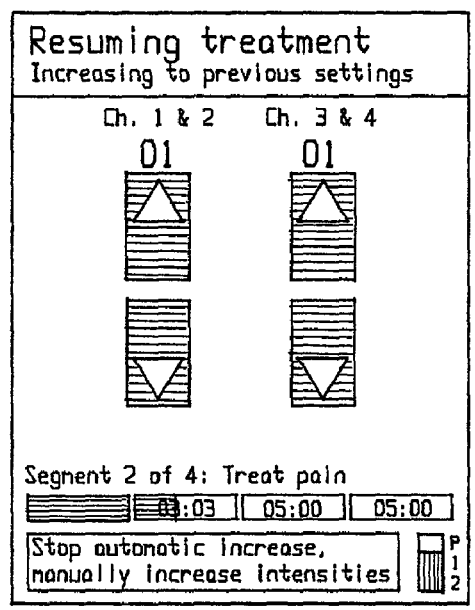
Figure 66:
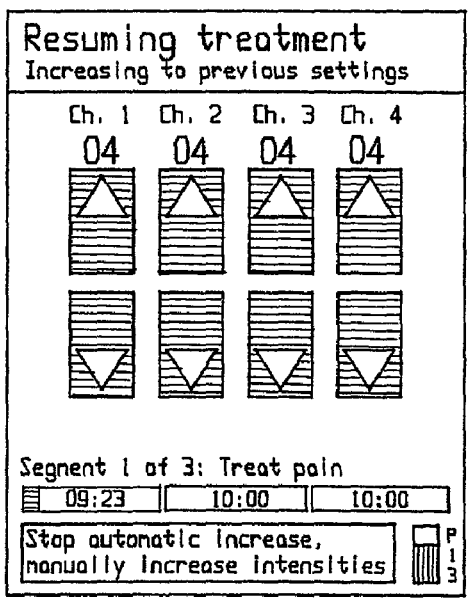
Figure 67:
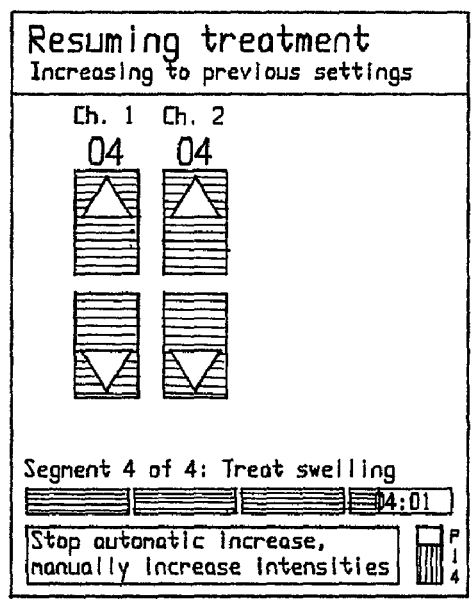

FIG. 19 outlines the control routine for modifying the options in accordance with the present invention. The flow chart starts at step 500 where the control routine displays an "options" screen, an example of which is shown in FIG. 55, and continues to step 502. In step 502, the control routine determines whether the "view treatments settings" button has been touched on the touch screen. If, in step 502, the control routine determines that the "view treatment settings" button has been touched, then the control routine continues to step 504. In step 504, the control routine displays the "view treatment settings" screen, an example of which is shown in FIG. 56, and continues to step 506. In step 506, the control routine determines whether the "prior screen" button has been touched. If the "prior screen" button has been touched, then the control routine returns to step 500. If, however, in step 506, the control routine determines that the "prior screen" button has not been touched, then the control routine returns to step 504.

If, however, in step 502, the control routine determines that the "view treatment settings" button has not been touched, then the control routine continues to step 508. In step 508, the control routine determines whether the "view pads" button has been touched on the touch screen. If, in step 508, the control routine determines that the "view pads" button has been touched, then the control routine continues to step 510. In step 510, the control routine displays a "view pads" screen, examples of which are shown in FIGS. 84–120, and continues to step 512. In step 512, the control routine determines whether the "prior screen" button has been touched. If, in step 512, the control routine determines that the "prior screen" button has been touched, then the control routine returns to step 500. If, however, in step 512, the control routine determines that the "prior screen" button has not been touched, then the control routine returns to step 510.

If, however, in step 508, the control routine determines that the "view pads" button has not been touched, then the control routine continues to step 514. In step 514, the control routine determines whether the "adjust screen contrast" button has been touched on the touch screen. If, in step 514, the control routine determines that the "adjust screen contrast" button has been touched, then the control routine continues to step 516. In step 516, the control routine displays an "adjust screen contrast" display, an example of which is shown in FIG. 57 and continues to step 518. In step 518, the control routine determines whether one of the "more" or "less" buttons have been touched on the touch screen. If one of the "more" or "less" buttons have been touched on the touch screen, then the control routine continues to step 520. In step 520, the control routine adjusts the screen contrast of the current display in accordance with the more or less request and returns to step 516. If, however, in step 518, the control routine determines that neither a "more" or "less" button has been touched, then the control routine continues to step 522. In step 522, the control routine determines whether the "accept" button has been touched.

If, in step 522, the control routine determines that the "accept" button has been touched, then the control routine continues to step 524. In step 524, the control routine sets the contrast on all screens and returns to step 500. If, however, in step 522, the control routine determines that the "accept" button has not been touched, then the control routine continues to step 523. In step 523, the control routine determines whether the "prior screen" button has been touched on the touch screen. If, in step 523, the control routine determines that the "prior screen" button has been touched, then the control routine returns to step 500. If, however, in step 523, the control routine determines that the "prior screen" button has not been touched, then the control routine returns to step 516.

If, in step 514, the control routine determines that the "adjust screen contrast" button has not been touched, then the control routine continues to step 528. In step 528, the control routine determines whether the "Treatment data, Advanced options" button has been touched. If, in step 528, the control routine determines that the "Treatment data, Advanced options" button has been touched, then the control routine continues to step 530. In step 530, the control routine executes the control routine outlined in the flow chart of FIG. 20, and returns to step 500.

If, however, in step 528, the control routine determines that the "Treatment data, Advanced options" button has not been touched, then the control routine continues to step 532. In step 532, the control routine determines whether the device is at the start of a treatment segment. If, in step 532, the control routine determines that the device is at the start of a segment, then the control routine continues to step 534. In step 534, the control routine determines whether the "take shorter treatment" button has been touched. If, in step 534, the control routine determines that the "take shorter treatment" button has been touched, then the control routine continues to step 536. In step 536, the control routine displays a take shorter treatment screen, an example of which is shown in FIG. 59, executes the control routine outlined in FIG. 21 and returns to step 500. If, however, in step 534, the control routine determines that the "take shorter treatment" button has not been touched, then the control routine continues to step 538.

If, in step 532, the control routine determines that the device is not at the start of a treatment segment, then the control routine continues to step 538. In step 538, the control routine determines whether the "prior screen" button has been touched. If, in step 538, the control routine determines that the "prior screen" button has been touched, then the control routine continues to step 540. In step 540, the control routine returns control of the device to the control routine that called the option screen control routine of FIG. 19. If, however, the control routine determines that the "prior screen" button has not been touched, then the control routine returns to step 500.

Figure 20:
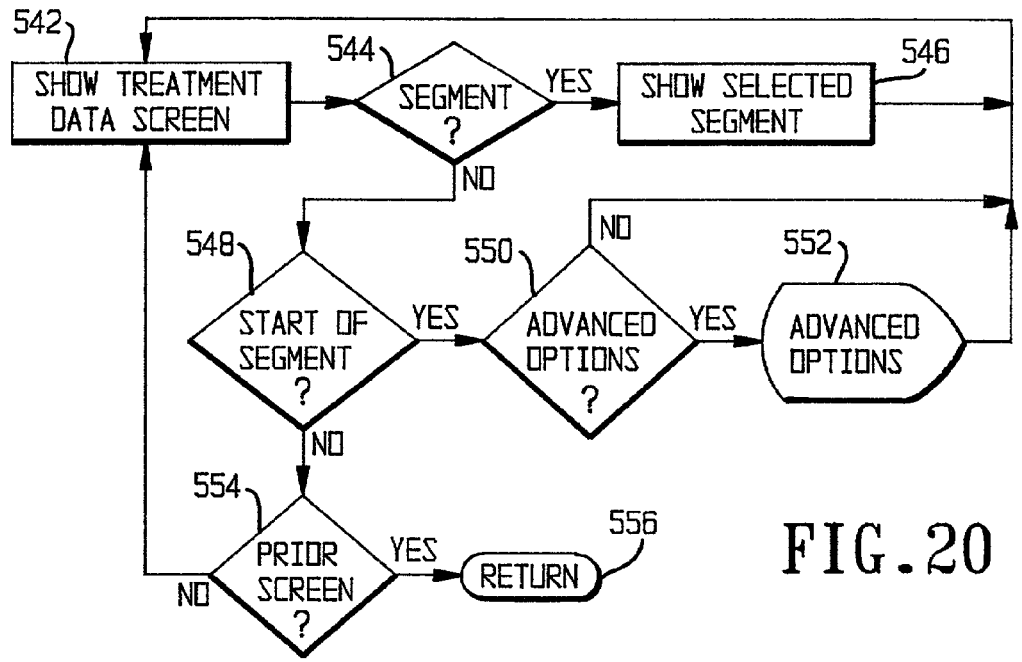

FIG. 20 outlines the control routine of the option sub screens of the exemplary device. The flow chart starts at step 542 where the control routine displays a "treatment plan data" screen, an example of which is shown in FIG. 58 and continues to step 544. In step 544, the control routine determines whether one of the "segment" buttons has been touched on the touch screen. If, in step 544, the control routine determines that one of the "segment" buttons have been touched, then the control routine continues to step 546. In step 546, the control routine updates the display to show the selected segment data and returns to step 542. If, however, in step 544, the control routine determines that none of the "segment" buttons have been touched, then the control routine continues to step 548. In step 548, the control routine determines whether the device is at the start of a segment. If, in step 548, the control routine determines that the device is at the start of a segment, then the control routine continues to step 550. In step 550, the control routine determines whether the "advanced options" button has been touched. If, in step 550, the control routine determines that the "advanced options" button has been touched, then the control routine continues to step 552. In step 552, the control routine executes the advanced options control routine detailed in the flow chart of FIG. 32 and returns to step 542. If, however, in step 550, the control routine determines that the "advanced options" button has not been touched, then the control routine returns to step 542.

If, in step 548, the control routine determines that the device is not at the start of a segment, then the control routine continues to step 554. In step 554, the control routine determines whether the "prior screen" button has been touched. If, in step 554, the control routine determines that the "prior screen" button has been touched, then the control routine continues to step 556. In step 556, the control routine returns control of the device back to the control routine that called the option sub screen control routine of FIG. 20. If, however, in step 554, the control routine determines that the "prior screen" button has not been touched, then the control routine returns to step 542.

Figure 21:
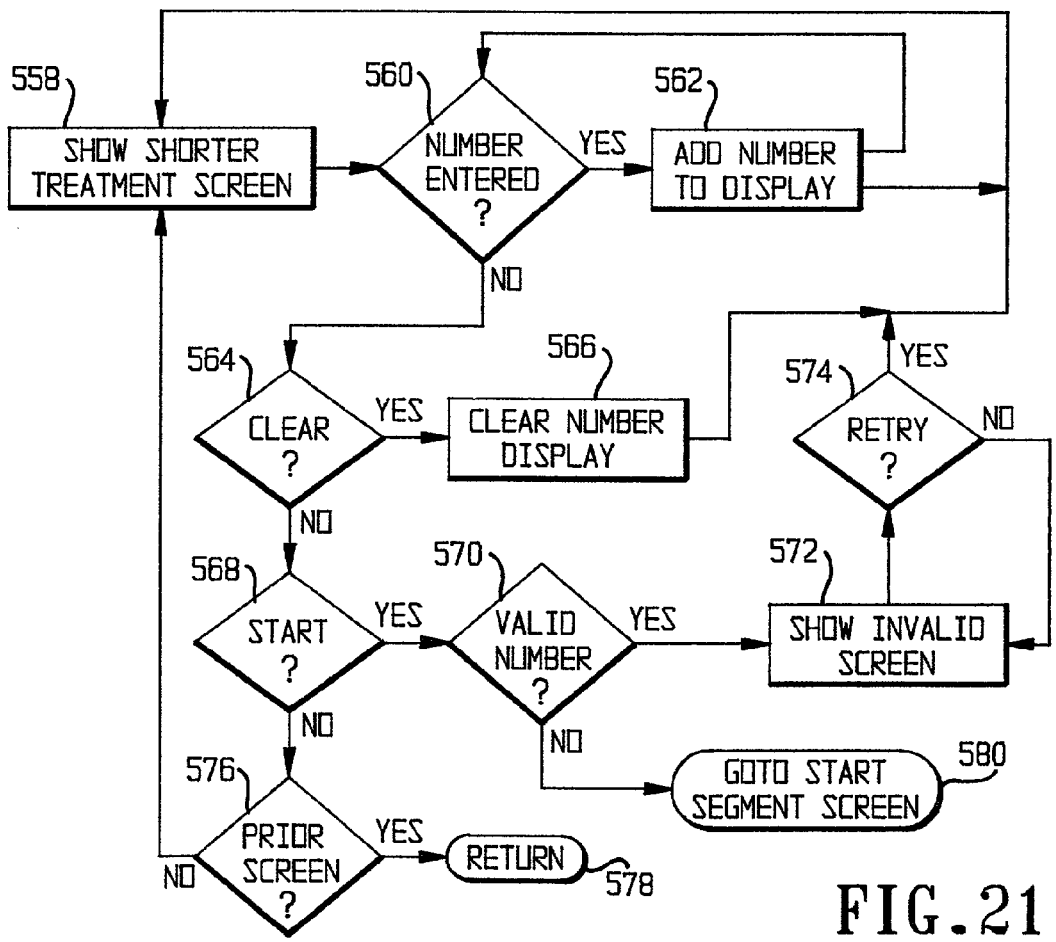

FIG. 21 shows a flow chart that outlines the control routine for administering a shorter treatment. The flow chart starts at step 558 where the control routine displays a "take shorter treatment" screen, an example of which is shown in FIG. 59, and continues to step 560. In step 560, the control routine determines whether a number has been entered. If, in step 560, the control routine determines that a number has been entered, the n the control routine continues to step 562. In step 562, the control routine adds the entered number to the display and returns to step 558. If, however, in step 560, the control routine determines that a number has not been entered, then the control routine continues to step 564. In step 564, the control routine determines whether the "clear" button has been touched on the touch screen. If, in step 564, the control routine determines that the "clear" button has been touched, then the control routine continues to step 566. In step 566, the control routine clears the display of numbers and returns to step 558. If, however, in step 564, the control routine determines that the "clear" button has not been touched, then the control routine continues to step 568.

In step 568, the control routine determines whether the "start" button has been touched. If, in step 568, the control routine determines that the "start" button has been touched, then the control routine continues to step 570. In step 570, the control routine determines whether a valid number has been entered. If, in step 570, the control routine determines that a valid number has been entered, then the control routine continues to step 580. In step 580, the control routine returns to step 454 of FIG. 17. If, however, in step 570, the control routine determines that a valid number has not been entered, then the control routine continues to step 572. In step 572, the control routine displays an "invalid entry" screen, an example of which is shown in FIG. 44, and continues to step 574. In step 574, the control routine determines whether the "retry" button has been touched on the touch screen. If, in step 554, the control routine determines that the "retry" button has been touched, then the control routine returns to step 558. If, however, in step 574, the control routine determines that the "retry" button has not been touched, then the control routine returns to step 572.

If, however, in step 568, the control routine determines that the "start" button has not been touched, then the control routine continues to step 576. In step 576, the control routine determines whether the "prior screen" button has been touched. If, in step 576, the control routine determines that the "prior screen" button has been touched, then the control routine continues to step 578. In step 578, the control routine returns control of the device back to the control routine that called the running state control routine shown in FIG. 21. If, however, in step 576, the control routine determines that the "prior screen" button has not been touched, then the control routine returns to step 558.

Figure 22:
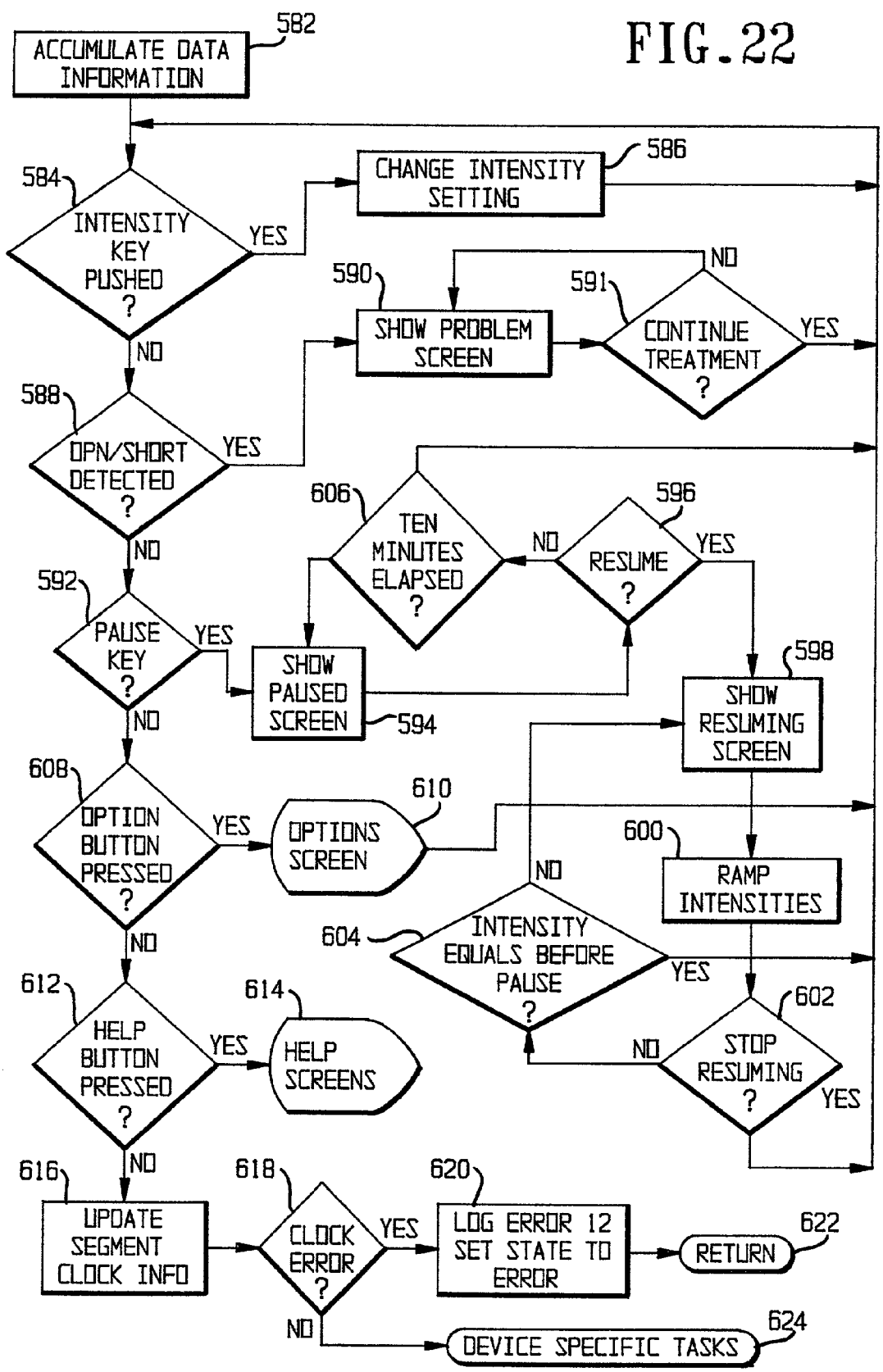
Figure 153:
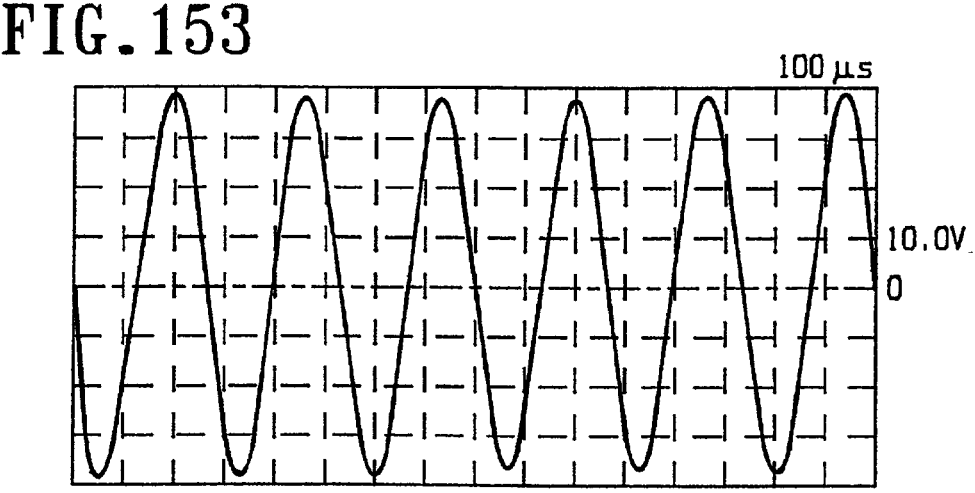

FIG. 22 is a flow chart that outlines the control routine for the running state of the device. The flow chart starts at step 582 where the control routine accumulates segment usage data, such as time used, maximum intensity, average intensity, and continues to step 584. In step 584, the control routine determines whether an intensity key (an up or down button) has been touched on the touch screen. If, in step 584, the control routine determines that an intensity key has been touched, then the control routine continues to step 586. In step 586, the control routine changes the intensity setting in accordance with the intensity key and returns to step 584. If, however, in step 584, the control routine determines that an intensity key has not been touched, then the control routine continues to step 588. In step 588, the control routine determines whether an open or a short is detected. If, in step 588, the control routine determines that an open or a short has been detected, then the control routine continues to step 590. In step 590, the control routine displays a "show problem screen," an example of which is shown in FIG. 153, and continues to step 591. In step 591, the control routine determines whether the "Continue treatment" button has been touched on the touch screen. If, in step 591, the control routine determines that the "Continue treatment" button has been touched on the touch screen, then the control routine returns to step 584. If, however, in step 591, the control routine determines that the "Continue treatment" button has not been touched on the touch screen, then the control routine returns to step 590.

If, however, in step 588, the control routine determines that an open or short has not been detected, then the control routine continues to step 592. In step 592, the control routine determines whether the "pause" button has been touched on the touch screen. If, in step 592, the control routine determines that the "pause" button has been touched, then the control routine continues to step 594. In step 594, the control routine displays a corresponding treatment on a "pause" display, examples of which are shown in FIGS. 60–63, and continues to step 596. In step 596, the control routine determines whether the "resume" button has been touched on the touch screen. If, in step 596, the control routine determines that the "resume" button has been touched, then the control routine continues to step 598.

In step 598, the control routine displays a "resuming treatment" screen, examples of which are shown in FIGS. 64–67, and continues to step 600. In step 600, the control routine ramps the intensities of the output on each of the channels back to the intensity prior to the pause and continues to step 602. In step 602, the control routine determines whether the "stop automatic increase, manually increase intensities" button has been touched. If, in step 602, the control routine determines that the "stop automatic increase, manual increase intensities" button has been touched, then the control routine sets the intensity at the current intensity and returns to step 584. If, however, in step 602, the control routine determines that the "stop automatic increase, manual increase intensities" button has not been touched, then the control routine continues to step 604. In step 604, the control routine determines whether the channel intensity equals the channel intensity prior to the pause. If, in step 604, the control routine determines that the channel intensity equals the channel intensity prior to the pause then the control routine returns to step 584. If, however, in step, S604, the control routine determines that the channel intensity does not equal the channel intensity before the pause, then the control routine returns to step 598.

If, however, in step 596, the control routine determines that the "resume" button has not been touched, then the control routine continues to step 606. In step 606, the control routine determines whether ten minutes have elapsed. If, in step 606, the control routine determines that ten minutes have not elapsed, then the control routine returns to step 594. If, however, the control routine determines that ten minutes have elapsed, then the control routine returns to step 584.

If, however, in step 592, the control routine determines that the "pause" key has not been touched, then the control routine continues to step 608. In step 608, the control routine determines whether the "Options" button has been touched. If, in step 608, the control routine determines that "Options" button has been touched, then the control routine continues to step 610. In step 610, the control routine executes the options screen control routine of FIG. 19 and returns to step 584.

If, however, in step 608, the control routine determines that the "Options" button has not been touched, then the control routine continues to step 612. In step 612, the control routine determines whether the "Help" button has been touched on the touch screen. If, in step 612, the control routine determines that the "Help" button has been touched, then the control routine continues to step 614. In step 614, the control routine executes the control routine detailed in the flow chart of FIG. 18 and returns to step 584.

If, however, in step 612, the control routine determines that the "Help" button has not been touched, then the control routine continues to step 616. In step 616, the control routine updates the segment clock information and continues to step 618. In step 618 the control routine determines whether a clock error exists. If, in step 618, the control routine determines that a clock error exists, then the control routine continues to step 620. In step 620, the control routine logs error 12, sets the state of the device to "error," executes the flow chart outlined in FIG. 28 and continues to step 622. In step 622, the control routine returns control of the device back to the control routine that called the running state control routine of the flow chart of FIG. 22. If, however, in step 618, the control routine determines that no clock error exists, then the control routine continues to step 624. In step 624, the control routine executes device specific tasks, examples of which are shown in FIGS. 23 and 24, as determined in step 452 of FIG. 17.

Figure 23:
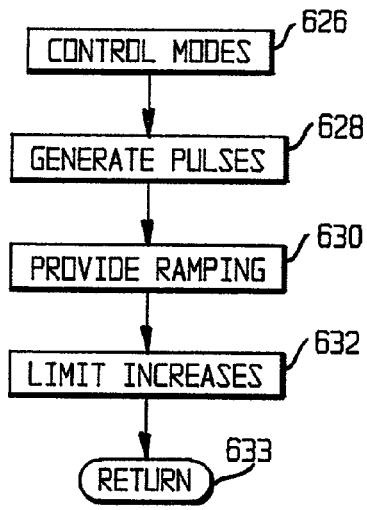

FIG. 23 outlines a control routine for an exemplary pulsed muscle stimulation task in accordance with this invention. The control routine starts at step 626 where the control routine sets the control modes to one of normal and alternate and continues to step 628. In step 628, the control routine generates pulses and continues to step 630. In step 630, the control routine provides ramping to the pulses and continues to step 632. In step 632, the control routine limits the increases in the intensity due to a user's touch on an increase key on the touch screen to prevent inadvertent inverses of the pulses and continues to step 633. In step 633, the control routine returns control of the device to the control routine that called the pulsed muscle stimulation treatment control routine of FIG. 23.

Figure 24:
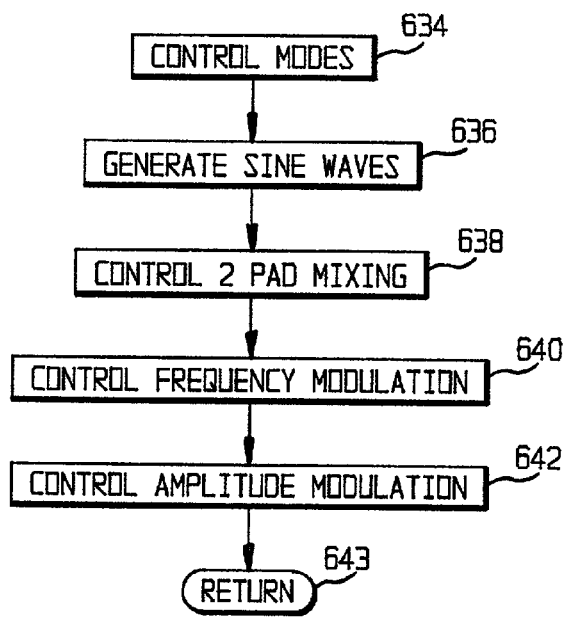

FIG. 24 shows a flow chart that outlines an exemplary control routine for an interferential device task in accordance with this invention. The control routine starts at step 634 where the control routine sets the control mode to one of a variable and continuous mode and continues to step 636. In step 636, the control routine generates sine waves and continues to step 638. In step 638, the control routine controls two pad mixing by premixing interferential signals and continues to step 640. In step 640 the control routine controls the frequency modulation and continues to step 642. In step 642, the control routine controls the amplitude modulation and continues to step 643 where the control routine returns to the control routine that called the interferential treatment control routine of FIG. 24.

Figure 25:
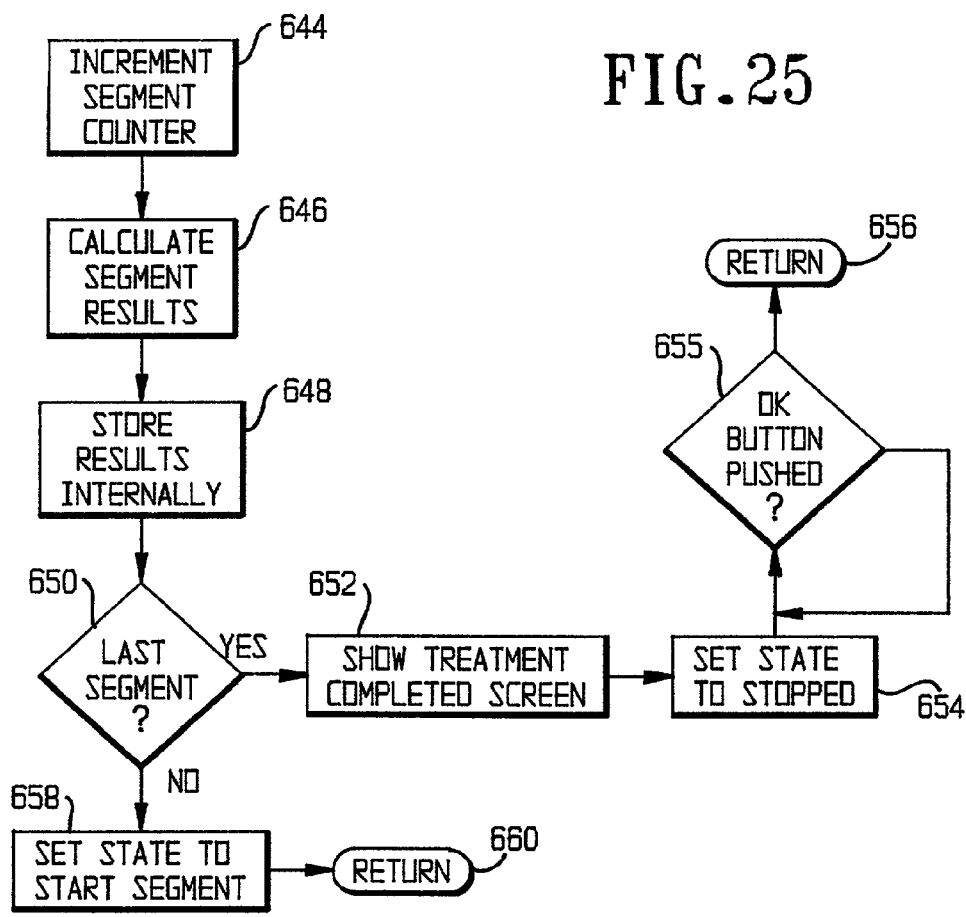

FIG. 25 shows a flow chart that outlines a control routine for a "segment end" state in accordance with the present invention. The control routine starts at step 644 where the control routine increments the segment counter and continues to step 646. In step 646, the control routine calculates the segment results and continues to step 648. In step 648, the control routine stores the results internally and continues to step 650. In step 650 the control routine determines whether this is the last segment. If, in step 650, the control routine determines that this is the last segment, then the control routine continues to step 652. In step 652, the control routine displays the "treatment completed" screen, an example of which is shown in FIG. 127, and continues to step 654. In step 654, the control routine sets the state of the device to "stopped" and continues to step 655. In step 655, the control routine determines whether the "OK" button has been touched on the touch screen. If, in step 655, the control routine determines that the "OK" button has been touched, then the control routine continues to step 656. In step 656, the control routine returns control of the device to the control routine that called the segment end state control routine of FIG. 25. If, however, in step 655, the control routine determines that the "OK" button has not been touched, then the control routine returns to step 655.

If, however, in step 650, the control routine determines that this is not the last segment, then the control routine continues to step 658. In step 658, the control routine sets the state of the device to "start segment," and continues to step 660. In step 660, the control routine returns control of the device to the control routine that called the segment end state control routine outlined in the flow chart of FIG. 25.

Figure 26:
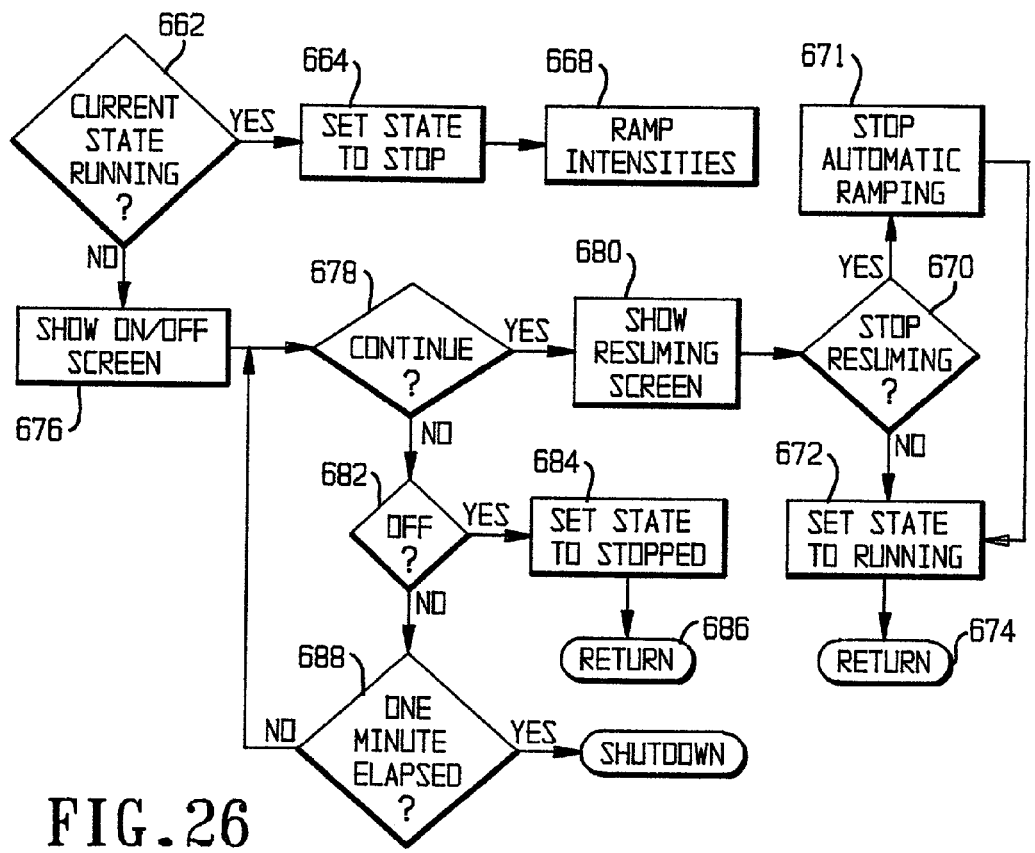

FIG. 26 shows a flow chart that outlines the control routine for an "off" state in accordance with an exemplary embodiment of the invention. The control routine starts at step 662 where the control routine determines whether the current state is "running". If, in step 662, the control routine determines that the current state is "running", then the control routine continues to step 664. In step 664, the control routine sets the state of the device to "stopped," and continues to step 668. In step 668, the control routine displays a "resuming treatment" display, an example of which is shown in FIGS. 64–67, ramps the intensities to the previously set intensities for the outputs and continues to step 670.

In step 670, the control routine determines whether the "stop automatic increase, manually increase intensities" button has been touched on the touch screen. If, in step 670, the control routine determines that the "stop automatic increase, manually increase intensities" button has been touched, then the control routine continues to step 671. In step 671, the control routine stops the automatic ramping of the output intensities and continues to step 672. If, however, in step 670 the control routine determines that the "stop automatic increase, manually increase intensities" button has not been touched, then the control routine continues to step 672. In step 672, the control routine sets the state of the device to "running," and continues to step 674. In step 674, the control routine returns control of the device to the control routine that called the off state control routine outlined in FIG. 26.

Figure 69:
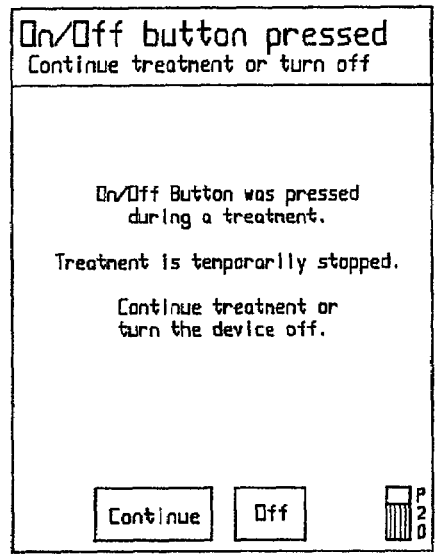

If, however, in step 662, the control routine determines that the current state is not "running," then the control routine continues to step 676. In step 676, the control routine displays an "on/off button pressed" display, an example of which is shown in FIG. 69, and continues to step 678. In step 678, the control routine determines whether the "continue" button has been touched on the touch screen. If, in step 678, the control routine determines that the "continue" button has been touched, then the control routine continues to step 680. In step 680, the control routine shows a "resuming treatment screen," examples of which are shown in FIGS. 63–67, and continues to step 668. If, however, in step 678, the control routine determines that the "continue" button has not been touched, then the control routine continues to step 682. In step 682, the control routine determines whether the "off" button has been touched on the touch screen. If, in step 682, the control routine determines that the "off" button has been touched, then the control routine continues to step 684. In step 684, the control routine sets the state of the device to "stopped," and continues to step 686. In step 686, the control routine returns control of the device to the control routine that called the off state control routine of FIG. 26.

If, however, in step 682, the control routine determines that the "off" button has not been touched, then the control routine continues to step 688. In step 688, the control routine determines whether one minute has elapsed. If, in step 688 the control routine determines that one minute has not elapsed, then the control routine returns to step 678. However, if, in step 688, the control routine determines that one minute has elapsed then the control routine shuts down the device.

Figure 27:
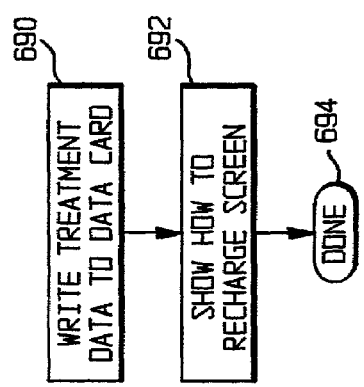

FIG. 27 outlines a "stopped" state control routine in accordance with an exemplary embodiment of the present invention. The control routine starts at step 690 where the control routine writes the treatment data to the data card 30 and continues to step 692. In step 692, the control routine displays a "how to recharge battery" screen, an example of which is shown in FIG. 41, and continues to step 694. In step 694, the control routine returns control of the device to the control routine that called the stopped state control routine of FIG. 27.

Figure 28:
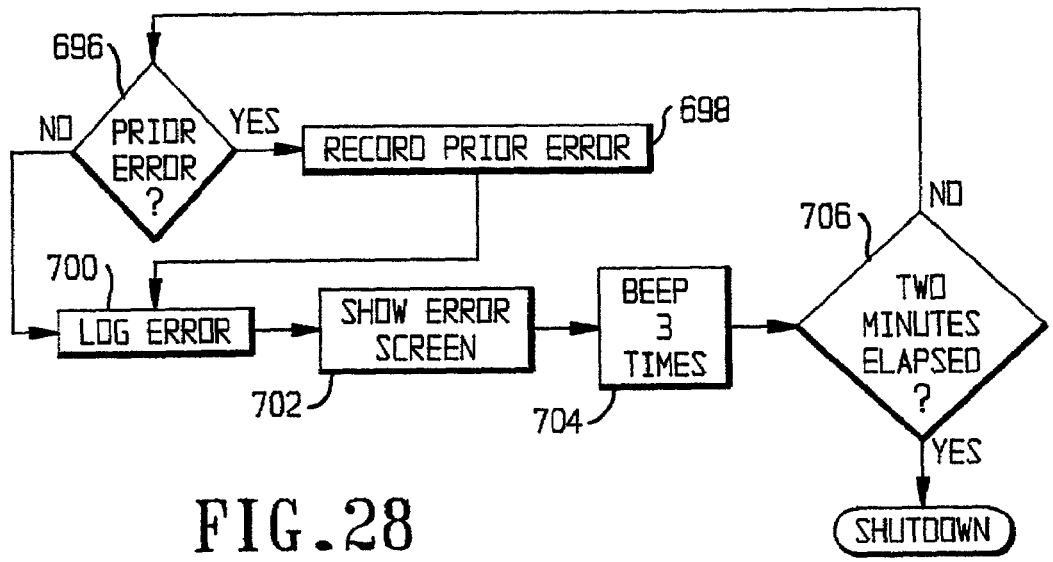
Figure 148:

FIG. 28, outlines an "error" state control routine. The control routine starts at step 696 where the control routine determines whether a prior error exists. If, in step 696, the control routine determines that a prior error exists, then the control routine continues to step 698. In step 698, the control routine records the prior error and continues to step 700. In step 700, the control routine logs the error and continues to step 702. In step 702, the control routine displays a "problem detected" screen, an example of which is shown in FIG. 148, and continues to step 704. In step 704, the control routine beeps three times and continues to step 706.

At step 706, the control routine determines whether two minutes have elapsed. If, in step 706 the control routine determines that two minutes have elapsed, then the control routine shuts down the device. The system restarts and if the control routine encounters the same error three consecutive times, then the device is shut down and cannot be restarted. If, however, in step 706, the control routine determines that two minutes have not elapsed, then the control routine returns to step 696. If, however, in step 696, the control routine determines that no prior error has been recorded, then the control routine continues to step 700.

Figure 29:
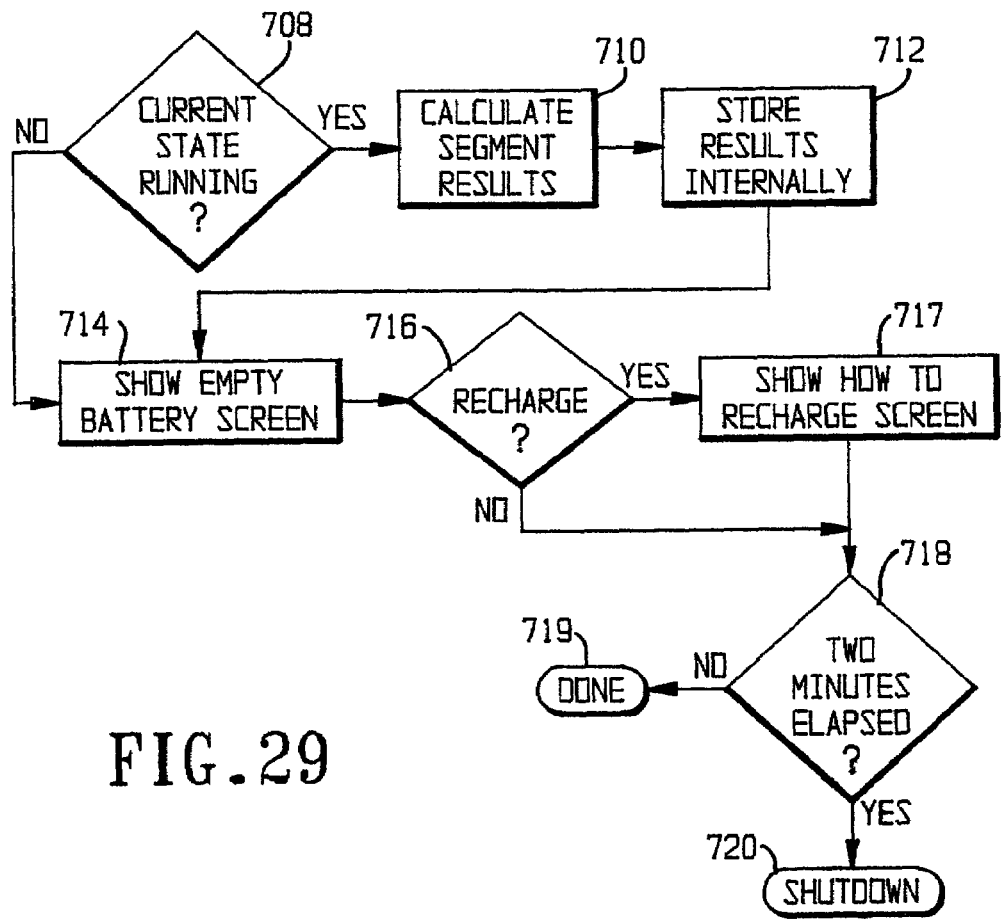
Figure 70:
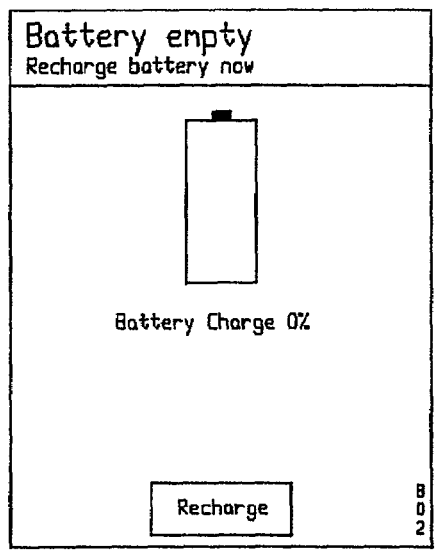

FIG. 29 outlines a "low battery" state control routine of an exemplary embodiment in accordance with the present invention. The control routine starts at step 708, where the control routine determines whether the current state is "running." If, in step 708, the control routine determines that the current state is "running," then the control routine continues to step 710. In step 710, the control routine calculates the segment results and continues to step 712. In step 712, the control routine stores the results and continues to step 714. If, however, in step 708, the control routine determines that the current state is not "running," then the control routine continues to step 714. In step 714, the control routine displays a "battery empty" screen, an example of which is shown in FIG. 70, and continues to step 716.

In step 716, the control routine determines whether the "recharge" button has been touched on the touch screen. If, in step 716, the control routine determines that the "recharge" button has been touched, then the control routine continues to step 717. In step 717, the control routine displays a "how to recharge battery" screen, an example of which is shown in FIG. 41, and continues to step 718. If, however, in step 716, the control routine determines that the "recharge" button has not been touched, then the control routine continues to step 718. In step 718, the control routine determines whether two minutes have elapsed. If, in step 718, the control routine determines that two minutes have not elapsed, then the control routine continues to step 719. In step 719, the control routine returns to the control routine that calls the control routine of FIG. 29. If, however, in step 718, the control routine determines that two minutes have elapsed, then the control routine continues to step 720. In step 720, the control routine shuts down the device.

Figure 30:
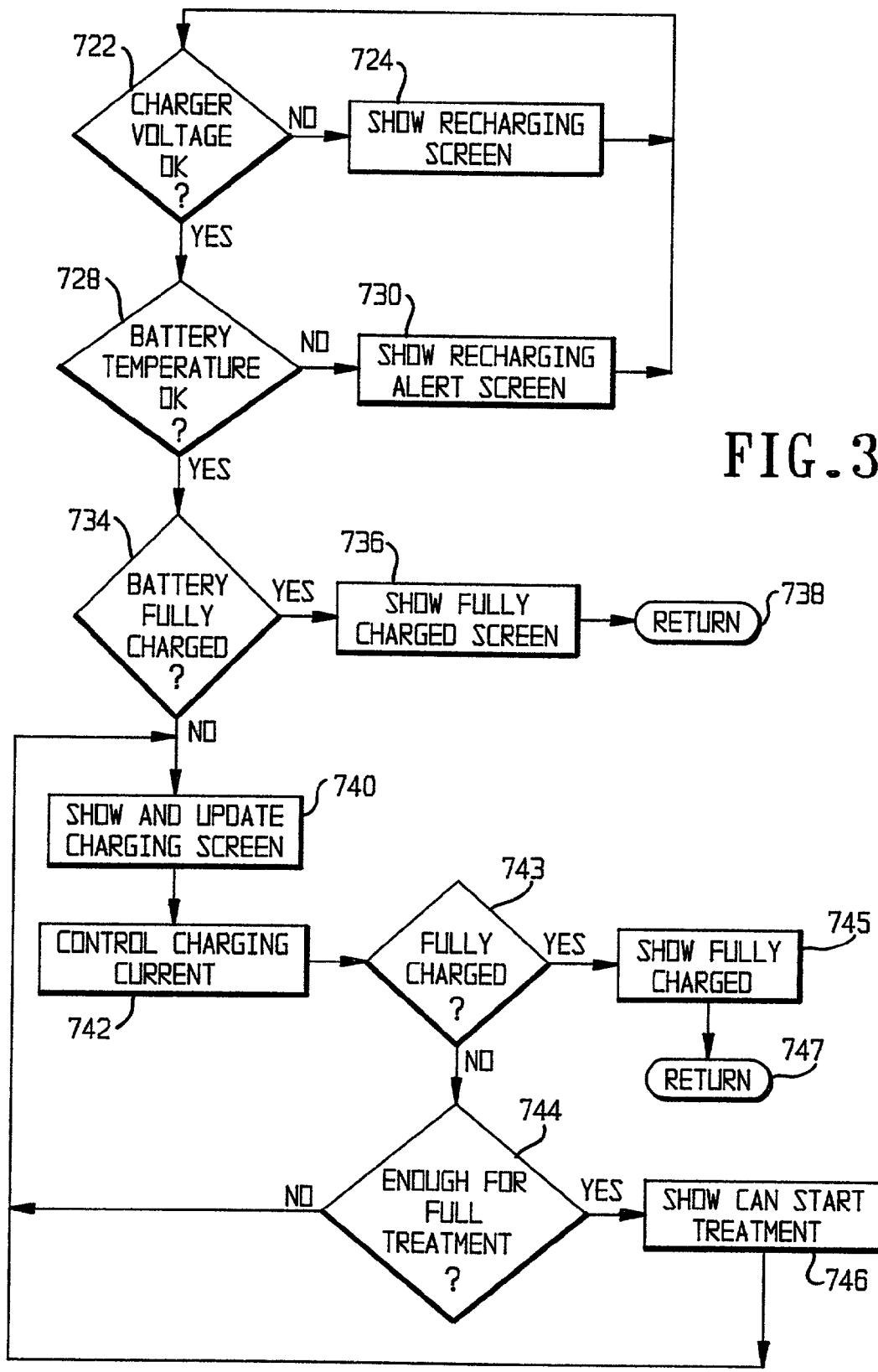
Figure 71:
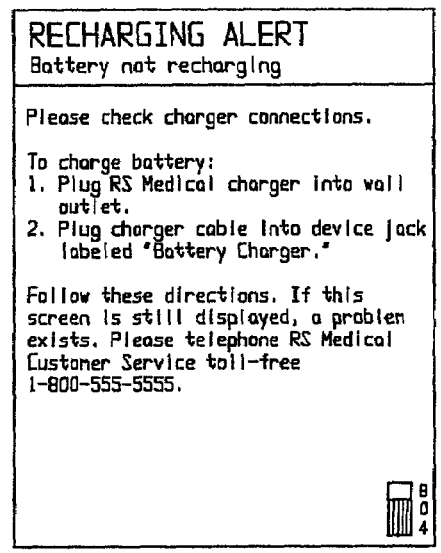

FIG. 30 outlines the "charging" state control routine of an exemplary embodiment in accordance with the present invention. The control routine starts at step 722 where the control routine determines whether the charger voltage is acceptable. If, in step 722, the control routine determines that the charger voltage is not acceptable, then the control routine continues to step 724. In step 724, the control routine displays a "recharging alert" display, an example of which is shown in FIG. 71, and returns to step 722. If, however, in step 722, the control routine determines that the charger voltage is acceptable, then the control routine continues to step 728.

Figure 72:
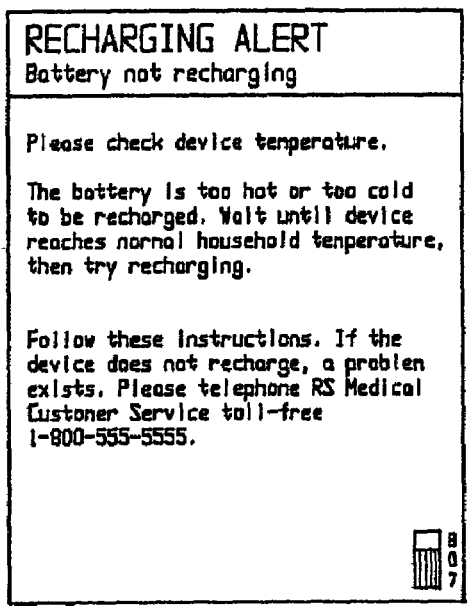
Figure 73:
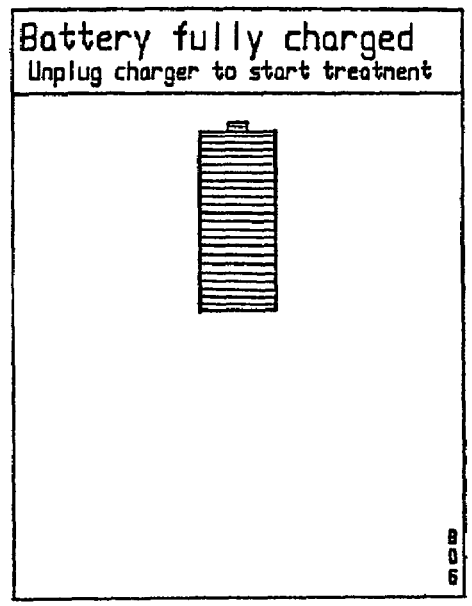

In step 728, the control routine determines whether the battery temperature is acceptable. If, in step 728, the control routine determines that the battery temperature is not acceptable, then the control routine continues to step 730. In step 730, the control routine displays a "recharging alert" display, an example of which is shown in FIG. 72 and returns to step 722. If, however, in step 728, the control routine determines that the battery temperature is acceptable, then the control routine continues to step 734. In step 734, the control routine determines whether the battery is fully charged. If, in step 734, the control routine determines that the battery is fully charged, then the control routine continues to step 736. In step 736, the control routine displays a "battery fully charged" screen, an example of which is shown in FIG. 73, and continues to step 738. In step 738, the control routine returns control to the control routine that called the charging state control routine outlined in the flow chart of FIG. 30. If, however, in step 734, the control routine determines that the battery is not fully charged, then the control routine continues to S740.

Figure 74:
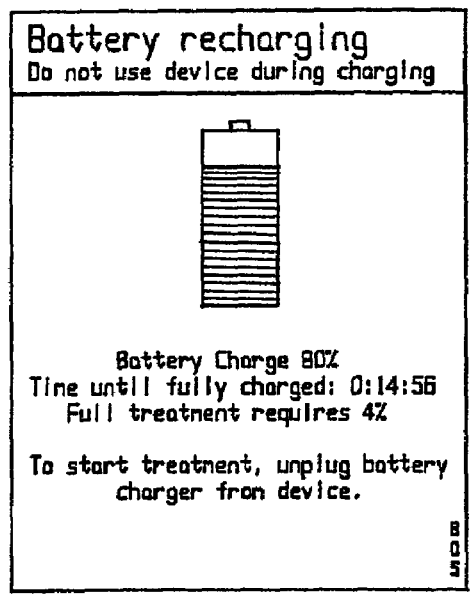

In step 740, the control routine shows a "battery recharging" screen, an example of which is shown in FIG. 74, and continues to step 742. In step 742, the control routine controls the charging current being supplied to the battery and continues to step 743. In step 743, the control routine determines whether the battery is fully charged. If, in step 743, the control routine determines that the battery is fully charged then the control routine continues to step 745. In step 745, the control routine displays a "Battery fully charged" screen, an example of which is shown in FIG. 73, and continues to step 747. In step 747, the control routine returns control of the device to the control routine that called the charging state control routine of FIG. 30.

If, however, in step 743, the control routine determines that the battery is not fully charged then the control routine continues to step 744. In step 744, the control routine determines whether the battery charge is enough for a full treatment. If, in step 744, the control routine determines that the battery has enough charge for a full treatment, then the control routine continues to step 746. In step 746, the control routine displays a message on the display that the treatment may be started and returns to step 740. If, however, in step 744, the control routine determines that the battery is not charged enough for a full treatment, then the control routine returns to step 740.

Figure 31:
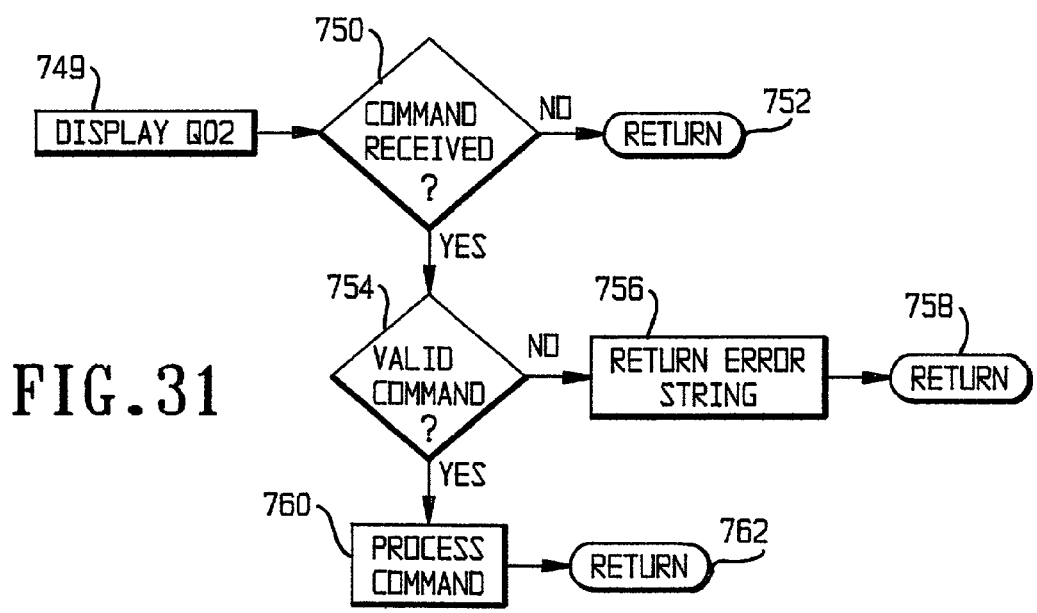

FIG. 31 outlines the "maintenance" state control routine of an exemplary embodiment of the present invention. The control routine starts at step 749 where the control routine displays a maintenance mode display, an example of which is shown in FIG. 154 and continues to step 750. In step 750, the control routine determines whether a command has been received. If, in step 750, the control routine determines that a command has not been received, then the control routine continues to step 752. In step 752, the control routine returns control to the control routine that called the maintenance state control routine outlined in FIG. 31. If, however, in step 750, the control routine determines that a command has been received, then the control routine continues to step 754.

In step 754, the control routine determines whether a valid command has been entered. If, in step 754, the control routine determines that a valid command has not been entered, then the control routine continues to step 756. In step 756, the control routine returns an error string and continues to step 758. In S758, control of the device returns to the control routine that called the maintenance state control routine of FIG. 31. If, however, in step 754, the control routine determines that a valid command has been received, then the control routine continues to step 760. In step 760, the control routine processes the command and continues to step 762. In step 762, the control routine returns control of the device to the control routine that called the maintenance state control routine outlined in FIG. 31.

Figure 32:
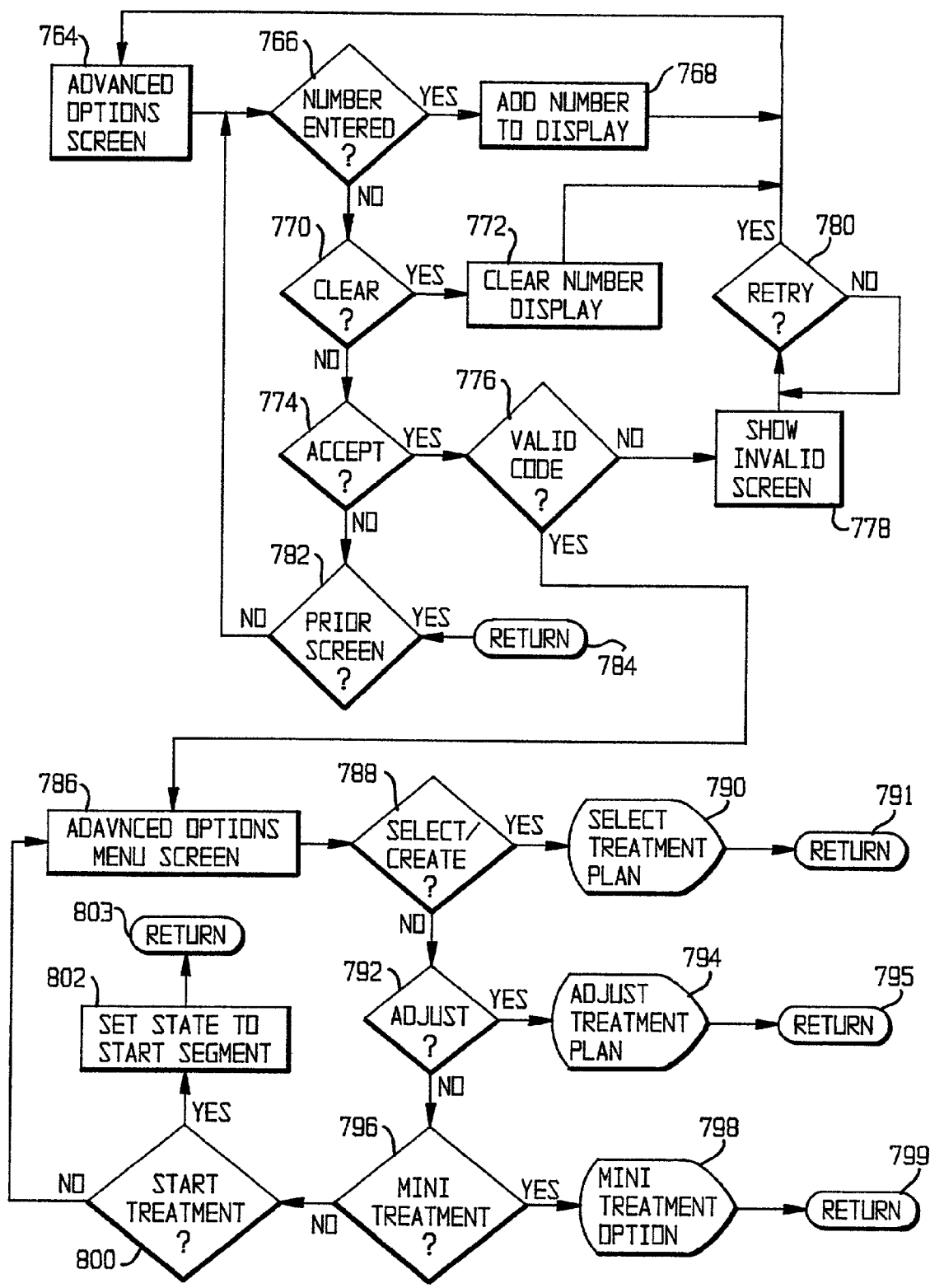
Figure 149:

FIG. 32 shows a flow chart that outlines an advanced options control routine of an exemplary embodiment in accordance with the present invention. The control routine starts at step 764 where the control routine displays an "advanced options" display, an example of which is shown in FIG. 149, and continues to S766. In step 766, the control routine determines whether a number has been entered. If, in step 766, the control routine determines that a number has been entered, then the control routine continues to step 768. In step 768, the control routine adds the entered number to the display and returns to step 764. If, however, in step 766, the control routine determines that a number has not been entered, then it continues to step 770.

In step 770, the control routine determines whether a "clear" button has been touched. If, in step 770, the control routine determines that a "clear" button has been touched, then the control routine continues to step 772. In step 772, the control routine clears the number display and returns to step 764. If, however, in step 770 the control routine determines that a "clear" button has not been touched on the touch screen, then the control routine continues to step 774. In step 774, the control routine determines whether an "accept" button has been touched on the touch screen. If, in step 774, the control routine determines that the "accept" button has not been touched, then the control routine continues to step 782.

In step 782, the control routine determines whether a "prior screen" button has been touched on the touch screen. If, in step 782, the control routine determines that the "prior screen" button has been touched, then the control routine continues to step 784. In step 784, the control routine returns to the control routine that called the advanced options control routine of the flow chart of FIG. 32.

If, however, in step 774, the control routine determines that an "accept" button has been touched, then the control routine continues to step 776. In step 776, the control routine determines whether a valid code has been entered. If, in step 776, the control routine determines that a valid code has not been entered, then the control routine continues to step 778. In step 778, the control routine displays an "alert-invalid entry" screen, an example of which is shown in FIG. 44, and continues to step 780. In step 780, the control routine determines whether the "retry" button has been touched on the touch screen. If, in step 780, the control routine determines that the "retry" button has been touched, then the control routine returns to step 764. If, however, in S780, the control routine determines that the "retry" button has not been touched, then the control routine returns to step 780.

Figure 75:
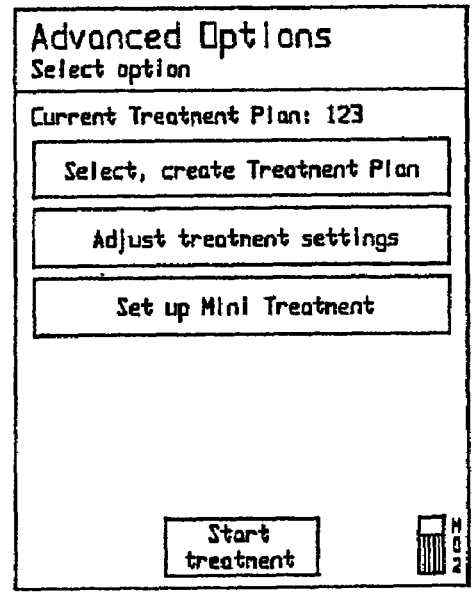

If, however, in step 776 the control routine determines that a valid code has been entered, then the control routine continues to step 786. In step 786, the control routine displays an "advanced options" screen, an example of which is shown in FIG. 75, and continues to step 788. In step 788, the control routine determines whether the "select, create treatment plan" button on the touch screen has been touched. If, in step 788, the control routine determines that the "select, create treatment plan" button has been touched, then the control routine continues to step 790. In step 790, the control routine transfers control to the control routine outlined in the flow chart of FIG. 33 and continues to step 791. In step 791, the control routine returns control of the device to the control routine that called the advanced options control routine of FIG. 32. If, however, in step 788, the control routine determines that the "select, create treatment plan" button has not been touched, then the control routine continues to step 792. In step 792, the control routine determines whether the "adjust treatment settings" button has been touched on the touch screen. If, in step 792, the control routine determines that the "adjust treatment settings" button has been touched, then the control routine continues to step 794. In step 794, the control routine transfers control to the control routine outlined in the flow chart of FIG. 35 and continues to step 795. In step 795, the control routine returns control of the device to the control routine that called the advanced options control routine of FIG. 32. If, however, in step 792, the control routine determines that the "adjust treatment settings" button has not been touched, then the control routine continues to step 796.

In step 796, the control routine determines whether the "setup mini treatment" button has been touched on the touch screen. If, in step 796, the control routine determines that the "setup mini treatment" button has been touched, then the control routine continues to step 798.

Figure 39:
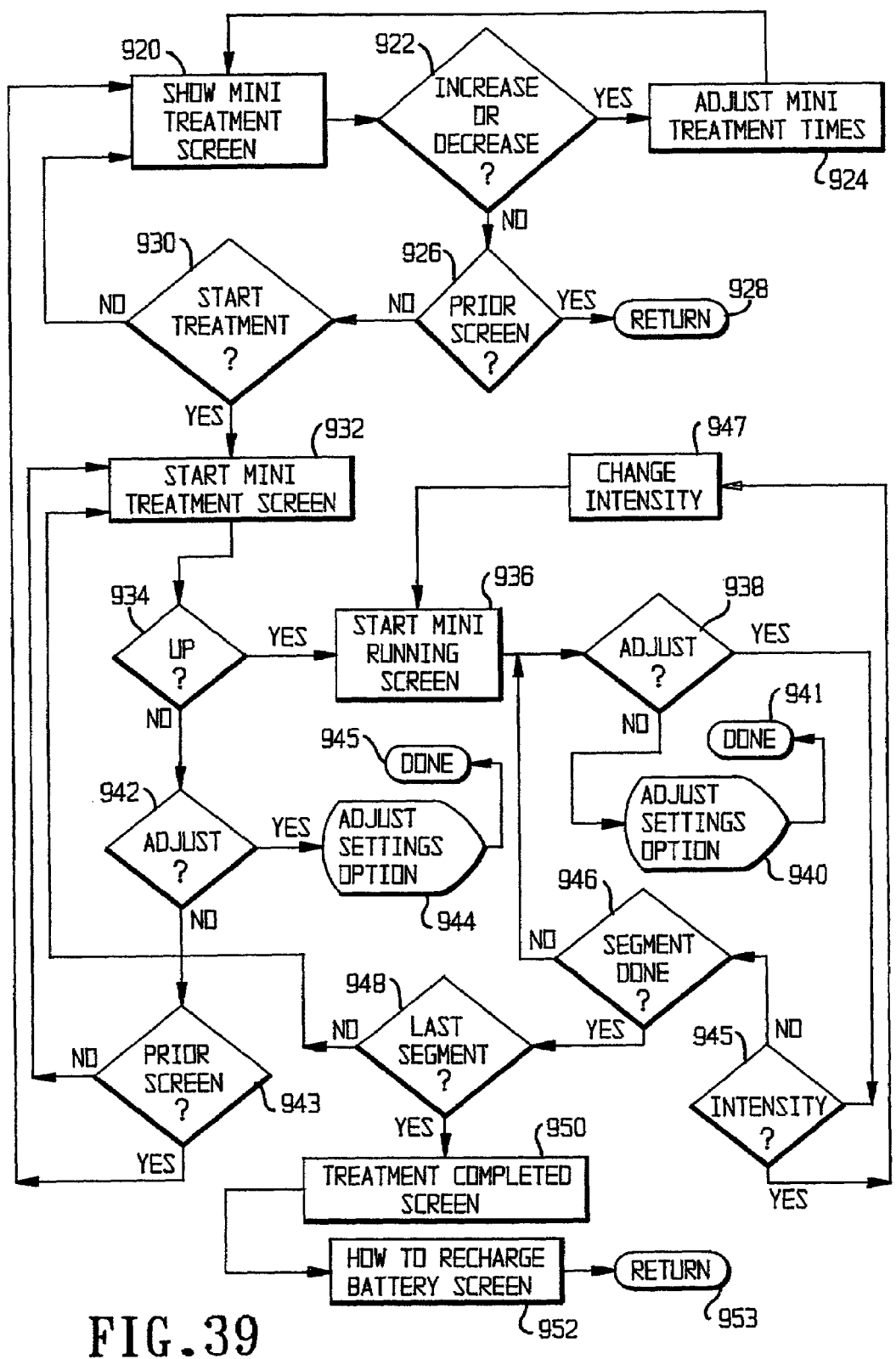

In step 798, the control routine transfers control of the device to the control routine that is outlined in the flow chart of FIG. 39 and continues to step 799. In step 799, the control routine returns control of the device to the control routine that called the advanced options control routine of FIG. 32. If, however, in step 796 the control routine determines that the "setup mini treatment" button has not been touched, then the control routine continues to step 800. In step 800, the control routine determines whether the "start treatment" button has been touched on the touch screen. If, in step 800, the control routine determines that the "start treatment" button has been touched, then the control routine continues to step 802. In step 802, the control routine sets the state of the device to "start segment" and transfers control of the device to the control routine outlined in the flow chart of FIG. 16 and continues to step 803. In step 803, the control routine returns control of the device to the control routine that called the advanced options control routine of FIG. 32. If, however, in step 800, the control routine determines that the "start treatment" button has not been touched, then the control routine returns to step 786.

Figure 33:
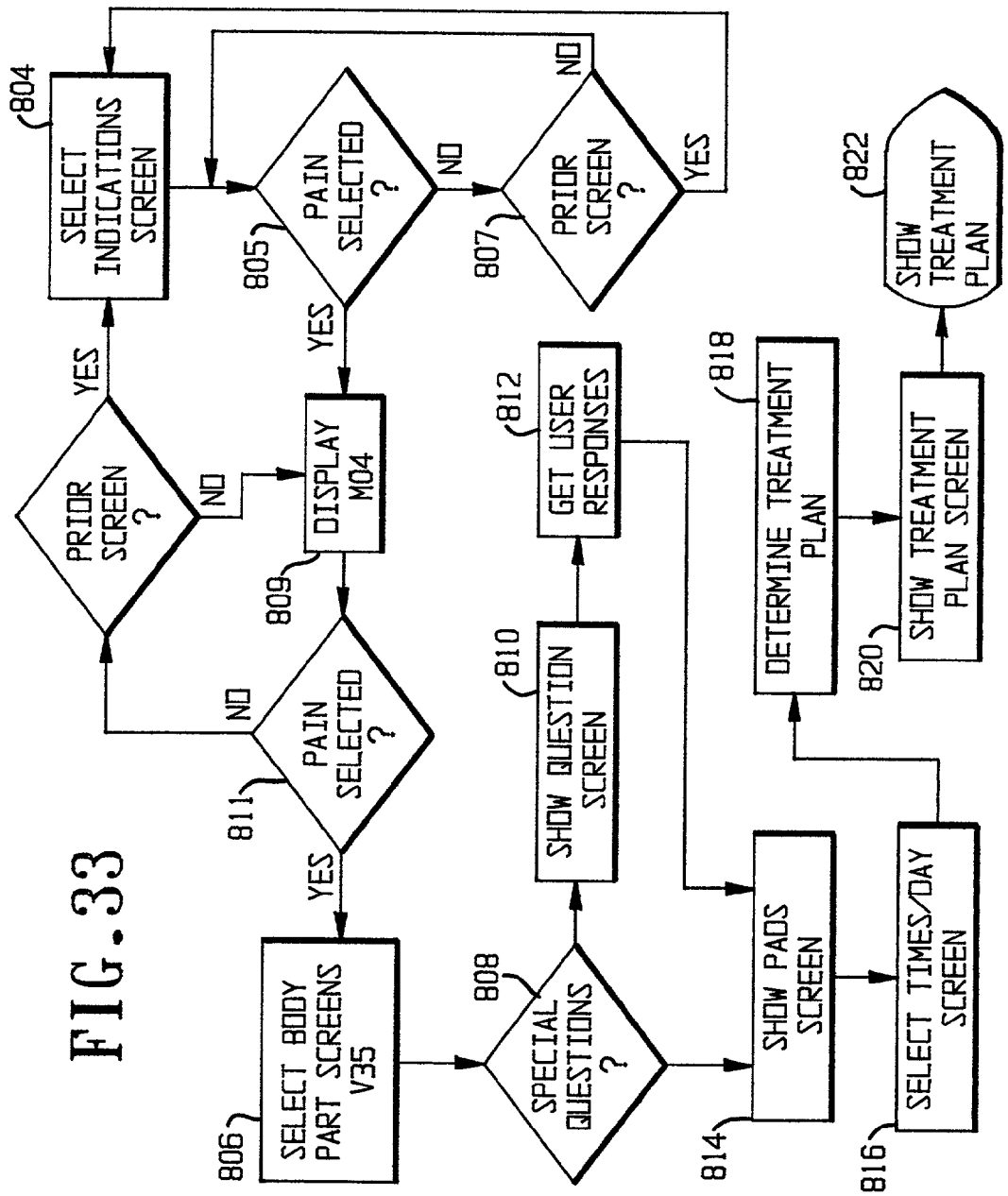
Figure 76:
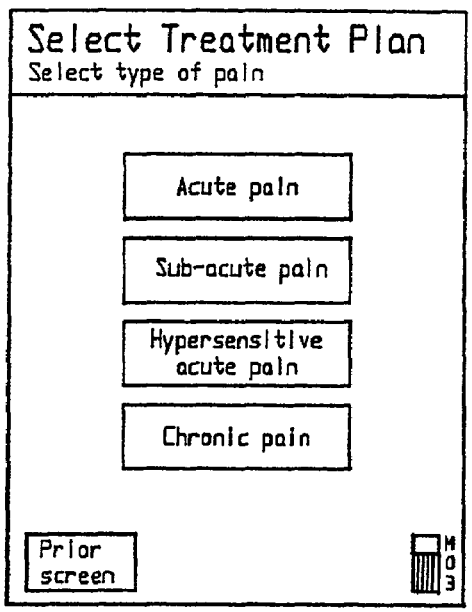

FIG. 33 shows a flow chart that outlines the select treatment plan control routine of an exemplary embodiment of the device in accordance with the present invention. The control routine starts at step 804 where the control routine displays a "Select Treatment Plan—Select Type of Pain" screen, an example of which is shown in FIG. 76, and continues to step 805. In step 805, the control routine determines whether one of the "acute pain," "sub-acute pain," "hyper sensitive acute pain" and "chronic pain" buttons have been touched on the touch screen. If, in step 805, the control routine determines that none of these four buttons have been touched, then the control routine continues to step 807. In step 807, the control routine determines whether the "Prior screen" button on the touch screen has been touched. If, in step 807, the control routine determines that the "Prior screen" button has been touched, then the control routine returns to step 804. If, however, in step 807, the control routine determines that the "Prior screen" button has not been touched, then the control routine returns to step 805.

Figure 77:
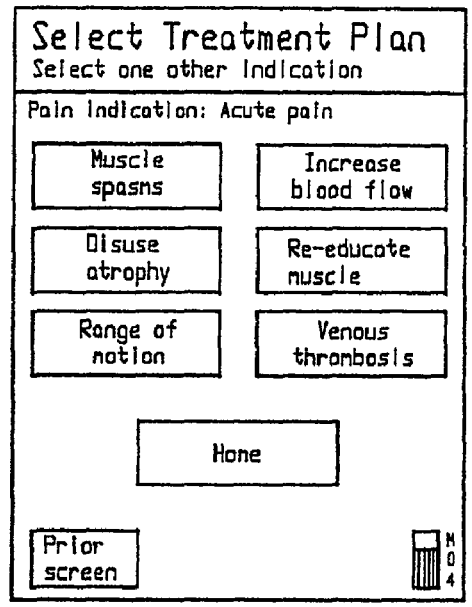
Figure 78:
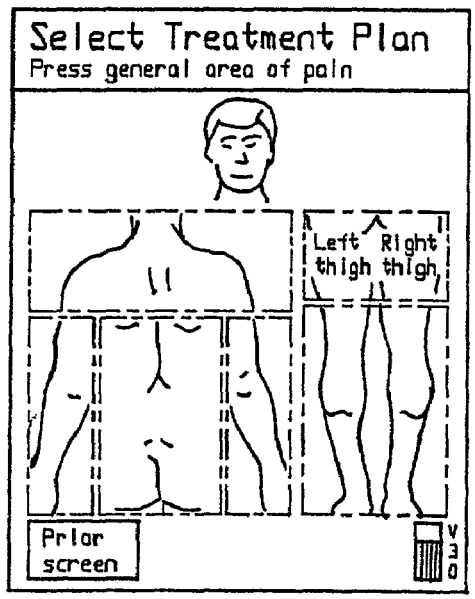
Figure 79:
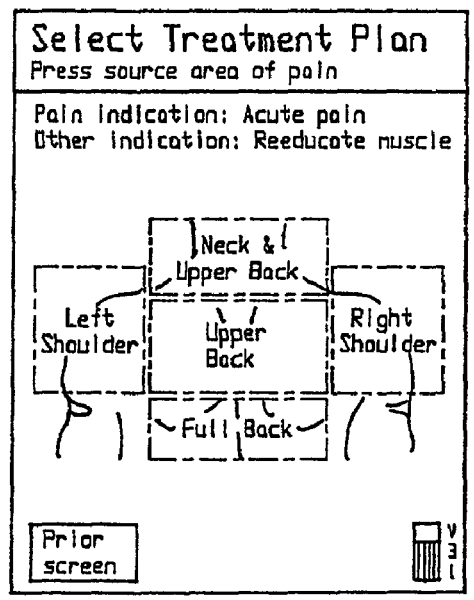
Figure 84:
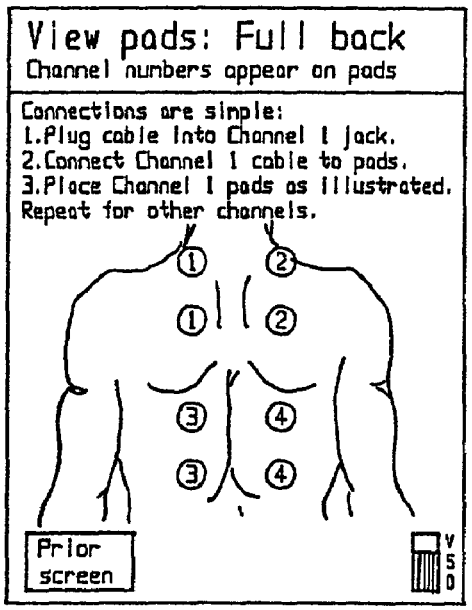
Figure 85:
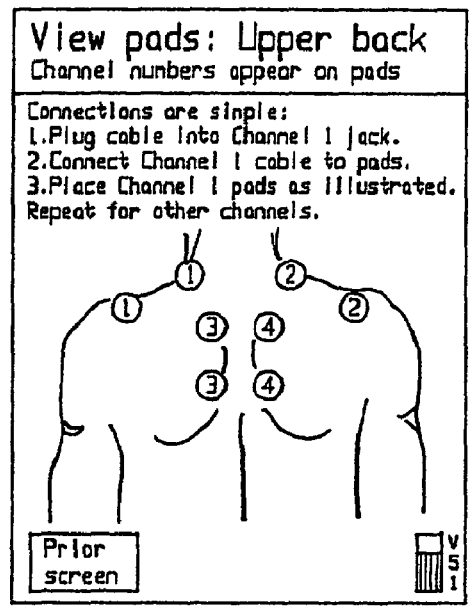
Figure 86:
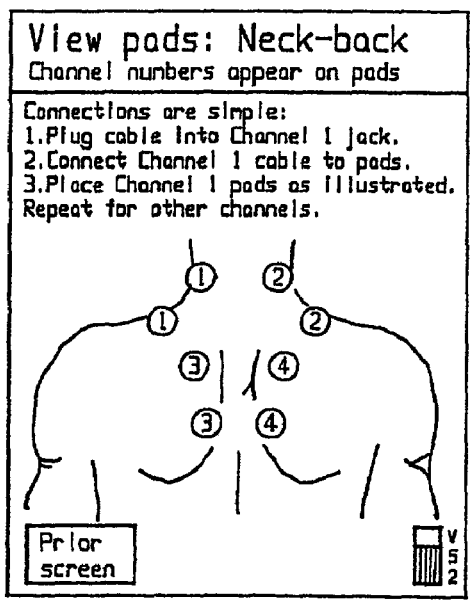
Figure 87:
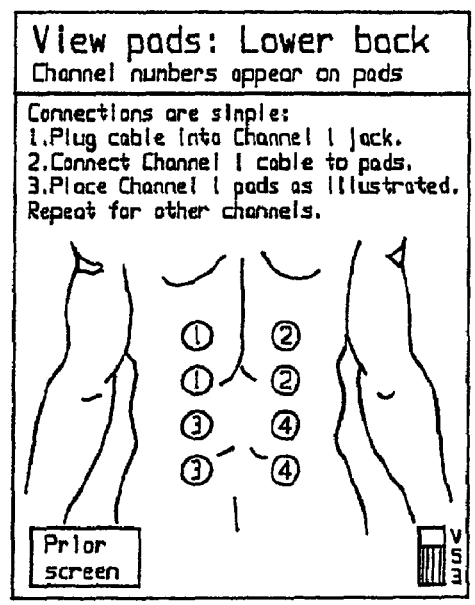
Figure 88:
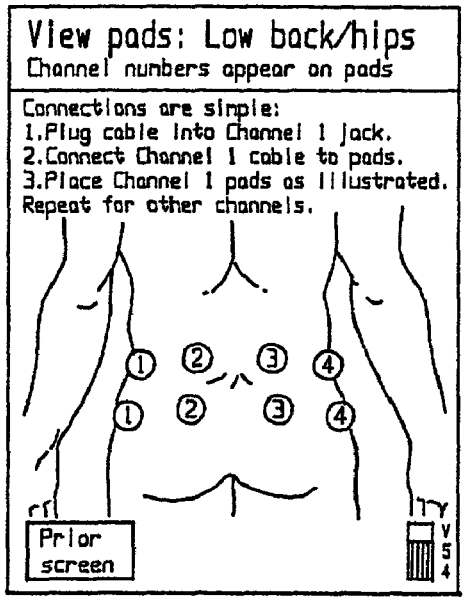
Figure 89:
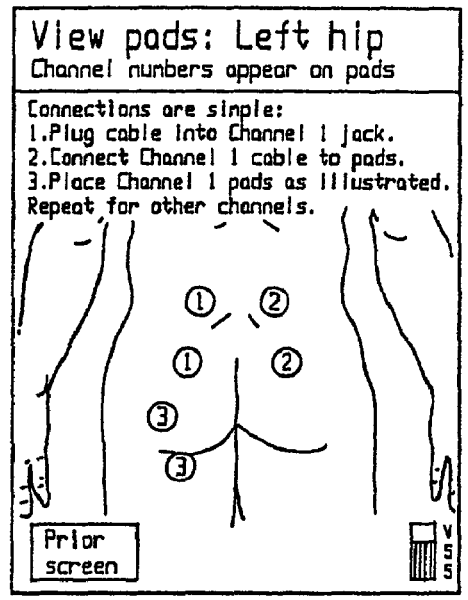
Figure 90:
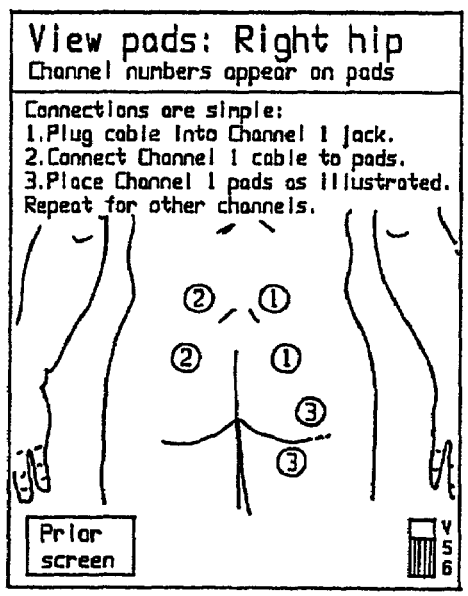
Figure 91:
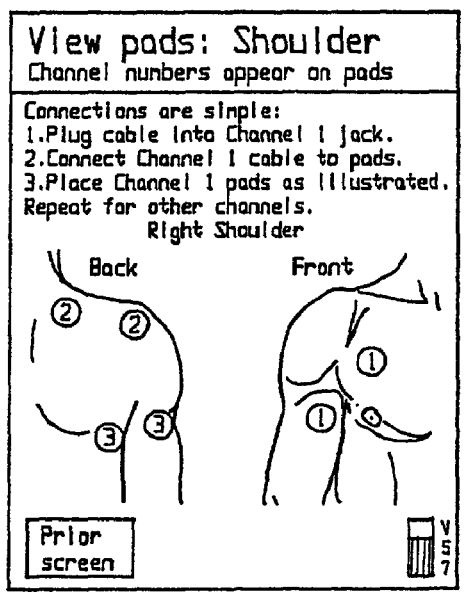
Figure 92:
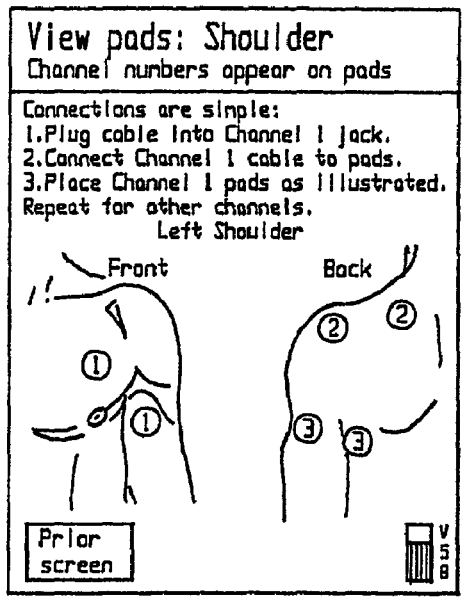
Figure 93:
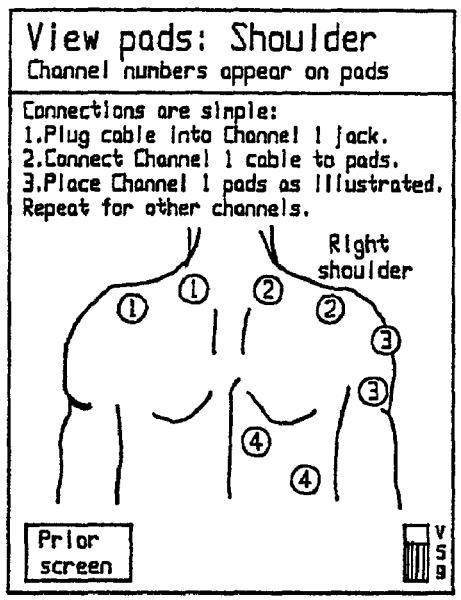
Figure 94:
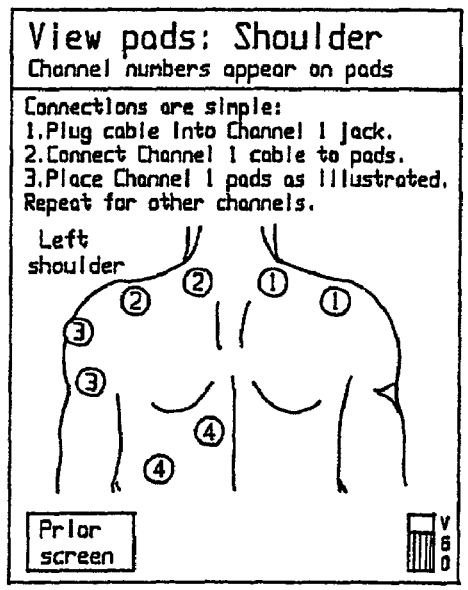
Figure 95:
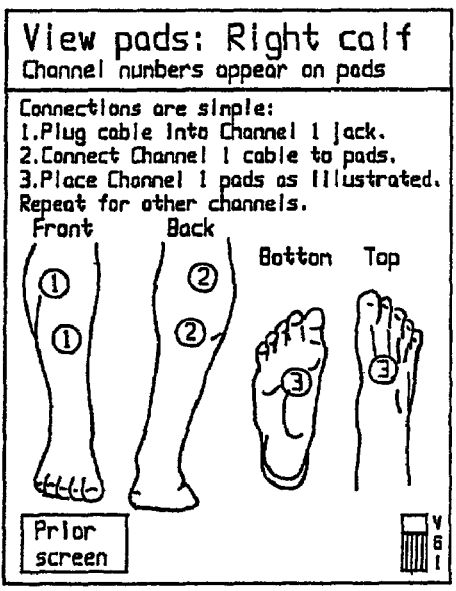
Figure 96:
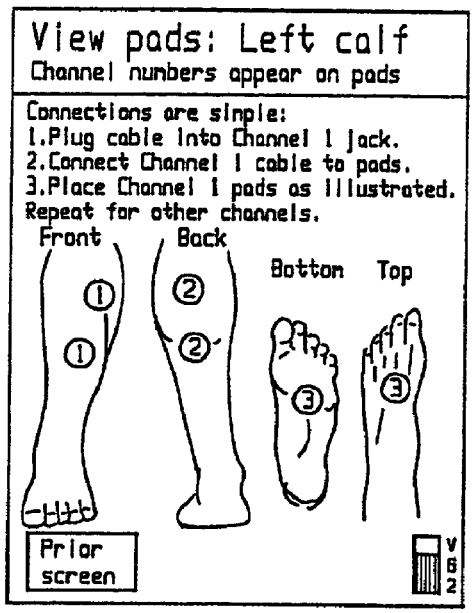
Figure 97:
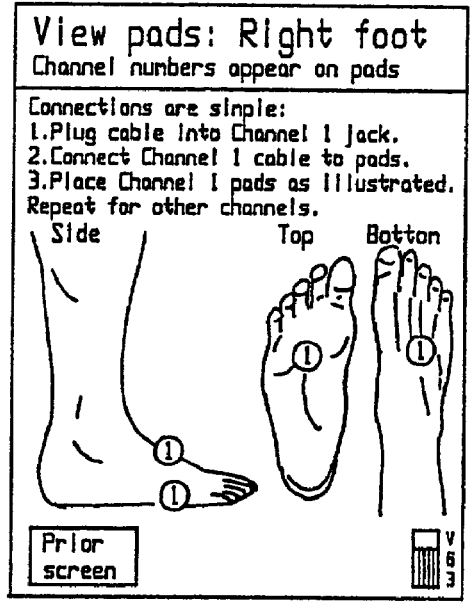
Figure 98:
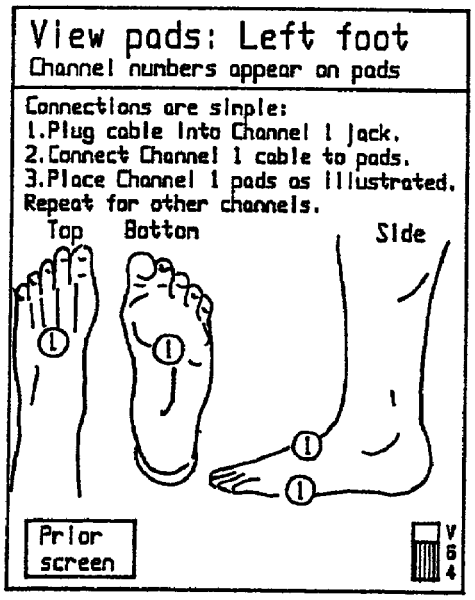
Figure 99:
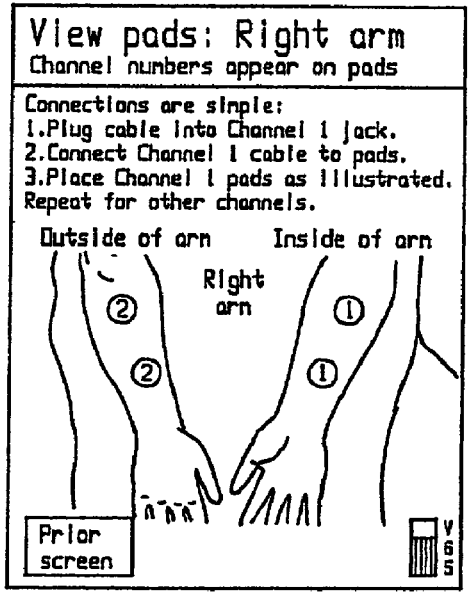
Figure 104:
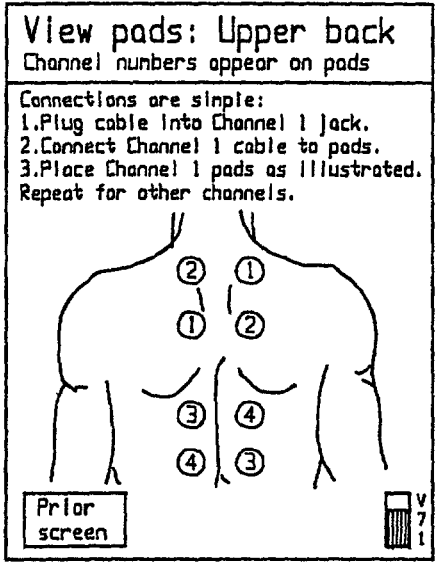
Figure 105:
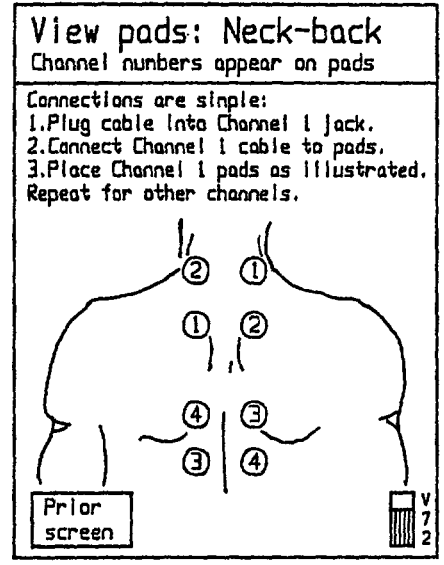
Figure 106:
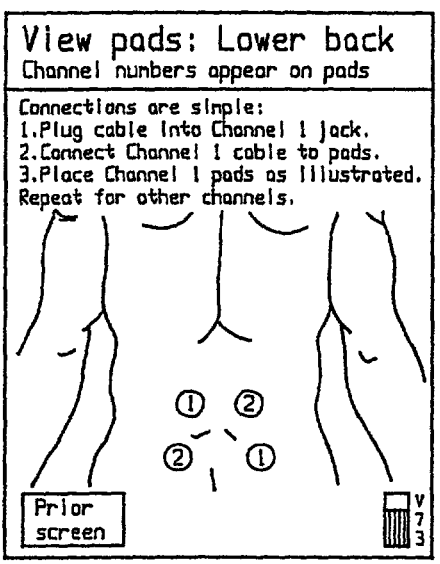
Figure 107:
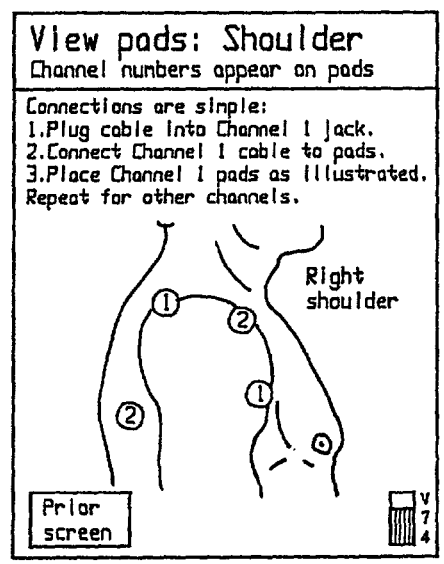
Figure 108:
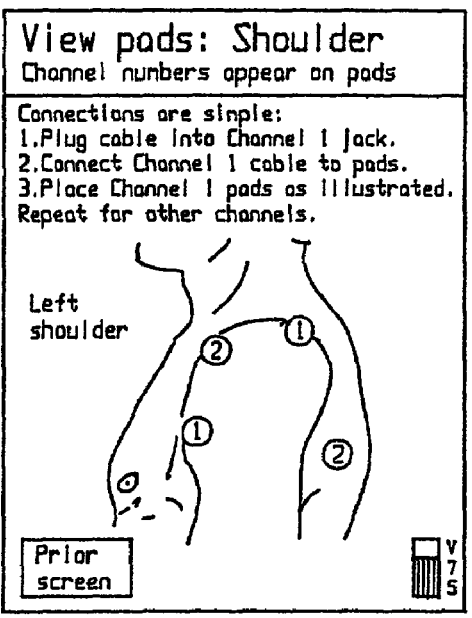
Figure 109:
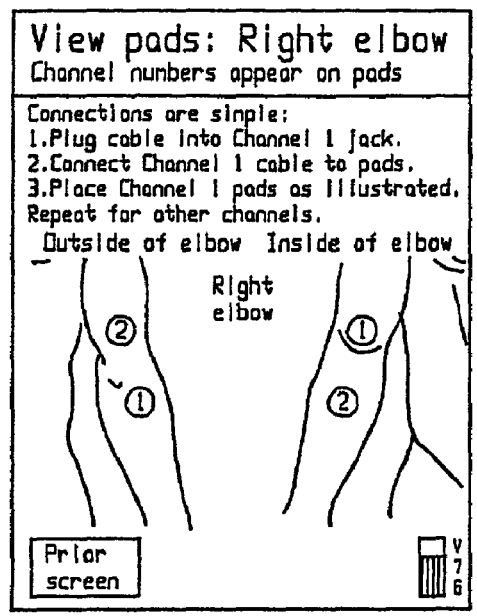
Figure 110:
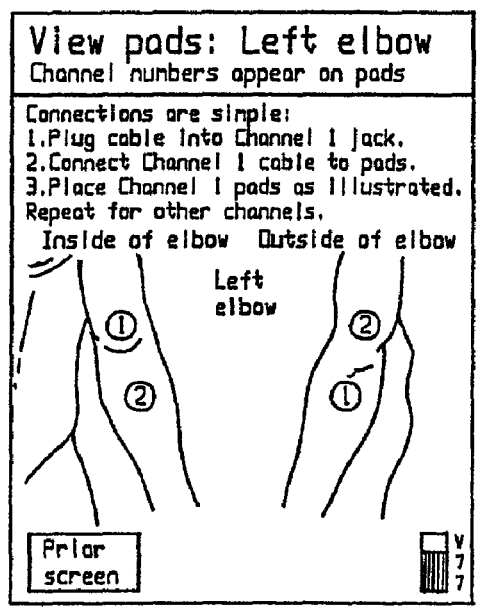
Figure 111:
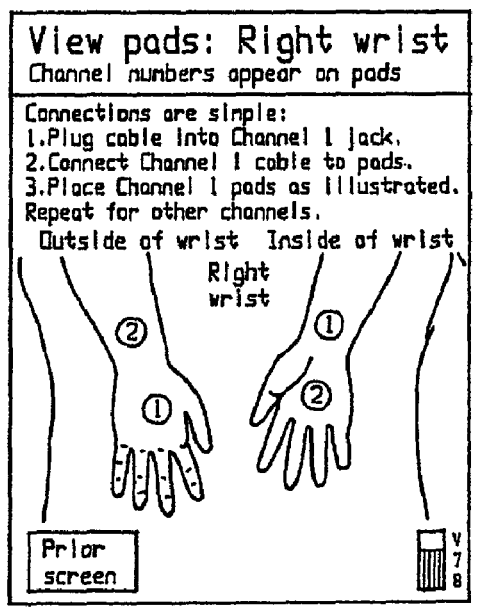
Figure 112:
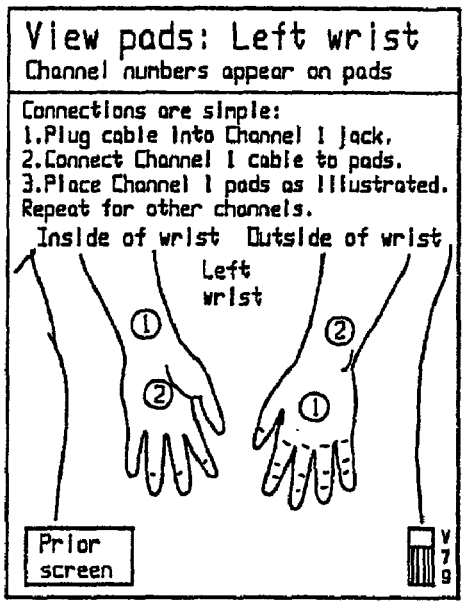
Figure 113:
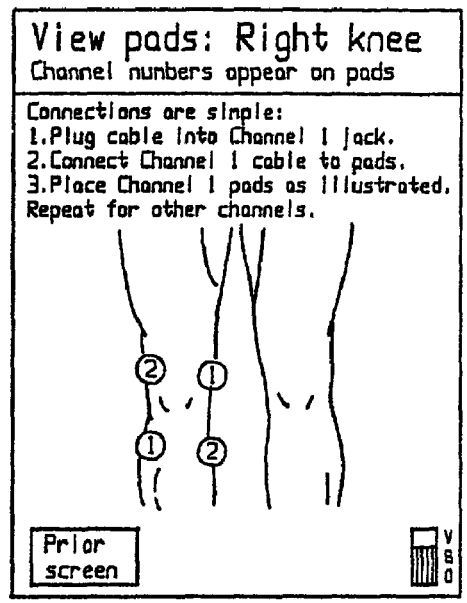
Figure 114:
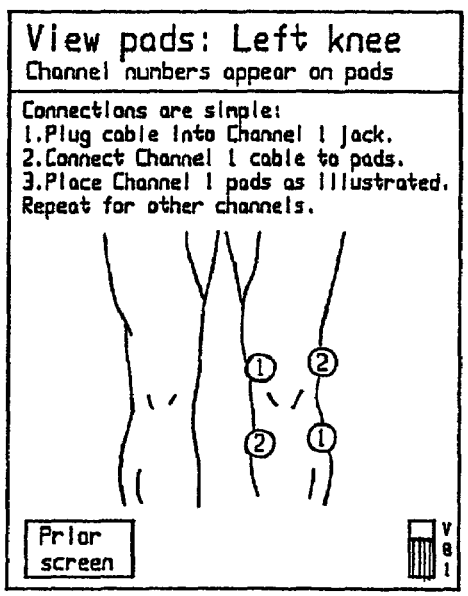
Figure 115:
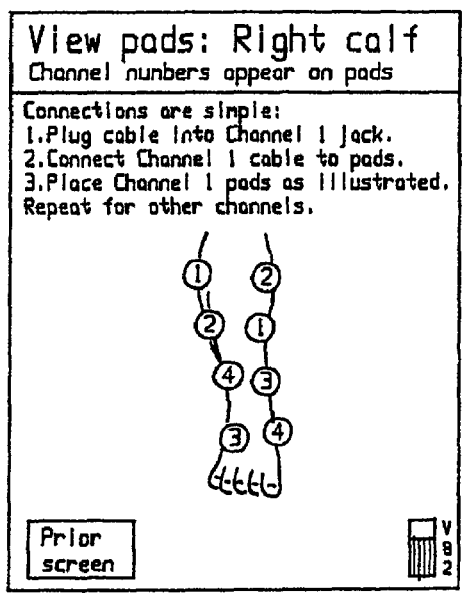
Figure 116:
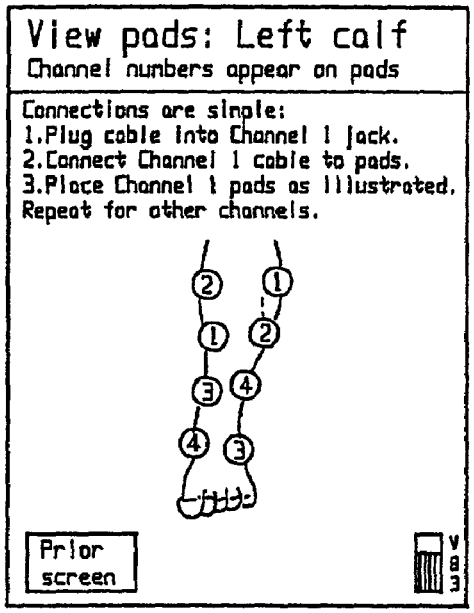
Figure 117:
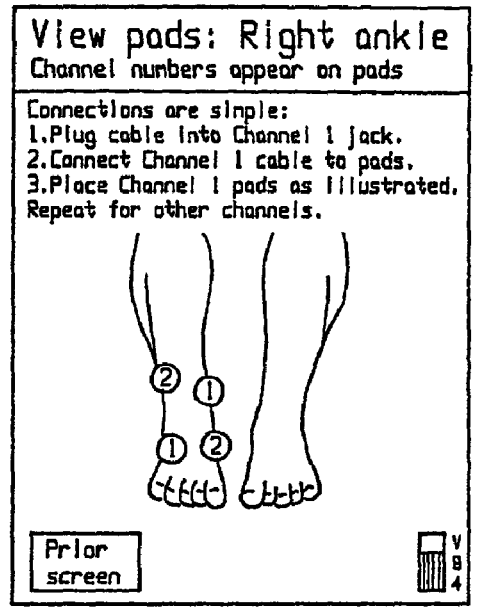
Figure 118:
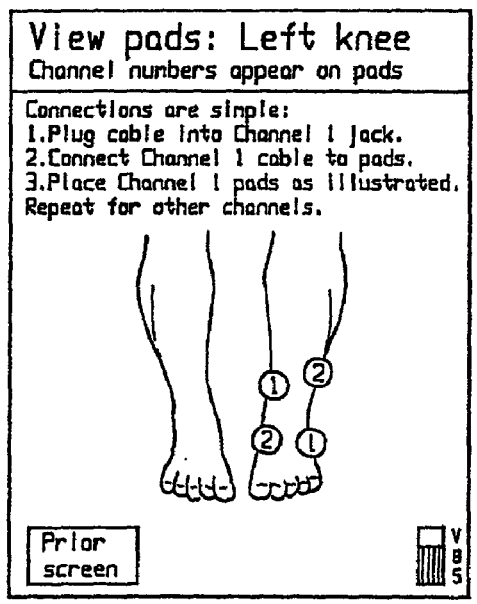
Figure 119:
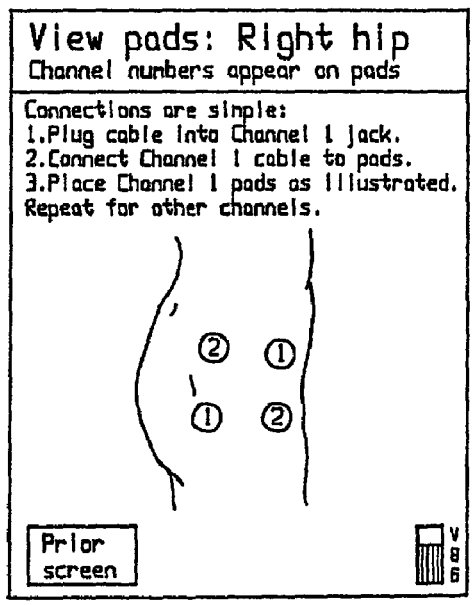

If, however, in step 805, the control routine determines that one of those four buttons has been touched, then the control routine continues to step 809. In step 809, the control routine displays a "Select Treatment Plan—Select one other indication" display, an example of which is shown in FIG. 77 and continues to step 811. In step 811, the control routine determines whether one of the "muscle spasms," "increase blood flood," "disuse atrophy," "reeducate muscle," "range and motion," and "venous thrombosis" buttons or the "none" button is touched. If, in step 811, the control routine determines that any of those buttons has been touched, then the control routine continues to step 806. If, however, the control routine determines that none of those buttons has been touched, then the control routine continues to step 813. In step 813, the control routine determines if the "Prior screen" button has been touched. If, in step 813, the control routine determines that the "Prior screen" button has been touched then the control routine returns to step 804. If, however, in step 813, the control routine determines that the prior screen button has not been touched then the control routine returns to step 809.

In step 806, the control routine determines the area of pain that is to be treated by sequentially displaying appropriate body part displays, examples of which are shown in FIGS. 78–82 and 155, and requesting and receiving indications from the user. The control routine then continues to step 808. In step 808, the control routine determines if there is a special question that the device needs to have answered to further determine correct pad placement. If, in step 808, the control routine has a special question, then the control routine continues to step 810. In step 810, the control routine displays a "Select Treatment Plan—Answer question" screen, an example of which is shown in FIG. 83, and continues to step 812. In step 812, the control routine receives the user's response to the special question and continues to step 814. If, however, at step 808, the control routine determines that the device does not have a special question, then the control routine continues to step 814.

In step 814, the control routine displays one of the appropriate view pad screens, examples of which are shown in FIGS. 84–120, and continues to step 816. In step 816, the control routine displays a "Select Treatment Plan—Select frequency of treatment" screen, an example of which is shown in FIG. 121, receives the user selected frequency of treatment and continues to step 818. In step 818, the control routine determines an appropriate treatment plan based upon the pain indication, other indications and pad placement and continues to step 820. In step 820, the control routine displays a "Select Treatment Plan—Review plan" screen, an example of which is shown in FIG. 122, and continues to step 822. In step 822, the control routine transfers control of the device to the control routine outlined in the flow chart shown in FIG. 34 and continues to step 823. In step 823, the control routine returns control of the device to the control routine that called the select treatment plan control routine of FIG. 33.

Figure 34:
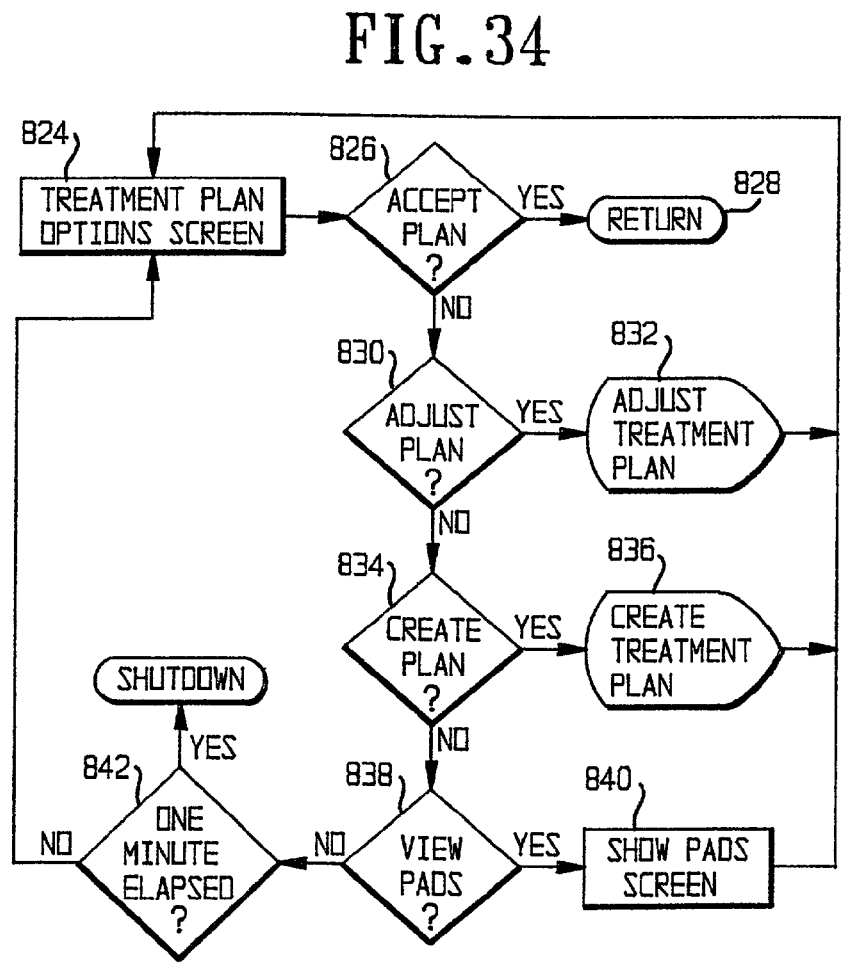
FIGS. 9–39 show flowcharts of the control routines of an exemplary embodiment of a multi-functional portable electro-medical device in accordance with the present invention.

FIG. 34 shows a flow chart that outlines the show treatment plan control routine in accordance with an exemplary embodiment of the invention. The control routine starts at step 824 where the control routine displays a "Select Treatment Plan—Review plan" screen, an example of which is shown in FIG. 122, and continues to step 826. In step 826, the control routine determines whether the "Accept" button on the touch screen has been touched. If, in step 826, the control routine determines that the "Accept" button has been touched, then the control routine continues to step 828. In step 828, the control routine returns control of the device to the control routine that called the show treatment plan control routine of FIG. 34. If, however, in step 826, the control routine determines that the "Accept" button has not been touched, then the control routine continues to step 830.

In step 830, the control routine determines whether the "Adjust Plan" button has been touched. If, in step 830, the control routine determines that the "Adjust Plan" button has been touched, then the control routine continues to step 832. In step 832, the control routine transfers control of the device to the control routine outlined in the flow chart of FIG. 35 and returns to step 824. If, however, in step 830, the control routine determines that the "Adjust Plan" button has not been touched, then the control routine continues to step 834. In step 834, the control routine determines whether the "Create Plan" button has been touched on the touch screen. If, in step 834, the control routine determines that the "Create Plan" button has been touched, then the control routine continues to step 836. In step 836, the control routine transfers control of the device to the create treatment plan control routine that is outlined in the flow chart of FIG. 38 and returns to step 824. If, however, in step 834, the control routine determines that the "Create Plan" button has not been touched, then the control routine continues to step 838.

If, in step 838, the control routine determines that the "View pads" button has been touched, then the control routine continues to step 840. In step 840, the control routine displays a "View pads" screen, examples of which are shown in FIGS. 84–120, and returns to step 824. If, however, the control routine determines that the "View pads" button has not been touched, then the control routine continues to step 842. In step 842, the control routine determines if one minute has elapsed. If, in step 842; the control routine determines that one minute has not elapsed, then the control routine returns to step 824. If, however, the control routine determines in step 842 that one minute has elapsed, then the control routine shuts down the device.

Figure 35:
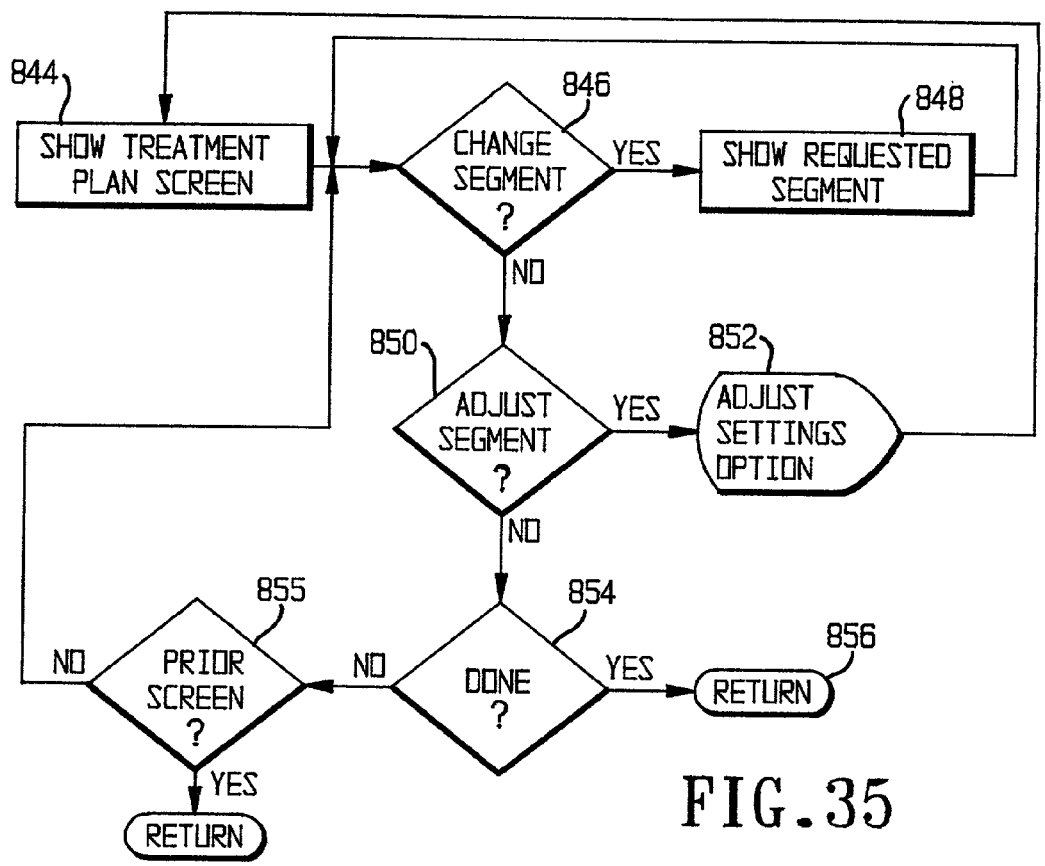

FIG. 35 shows a flowchart that outlines an adjust treatment plan control routine. The control routine starts at step 844 where the control routine either displays an "adjust treatment settings" screen, an example of which is shown in FIG. 123, or a "create treatment plan" screen, an example of which is shown in FIG. 124, as appropriate, and continues to step 846. In step 846, the control routine determines whether the segment is being changed based upon whether a segment button on the touch screen is touched. If, in step 846, the control routine determines that the segment is being changed, then the control routine continues to step 848. In step 848, the control routine shows the requested segment and returns to step 846. If, however, in step 846 the control routine determines that the segment is not being changed, then the control routine continues to step 850.

In step 850, the control routine determines whether the "Adjust" button on the touch screen has been touched. If, in step 850, the control routine determines that the "Adjust" button has been touched, then the control routine continues to step 852. In step 852, the control routine transfers control of the device to the control routine outlined in the flow chart of FIG. 36 and returns to step 844. If, however, the control routine determines that the "Adjust" button has not been touched, then the control routine continues to step 854. In step 854, the control routine determines whether the "Done" button has been touched. If, in step 854, the control routine determines that the "Done" button has been touched, then the control routine continues to step 856. In step 856, the control routine returns to the control routine that called the adjust treatment plan control routine of FIG. 35. If, however, in step 854, the control routine determines that the "Done" button has not been touched, then the control routine continues to step 855.

In step 855, the control routine determines whether the "Prior screen" button has been touched. If, in step 855, the control routine determines that the "Prior screen" button has been touched, then the control routine returns control of the device to the control routine that called the adjust treatment plan control routine outlined in the flow chart of FIG. 35. If, however, in step 855, the control routine determines that the "Prior screen" button has not been touched, then control routine returns to step 846.

Figure 36:
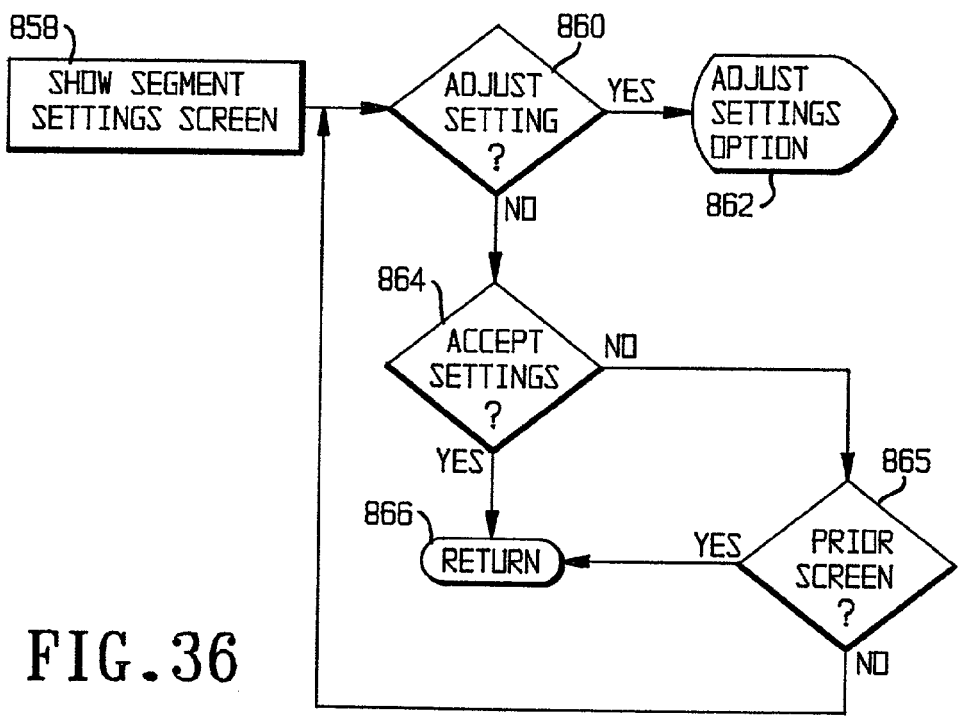

FIG. 36 shows a flow chart that outlines the adjust segment option control routine of an exemplary embodiment of the present invention. The control routine starts at step 858 where the control routine displays an "adjust treatment settings" screen, examples of which are shown in FIGS. 125–126, and continues to step 860. In step 860, the control routine determines whether the user has touched one of the "Adjust" buttons on the touch screen. If, in step 860, the control routine determines that the user has touched one of the "Adjust" buttons, then the control routine continues to step 862. In step 862, the control routine transfers control of the device to the adjust settings control routine outlined in the flow chart of FIG. 37 and returns to step 858. If, however, in step 860, the control routine determines that the "Adjust" buttons have not been touched, then the control routine continues to step 864.

In step 864, the control routine determines whether the "Accept" button has been touched on the touch screen. If, in step 864, the control routine determines that the "Accept" button has not been touched, then the control routine continues to step 865. In step 865, the control routine determines whether the "Prior screen" button has been touched on the touch screen. If, in step 865, the control routine determines that the "Prior screen" button has been touched on the touch screen then the control routine continues to step 866. If, however, in step 865, the control routine determines that the "Prior screen" button has not been touched, then the control routine returns to step 860. If, however, in step 864, the control routine determines that the "Accept" button has been touched, then the control routine continues to step 866. In step 866, the control routine returns control of the device to the control routine that called the adjust segment option control routine of FIG. 36.

Figure 37:
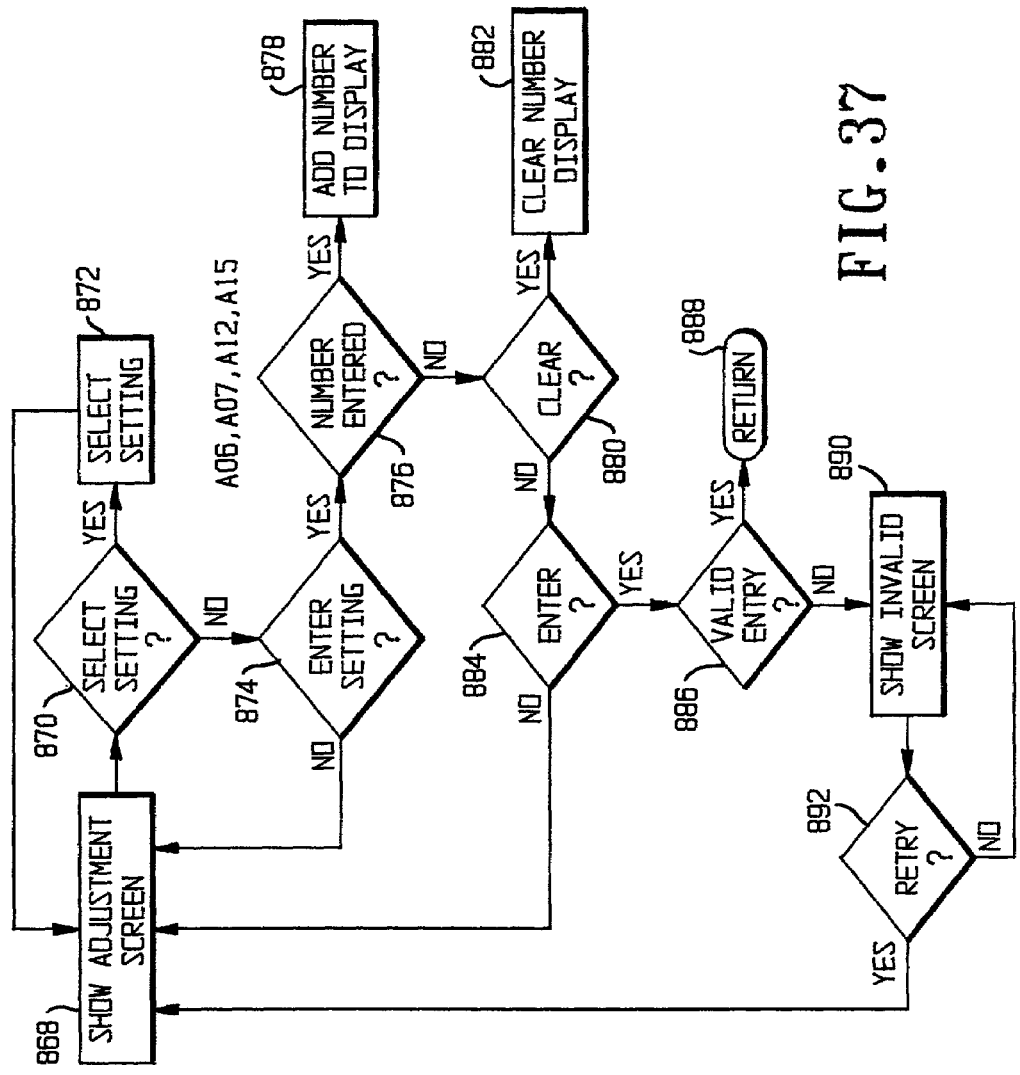

FIG. 37 shows a flow chart that outlines the adjust settings option control routine in accordance with the exemplary embodiment of the present invention. The control routine starts at step 868 where the control routine displays an "Adjust treatment settings" screen, examples of which are shown in FIGS. 127–134, and continues to step 870. In step 870, the control routine determines whether a setting has been selected by a user. If, in step 870, the control routine determines that a setting has been selected, then the control routine continues to step 872. In step 872, the control routine sets the selected setting and returns to step 868.

If, however, in step 870, the control routine determines that a setting has not been selected, then the control routine continues to step 874. In step 874, the control routine determines whether a setting has been entered. If, in step 874, the control routine determines that a setting has not been entered, then the control routine returns to step 868. If, however, in step 874, the control routine determines that a setting has been entered, then the control routine continues to step 876. In step 876, the control routine determines whether a number has been entered. If, in step 876, the control routine determines that a number has been entered, then the control routine continues to step 878. In step 878, the control routine adds the entered number to the display and returns to step 868. If, however, in step 876, the control routine determines that a number has not been entered, then the control routine continues to step 880.

In step 880, the control routine determines whether the "clear" button has been touched on the touch screen. If, in step 880, the control routine determines that the "clear" button has been touched, then the control routine continues to step 882. In step 882, the control routine clears the number from the display and returns to step 868. If, however, in step 880, the control routine determines that the "clear" button has not been touched on the touch screen, then the control routine continues to step 884. In step 884, the control routine determines whether the "enter" button has been touched on the touch screen. If, in step 884, the control routine determines that the "enter" button has not been touched, then the control routine returns to step 868. If, however, in step 884, the control routine determines that the "enter" button has been touched on the touch screen, then the control routine continues to step 886. In step 886, the control routine determines whether the entry is valid. If, in step 886, the control routine determines that the entry is valid, then the control routine continues to step 888. In step 888, the control routine returns control of the device to the control routine that called the adjust settings option control routine of FIG. 37.

Figure 151:
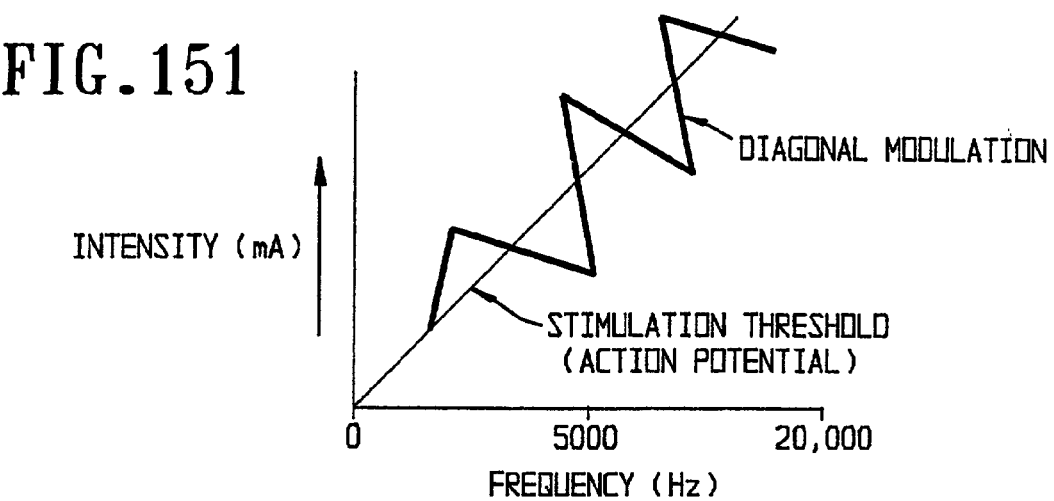
FIG. 151 is a chart illustrating diagonal modulation therapy stimulation in accordance with the present invention.

If, however, in step 886, the control routine determines that the entry is not valid, then the control routine continues to step 890. In step 890, the control routine displays an "Alert— invalid entry" screen, an example of which is shown in FIG. 151 and continues to step 892. In step 892, the control routine determines whether the "Retry" button has been touched on the touch screen. If, in step 892, the control routine determines that the "Retry" button has not been touched, then the control routine returns to step 890. If, however, in step 892, the control routine determines that the "Retry" button has been touched, then the control routine returns to step 868.

Figure 38:
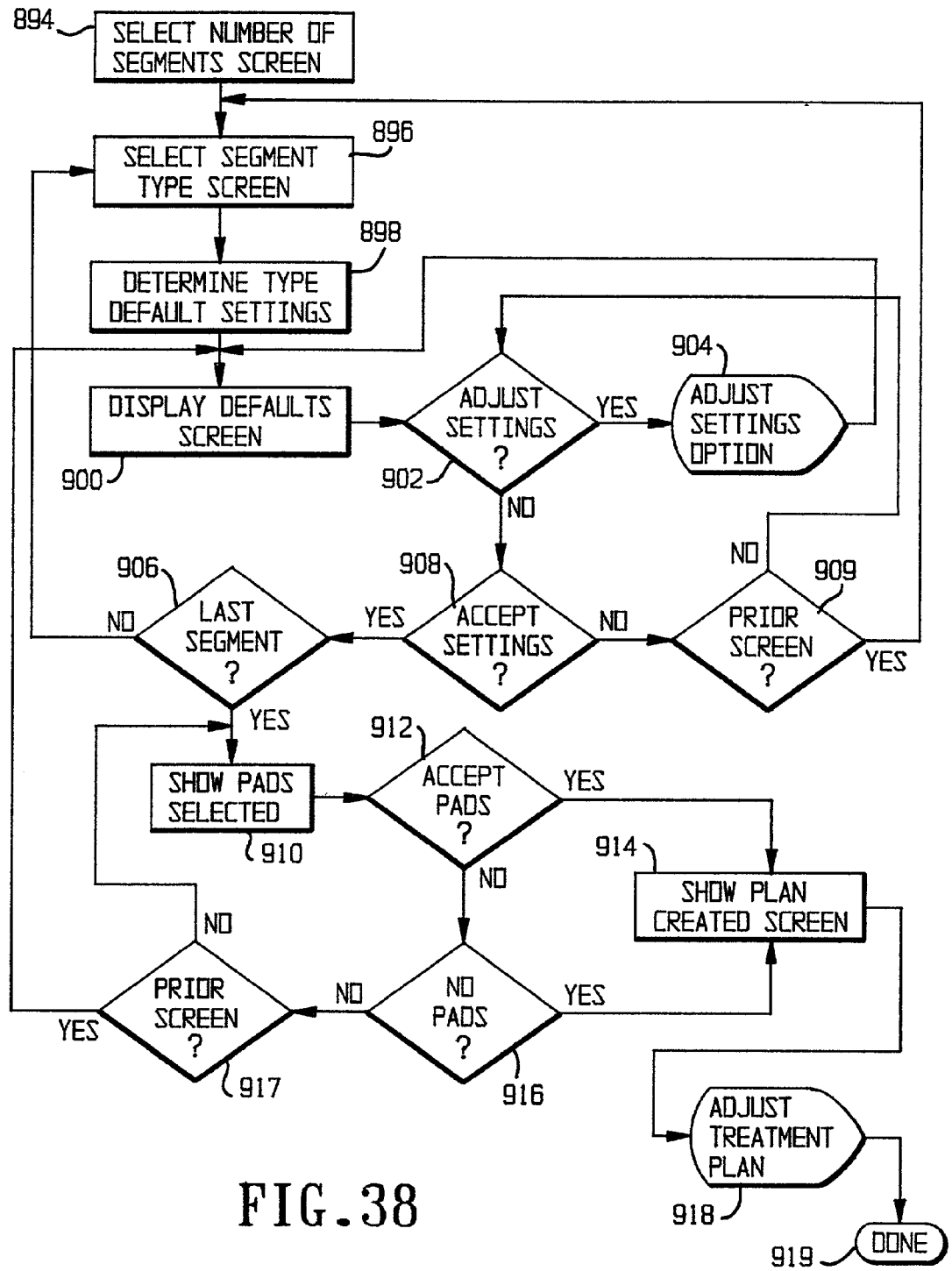
Figure 135:
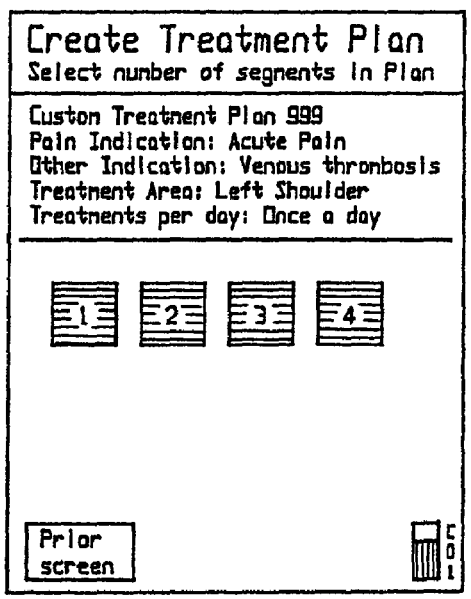
Figure 136:

FIG. 38 shows a flow chart that outlines a create treatment plan of an exemplary embodiment in accordance with the present invention. The control routine starts at step 894 where the control routine displays a "Create Treatment Plan—Select number of segments in Plan" screen, an example of which is shown in FIG. 135, receives a user input selection for a number of segments in the plan and continues to step 896. In step 896, the control routine displays a "Create Treatment Plan—Select treatment type for segment 1" screen, an example of which is shown in FIG. 136, receives the selected treatment type from the user and continues to step 898. In step 898, the control routine determines the type default settings and continues to step 900.

Figure 137:
Figure 138:

In step 900, the control routine displays a "Create Treatment Plan" screen, examples of which are shown in FIGS. 137 and 138, and continues to step 902. In step 902, the control routine determines whether an "Adjust" button has been touched on the touch screen. If, in step 902, the control routine determines that an "Adjust" button has been touched, then the control routine continues to step 904. In step 904, the control routine transfers control of the device to the control routine that is outlined in FIG. 37 and returns to step 900. If, however, in step 902, the control routine determines that an "Adjust" button has not been touched, then the control routine continues to step 908. In step 908, the control routine determines whether an "Accept" button has been touched on the touch screen. If, in step 908, the control routine determines that the "Accept" button has not been touched, then the control routine continues to step 909.

In step 909, the control routine determines whether the "Prior screen" button has been touched. If, in step 909, the control routine determines that the "Prior screen" button has been touched, then the control routine returns to step 896. If, however, in step 909 the control routine determines that the "Prior screen" button has not been touched, then the control routine returns to step 902. If, however, in step 908, the control routine determines that the "Accept" button has been touched, then the control routine continues to step 906. In step 906, the control routine determines whether the current segment is the last segment in the treatment plan. If, in step 906, the control routine determines that this is not the last segment in the treatment plan, then the control routine returns to step 896. If, however, in step 906, the control routine determines that this is the last segment in the treatment plan, then the control routine continues to step 910.

Figure 150:

In step 910, the control routine displays a "Create Treatment Plan—Review pad layout" screen, an example of which is shown in FIG. 150 and continues to step 912. In step 912, the control routine determines whether the "Accept" button has been touched on the touch screen. If, in step 912, the control routine determines that the "Accept" button has been touched on the touch screen, then the control routine continues to step 914. In step 914, the control routine shows a "Create Treatment Plan" screen, an example which is shown in FIG. 124, and continues to step 918. If, however, in step 912, the control routine determines that the "Accept" button has not been touched, then the control routine continues to step 916. In step 916, the control routine determines whether the "No pads screen" button has been touched on the touch screen. If, in step 916, the control routine determines that the "no pad" screen button has touched, then the control routine continues to step 917.

In step 917, the control routine determines whether the "Prior screen" button has been touched on the touch screen. If, in step 917, the control routine determines that the "Prior screen" button has been touched, then the control routine returns to step 900. If, however, in step 917, the control routine determines that the "Prior screen" button has not been touched, then the control routine returns to step 910. If, however, in step 916, the control routine determines that the "no pad" button has been touched, then the control routine continues to step 914. In step 918, the control routine transfers control of the device to the control routine outlined in the flow chart shown in FIG. 35 and continues to step 919. In step 919, the control routine returns control to the control routine that called the create treatment plan control routine of FIG. 38.

Figure 139:
Figure 140:
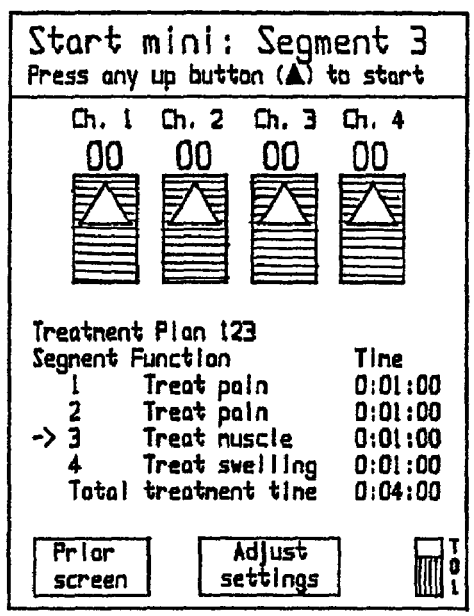
Figure 141:
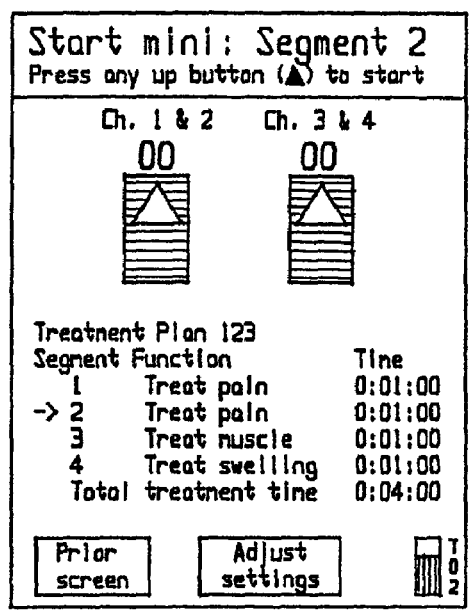
Figure 142:
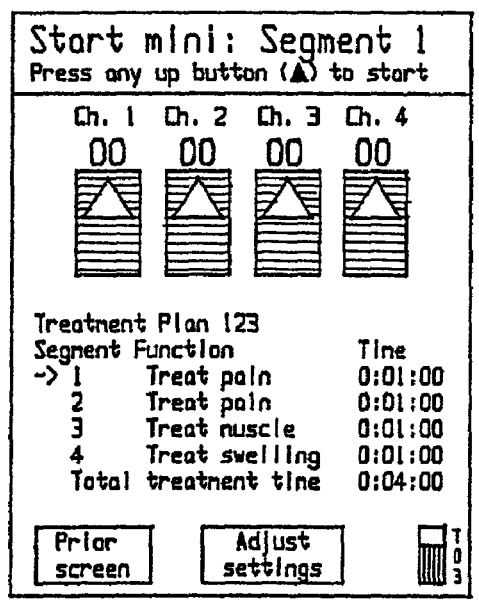
Figure 143:
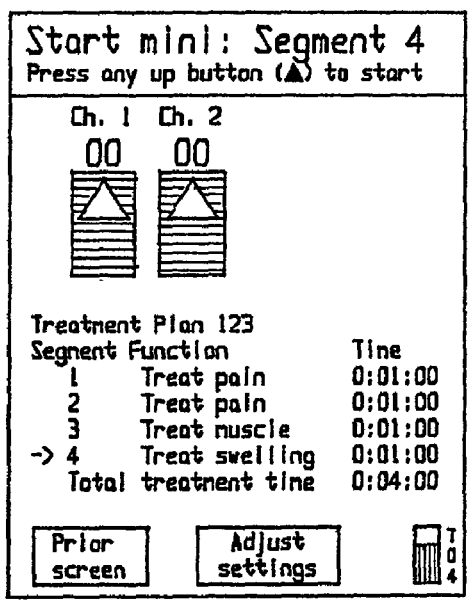
Figure 144:
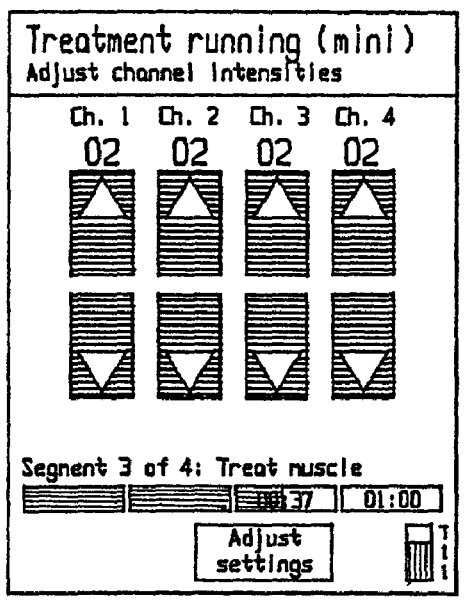
Figure 145:
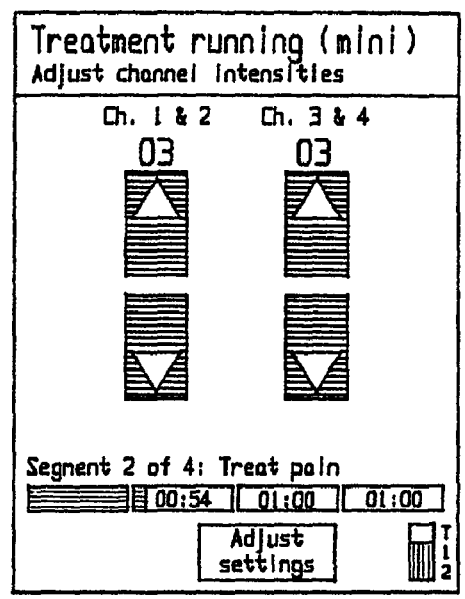
Figure 146:
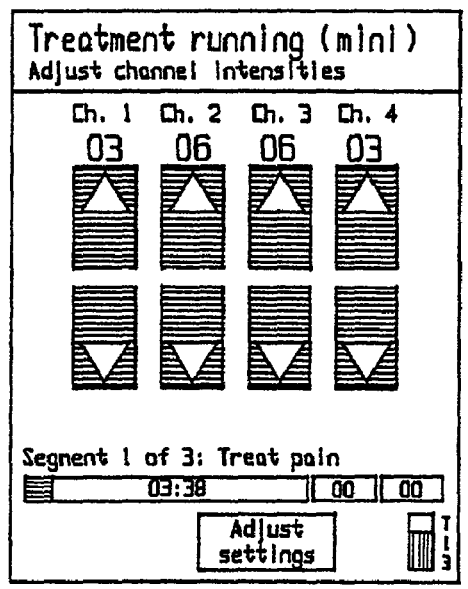
Figure 147:
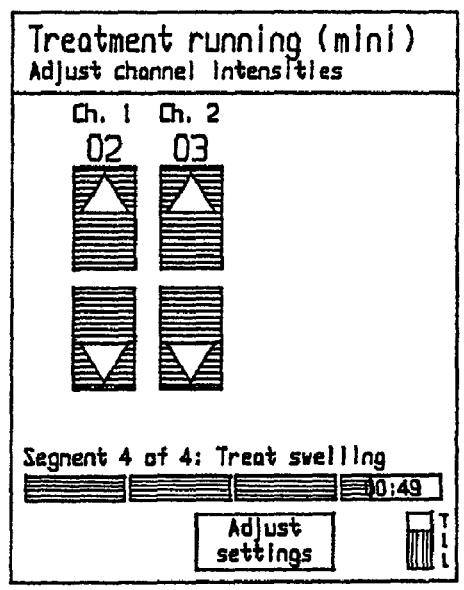

FIG. 39 shows a flow chart that outlines the mini treatment option control routine of an exemplary embodiment in accordance with the present invention. The control routine starts at step 920 where the control routine shows a "Set up mini treatment" screen, an example of which is shown in FIG. 139, and continues to step 922. In step 922, the control routine determines whether an "increase" or "decrease" button has been touched on the touch screen. If, in step 922, the control routine determines that an "increase" or "decrease" button has been touched on the touch screen, then the control routine continues to step 924.

In step 924, the control routine adjusts the mini treatment times in accordance with the "increase" or "decrease" button that has been touched and returns to step 920. If, however, in step 922, the control routine determines that an "increase" or "decrease" button has not been touched, then the control routine continues to step 926. In step 926, the control routine determines whether a "Prior screen" button has been touched on the touch screen. If, in step 926, the control routine determines that a "Prior screen" button has been touched, then the control routine continues to step 928. In step 928, the control routine transfers control of the device back to the control routine that called the mini treatment option control routine of FIG. 39. If, however, in step 926, the control routine determines that the "Prior screen" button has not been touched, then the control routine continues to step 930.

In step 930, the control routine determines whether the "Start treatment" button has been touched. If, in step 930, the control routine determines that the "Start treatment" button has not been touched on the touch screen, then the control routine returns to step 920. If, however, in step 930, the control routine determines that the "Start treatment" button has been touched then the control routine continues to step 932. In step 932, the control routine displays a "Start mini segment" screen, examples of which are shown in FIGS. 140–143, and continues to step 934. In step 934, the control routine determines whether an "up" button has been touched on the touch screen. If, in step 934, the control routine determines that an "up" button has not been touched, then the control routine continues to step 942.

In step 942, the control routine determines whether an "Adjust settings" button has been touched on the touch screen. If, in step 942, the control routine determines that an "Adjust settings" button has been touched on the touch screen, then the control routine continues to step 944. In step 944, the control routine transfers control of the device to the control routine outlined in the flow chart of FIG. 37 and continues to step 945. In step 945, the control routine returns control of the device to the control routine that called the mini treatment option control routine of FIG. 39. If, however, in step 942, the control routine determines that the "Adjust settings" button has not been touched, then the control routine continues to step 943. In step 943, the control routine determines whether the "Prior screen" button has been touched on the touch screen. If, in step 943, the control routine determines that the "Prior screen" button has been touched, then the control routine returns to step 932. If, however, in step 943, the control routine determines that the "Prior screen" button has been touched, then the control routine returns to step 920.

If, however, in step 934, the control routine determines that an "up" button has been touched, then the control routine continues to step 936. In step 936, the control routine displays a "Treatment running" screen, examples of which are shown in FIGS. 144–147, and continues to step 938. In step 938, the control routine determines whether an "Adjust settings" button has been touched on the touch screen. If, in step 938, the control routine determines that an "Adjust settings" button has been touched, then the control routine continues to step 940. In step 940, the control routine transfers control of the device to the control routine that is outlined in the flow chart of FIG. 37 and continues to step 941. In step 941, the control routine returns control of the device to the control routine that called the mini treatment option control routine of FIG. 39. If, however, the control routine determines that the "Adjust settings" button has not been touched, then the control routine continues to step 945.

In step 945, the control routine determines whether an intensity button has been touched on the touch screen. If, in step 945, the control routine determines that an intensity button has been touched, then the control routine continues to step 947 where the control routine changes the intensity setting in accordance with the touched intensity button and returns to step 936. If, however, the control routine determines that an intensity button has not been touched, then the control routine continues to step 946. In step 946, the control routine determines whether the segment is complete. If, in step 946, the control routine determines that the segment is not complete, then the control routine returns to step 938. If, however, in step 946, the control routine determines that the segment is complete, then the control routine continues to step 948.

Figure 68:
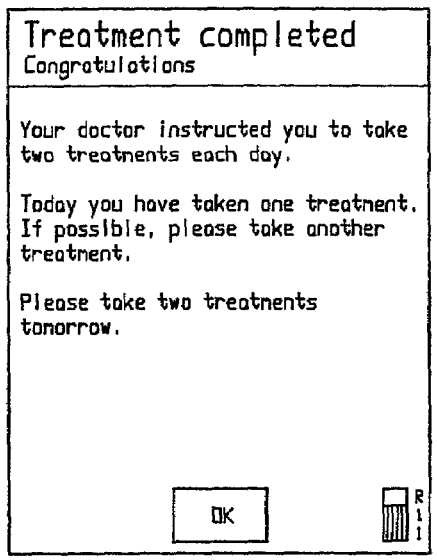

In step 948, the control routine determines whether this is the last segment in the treatment plan. If, in step 948, the control routine determines that this is not the last segment in the treatment plan, then the control routine returns to step 932. If, however, in step 948, the control routine determines that this is the last segment in the treatment plan, then the control routine continues to step 950. In step 950, the control routine displays a "Treatment completed" screen, an example which is shown in FIG. 68, and continues to step 952, after the user presses the "OK" button on the test screen. In step 952, the control routine displays the "How to recharge battery" screen, an example of which is shown in FIG. 41, and continues to step 953. In step 953, the control routine returns control of the device to the control routine that called the mini treatment option control routine of FIG. 39.

Although the above described exemplary embodiments have four independent channels, it is to be understood that an electro-medical device may have any number of channels and still be within the scope of the invention.

One advantage of the electro-medical device is that it can be programmed to accept various waveforms and display feedback and control information. Various waveforms can be used in a sequence with one another depending upon the need of the patient as determined by the physician. Thus, multiple waveforms can be integrated together. The device guides the physician through questions in order to determine a suggested electrical stimulation protocol and pad placement. The device maintains records of system setup and patient usage and progress.

Another feature of the preferred embodiment is shown in FIG. 151 which takes advantage of the flexibility of the electro-medical device. Below approximately 1,000 Hz, as frequency increases, intensity increases. As frequency increases above 1,000 Hz, however, sensation decreases so that the stimulation threshold increases. Thus, above 1,000 Hz, a greater intensity (amplitude) is needed to cause an action potential in the target treatment area. Decreasing intensity or increasing frequency will place the user below the stimulation threshold and produce a relax time for muscle stimulation.

As shown in FIG. 151, a diagonal therapy stimulation is provided which modulates frequency and amplitude to produce periods of action potentials or stimulation periods, and non-stimulation/relax periods.

Figure 152:
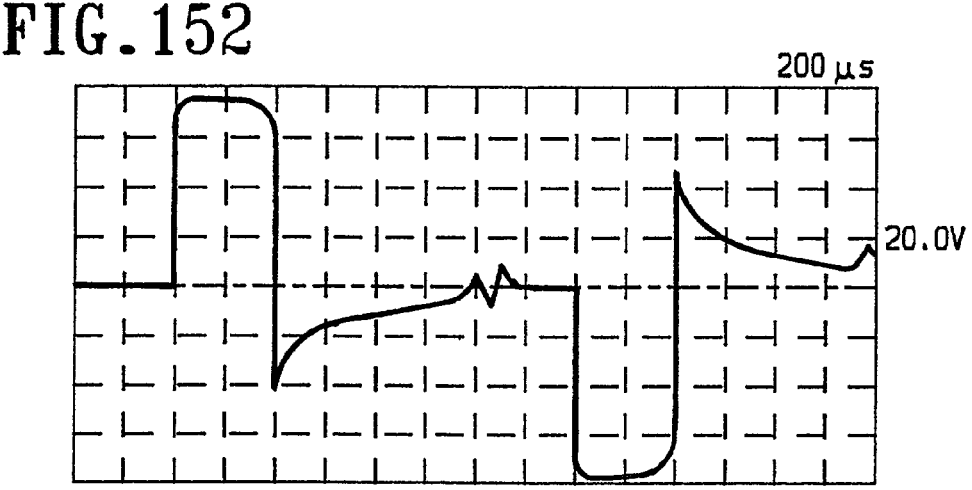
FIGS. 152 and 153 are charts illustrating R-wave stimulation.

A second wave therapy is shown in FIGS. 152 and 153, referred to as R-wave stimulation. For R-Wave therapy, the stimulation periods or "on" time are characterized as a period of electrical activity that generates action potentials and the "off" or relax time is a period of sub-threshold stimulation that does not create action potentials. In order to normalize metabolic activity, the relax time is a low-level, sub-threshold electrical activity.

At least two phases of stimulation are provided for R-wave stimulation, both muscle stimulation and interferential. The first phase or "on" time muscle stimulation phase, shown in FIG. 152, uses a parameter set that causes an action potential to be generated in a nerve or muscle. A second phase, or "off" time interferential phase of stimulation, shown in FIG. 153, has a parameter set that does not cause an action potential to be generated. The second phase forms a sinusoidal waveform that modulates frequency and amplitude to produce periods of non-action potential periods (relax phase). The modulated output frequency has an interval of one thousand to several thousand Hz with a modulation frequency of zero to several hundred Hz.

Preferably, the first phase parameter set is in the range of between 0–1,000 Hz (pulses per second) and the second phase has a parameter set including a frequency between 1,000–100,000 Hz. The stimulation level of the second phase is set lower than what would be necessary to cause an action potential to be generated. This "normalizing" current at higher frequencies has effects that are considered biochemical in nature as it triggers alternative mechanisms of action.

Figure 128:
Figure 129:
Figure 130:
Figure 131:
Figure 132:
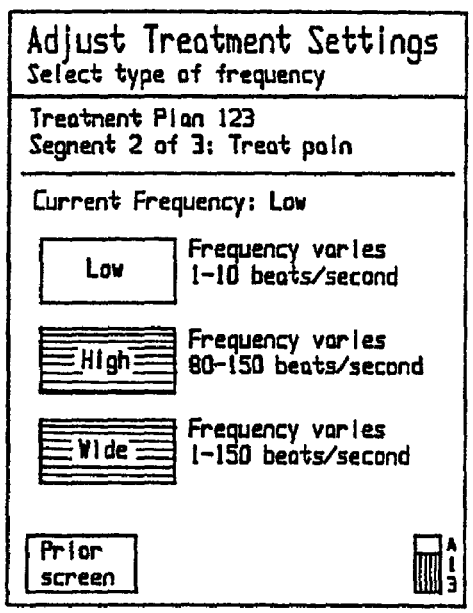
Figure 133:
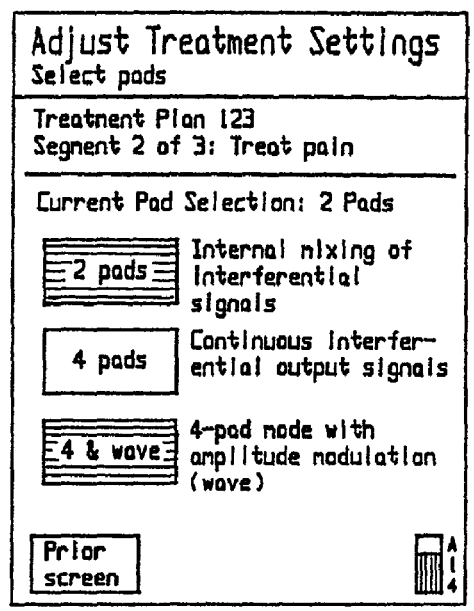
Figure 134:
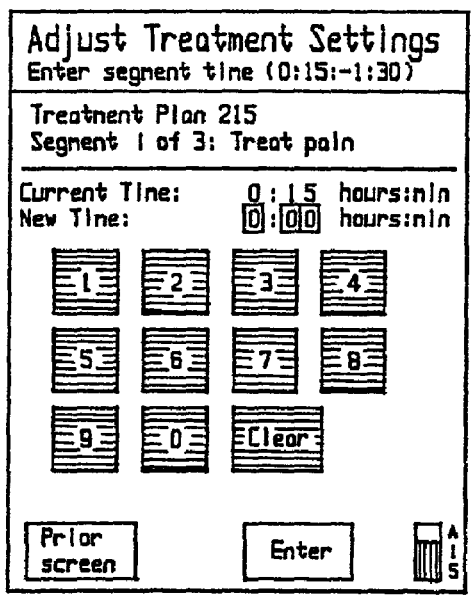

Thus, the electrotherapy device combines muscle stimulation with interferential in the same treatment by using the relax period to provide interferential stimulation. After the muscle stimulation contract period winds down, a brief interval of dead time can be provided before interferential stimulation begins. The interferential stimulation progresses for the relax time. Another interval of dead time can follow the end of the relax time prior to the next muscle stimulation contract period. Muscle stimulation preferably extends for approximately 40 minutes and the interval times between muscle stimulation and interferential is approximately 0.5 seconds, though can be adjusted on an interval selection screen such as shown in FIG. 128 to between 0.2–2.0 seconds.

This two-phase operation of the electrotherapy device is particularly useful for bone growth and muscle rehabilitation where pain is a factor. The electrotherapy device can be used for unsupervised in-home use or in a medical clinic environment for treatments to fit the patient, for studies, rehabilitation and other clinical purposes.

The muscle stimulation screens (FIGS. 45, 49, for instance) can be used to start, run and pause. A two-pad mode can be provided, so that the "adjust" button in FIG. 126 is disabled. In addition, amplitude modulation is disabled. Relax time can be changed to massage time (FIG. 125) to differentiate the two-phase operation and only normal mode can be accessed in FIG. 127.

While this invention has been described with the specific embodiments outlined above, many alternatives, modifications and variations will be apparent to those skilled in the art. Accordingly, the exemplary embodiments described above are illustrative and not limiting. Various changes may be made without departing from the spirit and scope of the invention.

We claim:

1. An electro-medical device, comprising:
   at least one independent channel in communication with at least one electrode for treating a body segment, said at least one independent channel including a drive circuit; and
   a controller in communication with said drive circuit to control said drive circuit to selectively provide a signal to said at least one electrode to provide a treatment to the body segment,
   wherein the signal comprises interferential current treatment signals and said controller controls said drive circuit to provide the interferential current signals in one of a continuous mode and a variable mode,
   wherein when the interferential current signals are in a continuous mode, the controller modulates the amplitude of the interferential current signal, and
   wherein the amplitude modulation repeatedly reduces the amplitude to 50 percent of a user selected value over a five second period and returns the amplitude to the user selected value.

2. An electro-medical device, comprising:
   at least one independent channel in communication with at least one electrode for treating a body segment, said at least one independent channel including a drive circuit; and
   a controller in communication with said drive circuit to control said drive circuit to selectively provide a signal to said at least one electrode to provide a treatment to the body segment,
   wherein the signal comprises interferential current treatment signals and,
   wherein said controller controls said drive circuit when providing the signals in one of a four pad mode and a pre-mixed two pad mode, said four pad mode providing a carrier frequency signal and an interference frequency signal such that they are mixed in the patient and said pre-mixed two pad mode pre-mixing said carrier frequency signal and said interference frequency signal in said device.

3. A electro-medical device, comprising:
at least one independent channel in communication with at least one electrode for providing a signal to at least one body segment; and
a controller that controls the signal that said at least one electrode provides to the at least one body segment,
wherein the signal comprises interferential current treatment signals and said controller controls said interferential current signals in one of a continuous mode and a variable mode,
wherein when said interferential current signals are in a continuous mode the interference frequency is adjustable between 0 and 200 beats per second, and
wherein the amplitude modulation repeatedly reduces the amplitude to 50 percent of a user selected value over a five second period and returns the amplitude to the user selected value.

4. A electro-medical device, comprising:
at least one independent channel in communication with at least one electrode for providing a signal to at least one body segment; and
a controller that controls the signal that said at least one electrode provides to the at least one body segment, and
wherein the signal comprises interferential current treatment signals and wherein said controller provides the signals in one of a four pad mode and a pre-mixed two pad mode, said four pad mode providing a carrier frequency signal and an interference frequency signal such that they are mixed in the patient and said pre-mixed two pad mode pre-mixing said carrier frequency signal and said interference frequency signal in said device.

5. An electro-medical device, comprising:
at least one independent channel in communication with at least one electrode for treating at least one body segment;
a drive circuit for driving said at least one independent channel;
a pulsed stimulator in selective communication with said drive circuit;
an interferential current stimulator in selective communication with said drive circuit; and
a processor that selectively connects one of said pulsed stimulator and said interferential current stimulator to said drive circuit and that controls the selected stimulator to provide a signal that treats said body segment,
wherein the signal comprises an interferential current treatment signals and said controller controls said drive circuit when providing said interferential current signals in one of a continuous mode and a variable mode,
wherein when said interferential current signals are in a continuous mode, the controller modulates the amplitude of the interferential current signal, and
wherein the amplitude modulation repeatedly reduces the amplitude to 50 percent of a user selected value over a five second period and returns the amplitude to the user selected value.

6. An electro-medical device, comprising:
at least one independent channel in communication with at least one electrode for treating at least one body segment;
a drive circuit for driving said at least one independent channel;
a pulsed stimulator in selective communication with said drive circuit;
an interferential current stimulator in selective communication with said drive circuit; and
a processor that selectively connects one of said pulsed stimulator and said interferential current stimulator to said drive circuit and that controls the selected stimulator to provide a signal that treats said body segment, and
wherein the signal comprises interferential current treatment signals and wherein said controller controls said drive circuit when providing the signals in one of a four pad mode and a pre-mixed two pad mode, said four pad mode providing a carrier frequency signal and an interference frequency signal such that they are mixed in the patient and said pre-mixed two pad mode pre-mixing said carrier frequency signal and said interference frequency signal in said device.

7. An electro-medical device, comprising:
a drive circuit adapted to be connected to at least one corresponding electrode for treating a body segment;
a multiplexer in communication with said drive circuit;
a programmable logic device in communication with said multiplexer;
a sine wave generator in communication with said multiplexer;
a processor in communication with said sine wave generator and said programmable logic device; and
an interactive liquid crystal display in communication with said processor, wherein said processor is responsive to a user selection of a treatment from a plurality of treatments received from said interactive liquid crystal display to control said multiplexer and at least one of said programmable logic device and said sine wave generator to generate a treatment signal at said drive circuit that corresponds to said selected treatment,
wherein the signal comprises interferential current treatment signals and further comprising a controller that controls said drive circuit to provide the interferential current signals in one of a continuous mode and a variable mode,
wherein when said interferential current signals are in a continuous mode, the controller modulates the amplitude of the interferential current signal, and
wherein the amplitude modulation repeatedly reduces the amplitude to 50 percent of a user selected value over a five second period and returns the amplitude to the user selected value.

8. An electro-medical device, comprising:
a drive circuit adapted to be connected to at least one corresponding electrode for treating a body segment;
a multiplexer in communication with said drive circuit;
a programmable logic device in communication with said multiplexer;
a sine wave generator in communication with said multiplexer;
a processor in communication with said sine wave generator and said programmable logic device; and
an interactive liquid crystal display in communication with said processor, wherein said processor is responsive to a user selection of a treatment from a plurality of treatments received from said interactive liquid crystal display to control said multiplexer and at least one of said programmable logic device and said sine wave generator to generate a treatment signal at said drive circuit that corresponds to said selected treatment, and wherein the signal comprises interferential current treatment signals and wherein said controller controls said drive circuit when providing said signals in one of a four pad mode and a pre-mixed two pad mode, said four pad mode providing a carrier frequency signal and an interference frequency signal such that they are mixed in the patient and said pre-mixed two pad mode pre-mixing said carrier frequency signal and said interference frequency signal in said device.

* * * * *